US011192952B2

(12) United States Patent
Brych et al.

(10) Patent No.: US 11,192,952 B2
(45) Date of Patent: Dec. 7, 2021

(54) FORMULATIONS COMPRISING HUMAN ANTI-RANKL MONOCLONAL ANTIBODIES, AND METHODS OF USING THE SAME

(71) Applicant: AMGEN INC., Thousand Oaks, CA (US)

(72) Inventors: Stephen Robert Brych, Thousand Oaks, CA (US); Lyanne M. Wong, Valencia, CA (US); Jaymille Fallon, Agoura Hills, CA (US); Monica Michelle Goss, Newbury Park, CA (US); Jian Hua Gu, Thousand Oaks, CA (US); Pavan Ghattyvenkatakrishna, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 70 days.

(21) Appl. No.: 16/608,375

(22) PCT Filed: Apr. 27, 2018

(86) PCT No.: PCT/US2018/029728
§ 371 (c)(1),
(2) Date: Oct. 25, 2019

(87) PCT Pub. No.: WO2018/200918
PCT Pub. Date: Nov. 1, 2018

(65) Prior Publication Data
US 2020/0354463 A1 Nov. 12, 2020

Related U.S. Application Data
(60) Provisional application No. 62/492,056, filed on Apr. 28, 2017.

(51) Int. Cl.
C07K 16/28 (2006.01)
A61K 39/00 (2006.01)

(52) U.S. Cl.
CPC .... *C07K 16/2875* (2013.01); *A61K 2039/505* (2013.01); *C07K 2317/21* (2013.01); *C07K 2317/52* (2013.01); *C07K 2317/55* (2013.01); *C07K 2317/76* (2013.01)

(58) Field of Classification Search
CPC ............ C07K 16/2875; C07K 2317/21; C07K 2317/76; A61K 2039/505
See application file for complete search history.

(56) References Cited

U.S. PATENT DOCUMENTS

| 2011/0060290 A1 | 3/2011 | Bonk et al. |
| 2014/0178383 A1 | 6/2014 | Brige et al. |
| 2016/0333101 A1 | 11/2016 | Zhou et al. |

FOREIGN PATENT DOCUMENTS

| CA | 2790018 A1 | 7/2008 |
| WO | 2003/002713 A2 | 1/2003 |
| WO | 2007/059136 A2 | 5/2007 |
| WO | 2010/022120 A1 | 2/2010 |
| WO | 2012/038504 A2 | 3/2012 |
| WO | 2012/141978 A2 | 10/2012 |
| WO | WO-2015/134406 A1 | 9/2015 |

OTHER PUBLICATIONS

Dubey K, et al. (2015) Amino Acids. 47:2551-2560. (DOI 10.1007/s00726-015-2046-6).*
Xgeva(R) FDA label. Revised Jun. 2013. Submitted by Applicants Sep. 3, 2021.*
PubMed Search Results for "Skeletal-Related-Event". Submitted by Applicants Sep. 3, 2021.*
"Highlights of Prescribing Information: Prolia™ (denosumab)", 20 pp., Amgen Inc. (Sep. 2011).
"Highlights of Prescribing Information: Xgeva™ (denosumab)", 20 pp., Amgen Inc. (Jun. 2013).
Falconer et al., Stabilization of a monoclonal antibody during purification and formulation by addition of basic amino acid excipients, J. Chem. Tech. & Biotech., 86(7):942-8 (Jul. 2011).
Inoue et al., Specific decrease in solution viscosity of antibodies by arginine for therapeutic formulations, Mol. Pharm., 11(6):1889-96 (Jun. 2014).
International Application No. PCT/US2018/029728, International Search Report and Written Opinion, dated Oct. 17, 2018.
International Application No. PCT/US2018/029728, Invitation to Pay Additional Fees and, Where Applicable, Protest Fee, dated Aug. 22, 2018.
Wang et al., Viscosity-Lowering Effect of Amino Acids and Salts on Highly Concentrated Solutions of Two IgG1 Monoclonal Antibodies, Mol. Pharm., 12(12):4478-87 (Dec. 2015).
Johnson and Rostovtsev, "High Concentration Biologic Formulations: Challenges and Solutions," retrieved from the internet: URL: https://www.drugdiscoverytrends.com/high-concentration-biologic-formulations-challenges-and-solutions/, printed on Aug. 13, 2021.
Stefani and Rigacci, "Protein Folding and Aggregation into Amyloid: The Interference by Natural Phenolic Compounds," *Int. J. Mol. Sci.* 14: 12411-12457 (2013).
Wang et al., "Antibody Structure, Instability, and Formulation," *Journal of Pharmaceutical Sciences* 96(1): 1-26 (2007).
Daugherty and Mrsny, "Formulation and delivery issues for monoclonal antibody therapeutics" *Advanced Drug Delivery Reviews* 58(5-6): 686-706 (2006).

(Continued)

Primary Examiner — Robert S Landsman
(74) Attorney, Agent, or Firm — Julie J. Hong

(57) ABSTRACT

Disclosed herein are aqueous pharmaceutical formulations comprising denosumab or another human anti-RANKL monoclonal antibody or portion thereof, and characteristics of pH, buffer systems, and amino acid aggregation inhibitors. Also disclosed are presentation of the formulation for use, e.g. in a single-use vial, single-use syringe, or glass container, methods of using the formulations and articles for preventing or treating diseases, and related kits.

42 Claims, 27 Drawing Sheets
Specification includes a Sequence Listing.

(56) References Cited

OTHER PUBLICATIONS

Rudikoff et al., "Single amino acid substitution altering antigen-binding specificity," *PNAS* 79(6): 1979-1983 (1982).
Tamura et al., "Structural Correlates of an Anticarcinoma Antibody: Identification of Specificity-Determining Residues (SDRs) and Development of a Minimally Immunogenic Antibody Variant by Retention of SDRs Only," *Journal of Immunology* 164(3): 1432-1441 (2000).

\* cited by examiner

**LC 125-132(+2)
QLKSGTAS**

**HC 47-59(+1)
WVSGITGSGGSTY**

SEQUENCE LISTING

<160> NUMBER OF SEQ ID NOS: 27

<210> SEQ ID NO 1
<211> LENGTH: 108
<212> TYPE: PRT
<213> ORGANISM: Homo sapiens
<220> FEATURE:
<221> NAME/KEY: MISC_FEATURE
<223> OTHER INFORMATION: denosumab variable light chain

<400> SEQUENCE: 1

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys
            100                 105
```

<210> SEQ ID NO 2
<211> LENGTH: 122
<212> TYPE: PRT
<213> ORGANISM: Homo sapiens
<220> FEATURE:
<221> NAME/KEY: MISC_FEATURE
<223> OTHER INFORMATION: denosumab variable heavy chain

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser
        115                 120
```

<210> SEQ ID NO 3
<211> LENGTH: 235
<212> TYPE: PRT
<213> ORGANISM: Homo sapiens
<220> FEATURE:
<221> NAME/KEY: MISC_FEATURE
<223> OTHER INFORMATION: denosumab full length light chain

<400> SEQUENCE: 3

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Val Arg Gly Arg Tyr Leu Ala Trp Tyr Gln Gln Lys Pro Gly Gln Ala
    50                  55                  60

Pro Arg Leu Leu Ile Tyr Gly Ala Ser Ser Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Phe Tyr Cys Gln Gln Tyr
            100                 105                 110

Gly Ser Ser Pro Arg Thr Phe Gly Gln Gly Thr Lys Val Glu Ile Lys
    115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
    195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys
225                 230                 235

<210> SEQ ID NO 4
<211> LENGTH: 467
<212> TYPE: PRT
<213> ORGANISM: Homo sapiens
<220> FEATURE:
<221> NAME/KEY: MISC_FEATURE
<223> OTHER INFORMATION: denosumab full length heavy chain

<400> SEQUENCE: 4

Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Thr Phe
            35                  40                  45

Ser Ser Tyr Ala Met Ser Trp Val Arg Gln Ala Pro Lys Gly Leu
    50                  55                  60

Glu Trp Val Ser Gly Ile Thr Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Pro Gly Thr Thr Val Ile Met Ser Trp Phe
```

```
                    115                 120                 125
Asp Pro Trp Gly Gln Gly Thr Leu Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160

Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 5
<211> LENGTH: 12
<212> TYPE: PRT
<213> ORGANISM: Homo sapiens
<220> FEATURE:
<221> NAME/KEY: MISC_FEATURE
<223> OTHER INFORMATION: Light Chain CDR 1

<400> SEQUENCE: 5
```

```
Arg Ala Ser Gln Ser Val Arg Gly Arg Tyr Leu Ala
1               5                   10

<210> SEQ ID NO 6
<211> LENGTH: 7
<212> TYPE: PRT
<213> ORGANISM: Homo sapiens
<220> FEATURE:
<221> NAME/KEY: MISC_FEATURE
<223> OTHER INFORMATION: Light Chain CDR 2

<400> SEQUENCE: 6

Gly Ala Ser Ser Arg Ala Thr
1               5

<210> SEQ ID NO 7
<211> LENGTH: 9
<212> TYPE: PRT
<213> ORGANISM: Homo sapiens
<220> FEATURE:
<221> NAME/KEY: MISC_FEATURE
<223> OTHER INFORMATION: Light Chain CDR 3

<400> SEQUENCE: 7

Gln Gln Tyr Gly Ser Ser Pro Arg Thr
1               5

<210> SEQ ID NO 8
<211> LENGTH: 5
<212> TYPE: PRT
<213> ORGANISM: Homo sapiens
<220> FEATURE:
<221> NAME/KEY: MISC_FEATURE
<223> OTHER INFORMATION: Heavy Chain CDR 1

<400> SEQUENCE: 8

Ser Tyr Ala Met Ser
1               5

<210> SEQ ID NO 9
<211> LENGTH: 17
<212> TYPE: PRT
<213> ORGANISM: Homo sapiens
<220> FEATURE:
<221> NAME/KEY: MISC_FEATURE
<223> OTHER INFORMATION: Heavy Chain CDR 2

<400> SEQUENCE: 9

Gly Ile Thr Gly Ser Gly Gly Ser Thr Tyr Tyr Ala Asp Ser Val Lys
1               5                   10                  15

Gly

<210> SEQ ID NO 10
<211> LENGTH: 13
<212> TYPE: PRT
<213> ORGANISM: Homo sapiens
<220> FEATURE:
<221> NAME/KEY: MISC_FEATURE
<223> OTHER INFORMATION: Heavy Chain CDR 3

<400> SEQUENCE: 10

Asp Pro Gly Thr Thr Val Ile Met Ser Trp Phe Asp Pro
1               5                   10

<210> SEQ ID NO 11
<211> LENGTH: 2141
<212> TYPE: DNA
```

<213> ORGANISM: Homo sapiens

<400> SEQUENCE: 11

```
ggccaaagcc gggctccaag tcggcgcccc acgtcgaggc tccgccgcag cctccggagt      60
tggccgcaga caagaagggg agggagcggg agagggagga gagctccgaa gcgagagggc     120
cgagcgccat gcgccgcgcc agcagagact acaccaagta cctgcgtggc tcggaggaga     180
tgggcggcgg ccccggagcc ccgcacgagg gccccctgca cgcccgccg ccgcctgcgc      240
cgcaccagcc ccccgccgcc tcccgctcca tgttcgtggc cctcctgggg ctggggctgg     300
gccaggttgt ctgcagcgtc gccctgttct tctatttcag agcgcagatg gatcctaata     360
gaatatcaga agatggcact cactgcattt atagaatttt gagactccat gaaaatgcag     420
attttcaaga cacaactctg gagagtcaag atacaaaatt aatacctgat tcatgtagga     480
gaattaaaca ggccttttcaa ggagctgtgc aaaaggaatt acaacatatc gttggatcac     540
agcacatcag agcagagaaa gcgatggtgg atggctcatg gttagatctg ccaagagga     600
gcaagcttga agctcagcct tttgctcatc tcactattaa tgccaccgac atcccatctg     660
gttcccataa agtgagtctg tcctcttggt accatgatcg gggttgggcc aagatctcca     720
acatgacttt tagcaatgga aaactaatag ttaatcagga tggcttttat tacctgtatg     780
ccaacatttg ctttcgacat catgaaactt caggagacct agctacagag tatcttcaac     840
taatggtgta cgtcactaaa accagcatca aaatcccaag ttctcatacc ctgatgaaag     900
gaggaagcac caagtattgg tcagggaatt ctgaattcca tttttattcc ataaacgttg     960
gtggattttt taagttacgg tctggagagg aaatcagcat cgaggtctcc aacccctcct    1020
tactggatcc ggatcaggat gcaacatact ttggggcttt taaagttcga gatatagatt    1080
gagccccagt ttttggagtg ttatgtattt cctggatgtt tggaaacatt ttttaaaaca    1140
agccaagaaa gatgtatata ggtgtgtgag actactaaga ggcatggccc caacggtaca    1200
cgactcagta tccatgctct tgaccttgta gagaacacgc gtatttacct gccagtggga    1260
gatgttagac tcatggtgtg ttacacaatg gttttttaaat tttgtaatga attcctagaa    1320
ttaaaccaga ttggagcaat tacgggttga ccttatgaga aactgcatgt gggctatggg    1380
aggggttggt ccctggtcat gtgcccttc gcagctgaag tggagagggt gtcatctagc     1440
gcaattgaag gatcatctga aggggcaaat tcttttgaat tgttacatca tgctggaacc    1500
tgcaaaaaat acttttcta atgaggagag aaaatatatg tatttttata taatatctaa     1560
agttatattt cagatgtaat gttttctttg caaagtattg taaattatat ttgtgctata    1620
acagacatat ttaactggtg cactttgtaa attccctggg gaaaacttgc agctaaggag    1680
gggaaaaaaa tgttgtttcc taatatcaaa tgcagtatat ttcttcgttc ttttttaagtt   1740
aatagatttt ttcagacttg tcaagcctgt gcaaaaaat taaaatggat gccttgaata    1800
ataagcagga tgttggccac caggtgcctt tcaaatttag aaactaattg acttagaaa     1860
gctgacattg ccaaaagga tacataatgg gccactgaaa tttgtcaaga gtagttatat     1920
aattgttgaa caggtgtttt tccacaagtg ccgcaaattg taccttttttt ttttttttcaa   1980
aatagaaaag ttattagtgg tttatcagca aaaaagtcca attttaattt agtaaatgtt    2040
attttatact gtacaataaa aacattgcct ttgaatgtta attttttggt acaaaaataa    2100
atttatatga aaaaaaaaa aaaaaaaa aaaaaaaaa a                             2141
```

<210> SEQ ID NO 12
<211> LENGTH: 317

<212> TYPE: PRT
<213> ORGANISM: Homo sapiens

<400> SEQUENCE: 12

```
Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65              70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125

Lys Glu Leu Gln His Ile Val Gly Ser Gln His Ile Arg Ala Glu Lys
130                 135                 140

Ala Met Val Asp Gly Ser Trp Leu Asp Leu Ala Lys Arg Ser Lys Leu
145                 150                 155                 160

Glu Ala Gln Pro Phe Ala His Leu Thr Ile Asn Ala Thr Asp Ile Pro
                165                 170                 175

Ser Gly Ser His Lys Val Ser Leu Ser Ser Trp Tyr His Asp Arg Gly
            180                 185                 190

Trp Ala Lys Ile Ser Asn Met Thr Phe Ser Asn Gly Lys Leu Ile Val
        195                 200                 205

Asn Gln Asp Gly Phe Tyr Tyr Leu Tyr Ala Asn Ile Cys Phe Arg His
210                 215                 220

His Glu Thr Ser Gly Asp Leu Ala Thr Glu Tyr Leu Gln Leu Met Val
225                 230                 235                 240

Tyr Val Thr Lys Thr Ser Ile Lys Ile Pro Ser Ser His Thr Leu Met
                245                 250                 255

Lys Gly Gly Ser Thr Lys Tyr Trp Ser Gly Asn Ser Glu Phe His Phe
            260                 265                 270

Tyr Ser Ile Asn Val Gly Gly Phe Phe Lys Leu Arg Ser Gly Glu Glu
        275                 280                 285

Ile Ser Ile Glu Val Ser Asn Pro Ser Leu Leu Asp Pro Asp Gln Asp
290                 295                 300

Ala Thr Tyr Phe Gly Ala Phe Lys Val Arg Asp Ile Asp
305                 310                 315
```

<210> SEQ ID NO 13
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 13

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
```

```
                     20                  25                  30
Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 14
<211> LENGTH: 448
<212> TYPE: PRT
<213> ORGANISM: Artificial Sequence
<220> FEATURE:
<223> OTHER INFORMATION: Synthetic Polypeptide

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
```

```
                 165                 170                 175
Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 15
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (14)..(14)
<223> OTHER INFORMATION: Xaa is Cys or Ser
<220> FEATURE:
<221> NAME/KEY: misc_feature
<222> LOCATION: (16)..(16)
<223> OTHER INFORMATION: Xaa is Arg or Lys
<220> FEATURE:
<221> NAME/KEY: misc_feature
<222> LOCATION: (20)..(20)
<223> OTHER INFORMATION: Xaa is Glu or Gly
<220> FEATURE:
<221> NAME/KEY: misc_feature
<222> LOCATION: (21)..(21)
<223> OTHER INFORMATION: Xaa is Ser or Gly
<220> FEATURE:
<221> NAME/KEY: misc_feature
<222> LOCATION: (75)..(75)
```

```
<223> OTHER INFORMATION: Xaa is Ser or Asn
<220> FEATURE:
<221> NAME/KEY: misc_feature
<222> LOCATION: (76)..(76)
<223> OTHER INFORMATION: Xaa is Leu or Phe
<220> FEATURE:
<221> NAME/KEY: misc_feature
<222> LOCATION: (79)..(79)
<223> OTHER INFORMATION: Xaa is Lys or Gln
<220> FEATURE:
<221> NAME/KEY: misc_feature
<222> LOCATION: (82)..(82)
<223> OTHER INFORMATION: Xaa is Thr or Ile
<220> FEATURE:
<221> NAME/KEY: misc_feature
<222> LOCATION: (86)..(86)
<223> OTHER INFORMATION: Xaa is Asp or Asn
<220> FEATURE:
<221> NAME/KEY: misc_feature
<222> LOCATION: (97)..(97)
<223> OTHER INFORMATION: Xaa is Arg, Thr, or Lys
<220> FEATURE:
<221> NAME/KEY: misc_feature
<222> LOCATION: (100)..(100)
<223> OTHER INFORMATION: Xaa is Ser, Arg, or Pro
<220> FEATURE:
<221> NAME/KEY: misc_feature
<222> LOCATION: (102)..(102)
<223> OTHER INFORMATION: Xaa is Tyr, Cys, or Ser
<220> FEATURE:
<221> NAME/KEY: misc_feature
<222> LOCATION: (103)..(103)
<223> OTHER INFORMATION: Xaa is Gly or Cys
<220> FEATURE:
<221> NAME/KEY: misc_feature
<222> LOCATION: (104)..(104)
<223> OTHER INFORMATION: Xaa is absent or Asp
<220> FEATURE:
<221> NAME/KEY: misc_feature
<222> LOCATION: (105)..(105)
<223> OTHER INFORMATION: Xaa is absent or Lys
<220> FEATURE:
<221> NAME/KEY: misc_feature
<222> LOCATION: (106)..(106)
<223> OTHER INFORMATION: Xaa is absent or Thr
<220> FEATURE:
<221> NAME/KEY: misc_feature
<222> LOCATION: (107)..(107)
<223> OTHER INFORMATION: Xaa is Pro, Val or His
<220> FEATURE:
<221> NAME/KEY: misc_feature
<222> LOCATION: (108)..(108)
<223> OTHER INFORMATION: Xaa is Pro, Glu, or Thr
<220> FEATURE:
<221> NAME/KEY: misc_feature
<222> LOCATION: (111)..(111)
<223> OTHER INFORMATION: Xaa is Ser or Pro
<220> FEATURE:
<221> NAME/KEY: misc_feature
<222> LOCATION: (116)..(116)
<223> OTHER INFORMATION: Xaa is Glu or Pro
<220> FEATURE:
<221> NAME/KEY: misc_feature
<222> LOCATION: (117)..(117)
<223> OTHER INFORMATION: Xaa is Phe, Val, or Leu
<220> FEATURE:
<221> NAME/KEY: misc_feature
<222> LOCATION: (118)..(118)
<223> OTHER INFORMATION: Xaa is Leu or Ala
<220> FEATURE:
<221> NAME/KEY: misc_feature
<222> LOCATION: (120)..(120)
<223> OTHER INFORMATION: Xaa is absent or Gly
<220> FEATURE:
<221> NAME/KEY: misc_feature
<222> LOCATION: (151)..(151)
<223> OTHER INFORMATION: Xaa is Gln or His
<220> FEATURE:
<221> NAME/KEY: misc_feature
```

```
<222> LOCATION: (157)..(157)
<223> OTHER INFORMATION: Xaa is Gln or Lys
<220> FEATURE:
<221> NAME/KEY: misc_feature
<222> LOCATION: (179)..(179)
<223> OTHER INFORMATION: Xaa is Phe or Tyr
<220> FEATURE:
<221> NAME/KEY: misc_feature
<222> LOCATION: (183)..(183)
<223> OTHER INFORMATION: Xaa is Tyr or Phe
<220> FEATURE:
<221> NAME/KEY: misc_feature
<222> LOCATION: (192)..(192)
<223> OTHER INFORMATION: Xaa is Leu or Val
<220> FEATURE:
<221> NAME/KEY: misc_feature
<222> LOCATION: (210)..(210)
<223> OTHER INFORMATION: Xaa is Gly or Ala
<220> FEATURE:
<221> NAME/KEY: misc_feature
<222> LOCATION: (213)..(213)
<223> OTHER INFORMATION: Xaa is Ser or Ala
<220> FEATURE:
<221> NAME/KEY: misc_feature
<222> LOCATION: (214)..(214)
<223> OTHER INFORMATION: Xaa is Ser or Pro
<220> FEATURE:
<221> NAME/KEY: misc_feature
<222> LOCATION: (222)..(222)
<223> OTHER INFORMATION: Xaa is Ala or Thr
<220> FEATURE:
<221> NAME/KEY: misc_feature
<222> LOCATION: (238)..(238)
<223> OTHER INFORMATION: Xaa is Gln or Arg
<220> FEATURE:
<221> NAME/KEY: misc_feature
<222> LOCATION: (239)..(239)
<223> OTHER INFORMATION: Xaa is Glu or Asp
<220> FEATURE:
<221> NAME/KEY: misc_feature
<222> LOCATION: (241)..(241)
<223> OTHER INFORMATION: Xaa is Met or Leu
<220> FEATURE:
<221> NAME/KEY: misc_feature
<222> LOCATION: (280)..(280)
<223> OTHER INFORMATION: Xaa is Val or Met
<220> FEATURE:
<221> NAME/KEY: misc_feature
<222> LOCATION: (292)..(292)
<223> OTHER INFORMATION: Xaa is Arg or Lys
<220> FEATURE:
<221> NAME/KEY: misc_feature
<222> LOCATION: (302)..(302)
<223> OTHER INFORMATION: Xaa is Glu or Gln
<220> FEATURE:
<221> NAME/KEY: misc_feature
<222> LOCATION: (328)..(328)
<223> OTHER INFORMATION: Xaa is Leu or Pro

<400> SEQUENCE: 15

Ala Ser Thr Lys Gly Pro Ser Val Phe Pro Leu Ala Pro Xaa Ser Xaa
1               5                   10                  15

Ser Thr Ser Xaa Xaa Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Xaa Xaa Gly Thr Xaa Thr
65                  70                  75                  80

Tyr Xaa Cys Asn Val Xaa His Lys Pro Ser Asn Thr Lys Val Asp Lys
            85                  90                  95
```

```
Xaa Val Glu Xaa Lys Xaa Xaa Xaa Xaa Xaa Cys Pro Xaa Cys
            100                 105                 110

Pro Ala Pro Xaa Xaa Xaa Gly Xaa Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser Xaa Glu Asp Pro Glu Val Xaa Phe Asn Trp
145                 150                 155                 160

Tyr Val Asp Gly Val Glu Val His Asn Ala Lys Thr Lys Pro Arg Glu
                165                 170                 175

Glu Gln Xaa Asn Ser Thr Xaa Arg Val Val Ser Val Leu Thr Val Xaa
            180                 185                 190

His Gln Asp Trp Leu Asn Gly Lys Glu Tyr Lys Cys Lys Val Ser Asn
        195                 200                 205

Lys Xaa Leu Pro Xaa Xaa Ile Glu Lys Thr Ile Ser Lys Xaa Lys Gly
    210                 215                 220

Gln Pro Arg Glu Pro Gln Val Tyr Thr Leu Pro Pro Ser Xaa Xaa Glu
225                 230                 235                 240

Xaa Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Xaa Leu Asp Ser Asp Gly Ser Phe Phe
            275                 280                 285

Leu Tyr Ser Xaa Leu Thr Val Asp Lys Ser Arg Trp Gln Xaa Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Xaa Gly Lys
                325                 330

<210> SEQ ID NO 16
<211> LENGTH: 326
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: IgG2 Constant HC

<400> SEQUENCE: 16

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 17
<211> LENGTH: 330
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: IgG1 constant HC

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 18
<211> LENGTH: 327
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: IgG4 constant HC

<400> SEQUENCE: 18

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140

| | | | | | | | | | | | | | | | |
|---|---|---|---|---|---|---|---|---|---|---|---|---|---|---|---|
|Asp|Val|Ser|Gln|Glu|Asp|Pro|Glu|Val|Gln|Phe|Asn|Trp|Tyr|Val|Asp|
|145| | | | |150| | | | |155| | | | |160|

Gly Val Glu Val His Asn Ala Lys Thr Lys Pro Arg Glu Glu Gln Phe
                165                    170                    175

Asn Ser Thr Tyr Arg Val Val Ser Val Leu Thr Val Leu His Gln Asp
            180                    185                    190

Trp Leu Asn Gly Lys Glu Tyr Lys Cys Lys Val Ser Asn Lys Gly Leu
        195                    200                    205

Pro Ser Ser Ile Glu Lys Thr Ile Ser Lys Ala Lys Gly Gln Pro Arg
210                        215                    220

Glu Pro Gln Val Tyr Thr Leu Pro Pro Ser Gln Glu Glu Met Thr Lys
225            230                  235            240

Asn Gln Val Ser Leu Thr Cys Leu Val Lys Gly Phe Tyr Pro Ser Asp
            245                  250              255

Ile Ala Val Glu Trp Glu Ser Asn Gly Gln Pro Glu Asn Asn Tyr Lys
        260                    265                270

Thr Thr Pro Pro Val Leu Asp Ser Asp Gly Ser Phe Phe Leu Tyr Ser
            275                  280              285

Arg Leu Thr Val Asp Lys Ser Arg Trp Gln Glu Gly Asn Val Phe Ser
290                  295                  300

Cys Ser Val Met His Glu Ala Leu His Asn His Tyr Thr Gln Lys Ser
305            310                  315            320

Leu Ser Leu Ser Leu Gly Lys
        325

```
<210> SEQ ID NO 19
<211> LENGTH: 324
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: variable LC

<400> SEQUENCE: 19
```
gaaattgtgt tgacgcagtc tccaggcacc ctgtctttgt ctccagggga aagagccacc   60
ctctcctgta gggccagtca gagtgttcgc ggcaggtact tagcctggta ccagcagaaa  120
cctggccagg ctcccaggct cctcatctat ggtgcatcca gcaggccac tggcatccca  180 gacaggttca gtggcagtgg gtctgggaca gacttcactc tcaccatcag cagactggag  240
cctgaagatt ttgcagtgtt ttactgtcag cagtatggta gttcacctcg gacgttcggc  300
caagggacca aggtggaaat caaa  324

```
<210> SEQ ID NO 20
<211> LENGTH: 366
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: variable HC

<400> SEQUENCE: 20
```
gaggtgcagc tgttggagtc tgggggaggc ttggtacagc ctgggggtc cctgagactc   60 tcctgtgcag cctctggatt cacctttagc agctatgcca tgagctgggt ccgccaggct  120
ccagggaagg ggctggagtg ggtctcaggt attactggga gtggtggtag tacatactac  180

```
gcagactccg tgaagggccg gttcaccatc tccagagaca attccaagaa cacgctgtat    240
ctgcaaatga acagcctgag agccgaggac acggccgtat attactgtgc gaaagatcca    300
gggactacgg tgattatgag ttggttcgac ccctggggcc agggaaccct ggtcaccgtc    360
tcctca                                                              366

<210> SEQ ID NO 21
<211> LENGTH: 705
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: full length LC

<400> SEQUENCE: 21
atggaaaccc cagcgcagct tctcttcctc ctgctactct ggctcccaga taccaccgga     60
gaaattgtgt tgacgcagtc tccaggcacc ctgtctttgt ctccagggga aagagccacc    120
ctctcctgta gggccagtca gagtgttcgc ggcaggtact tagcctggta ccagcagaaa    180
cctggccagg ctcccaggct cctcatctat ggtgcatcca gcagggccac tggcatccca    240
gacaggttca gtggcagtgg gtctgggaca gacttcactc tcaccatcag cagactggag    300
cctgaagatt ttgcagtgtt ttactgtcag cagtatggta gttcacctcg acgttcggc    360 caagggacca aggtggaaat caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgt                   705

<210> SEQ ID NO 22
<211> LENGTH: 1401
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: full length HC

<400> SEQUENCE: 22
atggagtttg ggctgagctg cttttttctt gtggctattt taaaaggtgt ccagtgtgag     60
gtgcagctgt tggagtctgg gggaggcttg gtacagcctg gggggtccct gagactctcc    120
tgtgcagcct ctggattcac ctttagcagc tatgccatga gctgggtccg ccaggctcca    180
gggaaggggc tggagtgggt ctcaggtatt actgggagtg gtggtagtac atactacgca    240
gactccgtga agggccggtt caccatctcc agagacaatt ccaagaacac gctgtatctg    300
caaatgaaca gcctgagagc cgaggacacg gccgtatatt actgtgcgaa agatccaggg    360
actacggtga ttatgagttg gttcgacccc tggggccagg gaaccctggt caccgtctcc    420
tcagcctcca ccaagggccc atcggtcttc cccctggcgc cctgctccag gagcacctcc    480
gagagcacag cggccctggg ctgcctggtc aaggactact ccccgaacc ggtgacggtg    540 tcgtggaact caggcgctct gaccagcggc gtgcacacct tcccagctgt cctacagtcc    600
```

```
tcaggactct actccctcag cagcgtggtg accgtgccct ccagcaactt cggcacccag      660
acctacacct gcaacgtaga tcacaagccc agcaacacca aggtggacaa gacagttgag      720
cgcaaatgtt gtgtcgagtg cccaccgtgc ccagcaccac ctgtggcagg accgtcagtc      780
ttcctcttcc ccccaaaacc caaggacacc ctcatgatct cccggacccc tgaggtcacg      840
tgcgtggtgg tggacgtgag ccacgaagac cccgaggtcc agttcaactg gtacgtggac      900
ggcgtggagg tgcataatgc caagacaaag ccacgggagg agcagttcaa cagcacgttc      960
cgtgtggtca gcgtcctcac cgttgtgcac caggactggc tgaacggcaa ggagtacaag     1020
tgcaaggtct ccaacaaagg cctcccagcc cccatcgaga aaccatctc caaaaccaaa      1080 gggcagcccc gagaaccaca ggtgtacacc ctgcccccat cccgggagga tgaccaag      1140 aaccaggtca gcctgacctg cctggtcaaa ggcttctacc ccagcgacat cgccgtggag     1200
tgggagagca atgggcagcc ggagaacaac tacaagacca cctcccat gctggactcc      1260 gacggctcct tcttcctcta cagcaagctc accgtggaca gagcaggtg gcagcagggg     1320 aacgtcttct catgctccgt gatgcatgag gctctgcaca accactacac gcagaagagc     1380
ctctccctgt ctccgggtaa a                                                1401

<210> SEQ ID NO 23
<211> LENGTH: 645
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: mature LC

<400> SEQUENCE: 23
gaaattgtgt tgacgcagtc tccaggcacc ctgtctttgt ctccagggga aagagccacc       60
ctctcctgta gggccagtca gagtgttcgc ggcaggtact tagcctgta ccagcagaaa      120 cctggccagg ctcccaggct cctcatctat ggtgcatcca gcagggccac tggcatccca      180
gacaggttca gtggcagtgg gtctgggaca gacttcactc tcaccatcag cagactggag      240
cctgaagatt ttgcagtgtt ttactgtcag cagtatggta gttcacctcg gacgttcggc      300
caagggacca aggtggaaat caaacgaact gtggctgcac catctgtctt catcttcccg      360
ccatctgatg agcagttgaa atctggaact gcctctgttg tgtgcctgct gaataacttc      420
tatcccagag aggccaaagt acagtggaag gtggataacg ccctccaatc gggtaactcc      480
caggagagtg tcacagagca ggacagcaag gacagcacct acagcctcag cagcaccctg      540
acgctgagca agcagactac gagaaacac aaagtctacg cctgcgaagt cacccatcag      600
ggcctgagct cgcccgtcac aaaagagcttc aacaggggag agtgt                     645

<210> SEQ ID NO 24
<211> LENGTH: 1344
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: mature HC

<400> SEQUENCE: 24
gaggtgcagc tgttggagtc tgggggaggc ttggtacagc ctggggggtc cctgagactc       60
tcctgtgcag cctctggatt caccttagc agctatgcca tgagctgggt ccgccaggct      120
```

```
ccagggaagg ggctggagtg ggtctcaggt attactggga gtggtggtag tacatactac    180
gcagactccg tgaagggccg gttcaccatc tccagagaca attccaagaa cacgctgtat    240
ctgcaaatga acagcctgag agccgaggac acggccgtat attactgtgc gaaagatcca    300
gggactacgg tgattatgag ttggttcgac ccctggggcc agggaaccct ggtcaccgtc    360
tcctcagcct ccaccaaggg cccatcggtc ttccccctgg cgcctgctc caggagcacc     420 tccgagagca cagcggccct gggctgcctg gtcaaggact acttccccga accggtgacg    480
gtgtcgtgga actcaggcgc tctgaccagc ggcgtgcaca ccttcccagc tgtcctacag    540
tcctcaggac tctactccct cagcagcgtg gtgaccgtgc cctccagcaa cttcggcacc    600
cagacctaca cctgcaacgt agatcacaag cccagcaaca ccaaggtgga caagacagtt    660
gagcgcaaat gttgtgtcga gtgcccaccg tgcccagcac acctgtggc aggaccgtca     720 gtcttcctct tccccccaaa acccaaggac accctcatga tctcccggac ccctgaggtc    780
acgtgcgtgg tggtggacgt gagccacgaa gaccccgagg tccagttcaa ctggtacgtg    840
gacggcgtgg aggtgcataa tgccaagaca aagccacggg aggagcagtt caacagcacg    900
ttccgtgtgg tcagcgtcct caccgttgtg caccaggact ggctgaacgg caaggagtac    960
aagtgcaagg tctccaacaa aggcctccca gcccccatcg agaaaaccat ctccaaaacc    1020
aaagggcagc cccgagaacc acaggtgtac accctgcccc catcccggga ggagatgacc    1080
aagaaccagg tcagcctgac ctgcctggtc aaaggcttct accccagcga catcgccgtg    1140
gagtgggaga gcaatgggca gccggagaac aactacaaga ccacacctcc catgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                          1344
```

```
<210> SEQ ID NO 25
<211> LENGTH: 20
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: signal peptide of full length LC of SEQ 3

<400> SEQUENCE: 25

Met Glu Thr Pro Ala Gln Leu Leu Phe Leu Leu Leu Leu Trp Leu Pro
1               5                   10                  15

Asp Thr Thr Gly
            20

<210> SEQ ID NO 26
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: signal peptide of full length HC of SEQ 4

<400> SEQUENCE: 26

Met Glu Phe Gly Leu Ser Trp Leu Phe Leu Val Ala Ile Leu Lys Gly
1               5                   10                  15

Val Gln Cys
```

```
<210> SEQ ID NO 27
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 27

Gly Phe Thr Phe Ser Ser Tyr Ala Met Ser
1               5                   10
```

FORMULATIONS COMPRISING HUMAN ANTI-RANKL MONOCLONAL ANTIBODIES, AND METHODS OF USING THE SAME

CROSS-REFERENCE TO RELATED APPLICATION

The benefit under 35 U.S.C. § 119(e) of U.S. Provisional Patent Application No. 62/492,056, filed on Apr. 28, 2017, is hereby claimed, and the disclosure thereof is hereby incorporated by reference herein.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 49 kilobyte ASCII (Text) file named "51689A_Seqlisting.txt"; created on Apr. 20, 2018.

BACKGROUND

Field of the Disclosure

The invention relates to human anti-RANKL monoclonal antibodies, including high-concentration aqueous formulations of denosumab and biosimilars thereof.

Brief Description of Related Technology

Denosumab is commercially available in solution forms at strengths of 60 mg/mL and 70 mg/mL.

Increasing concentrations of protein formulations can cause problems with stability, for example aggregation resulting in formation of high molecular weight species (HMWS). HMWS, particularly those that conserve most of the native configuration of the monomer counterpart, can be of particular concern in some protein formulations. Aggregation can also potentially affect the subcutaneous bioavailability and pharmacokinetics of a therapeutic protein.

Filling and finishing operations, as well as administration, can involve steps of flowing protein solutions through piston pumps, peristaltic pumps, or needles for injection. Such processes can impart shear and mechanical stresses, which can cause denaturation of proteins and result in aggregation. This phenomenon can be exacerbated as protein solutions become more concentrated.

SUMMARY

Provided in accordance with the present invention is disclosure for the first time demonstrating that the addition of an amino acid aggregation inhibitor to an aqueous solution comprising a high concentration of an anti-RANKL antibody leads to a reduced amount of antibody aggregates formed over time, as well a slower formation rate of such aggregates. The present disclosure also provides for a pH effect on aggregate formation in concentrated aqueous solutions of anti-RANKL antibody, wherein decreased aggregate formation is observed when the pH of the aqueous solutions is in the range of about 5.0 to less than 5.2. Further suggested by the disclosure presented herein is that the stabilization of the anti-RANKL antibody occurs through interactions between the amino acid aggregation inhibitor and the antibody. Without being bound to any particular theory, it is contemplated that hydrophobic interactions, as well as other types of intermolecular interactions, between the amino acid aggregation inhibitor and the anti-RANKL antibody have a stabilizing effect on the concentrated antibody solutions.

Accordingly, the disclosure of the present invention relates to stable aqueous pharmaceutical formulations comprising a high concentration of an anti-RANKL antibody which formulations comprise low amounts (e.g., less than about 2%) of aggregates.

Accordingly, one aspect of the disclosure is an aqueous pharmaceutical formulation comprising a human anti-human receptor activator of nuclear factor kappa-B ligand (anti-RANKL) monoclonal antibody or an antigen-binding portion thereof at a concentration of greater than 70 mg/mL and having a pH in a range of about 5.0 to less than 5.2.

Another aspect of the disclosure is an aqueous pharmaceutical formulation comprising a mixture of a human anti-human receptor activator of nuclear factor kappa-B ligand (anti-RANKL) monoclonal antibody or an antigen-binding portion thereof and an amino acid aggregation inhibitor. In exemplary aspects, the amino acid aggregation inhibitor comprises an amino acid comprising a charged side chain, an aromatic amino acid, or a hydrophobic amino acid. In exemplary instances, the amino acid comprising a charged side chain is an amino acid comprising a positive-charged side chain, such as, for example, arginine and lysine. In exemplary aspects, the aromatic amino acid comprises a phenyl or an indole. Optionally, the aromatic amino acid further comprises a $C_1$-$C_6$ alkyl chain between the alpha carbon and the phenyl or indole. Amino acids, including, for instance, phenylalanine and tryptophan, are exemplary amino acid aggregation inhibitors. In exemplary instances, the amino acid aggregation inhibitor is a hydrophobic amino acid having a score greater than about 2.5 on the Kyte and Doolittle hydrophobicity scale. Optionally, the hydrophobic amino acid is valine, leucine or isoleucine. Additional amino acid aggregation inhibitors are contemplated as described herein.

In exemplary instances, the aqueous pharmaceutical formulation further comprises a tonicity modifier, a surfactant, a buffer, or any combination thereof.

Another aspect of the disclosure is a presentation of the formulation for storage or use, e.g. in a single-use vial, single-use syringe, or glass, glass-lined, or glass-coated primary container. An exemplary aspect of the disclosure is a container, optionally, a vial, pre-filled syringe (PFS), or glass container comprising any of the aqueous pharmaceutical formulations described herein. The container, in exemplary instances, comprises about 1 mL or less (e.g., about 0.5 mL) of the aqueous pharmaceutical formulation.

Another aspect of the disclosure provides methods of making a stable, aqueous pharmaceutical formulation comprising a human anti-human receptor activator of nuclear factor kappa-B ligand (anti-RANKL) monoclonal antibody, or an antigen-binding portion thereof, comprising combining the anti-RANKL monoclonal antibody, or antigen-binding portion thereof, at a concentration greater than 70 mg/mL with an amino acid aggregation inhibitor, a buffer, a surfactant, and optionally, a tonicity modifier. Aspects of the disclosure include the stable, aqueous pharmaceutical formulation made according to any one of the methods of making a stable, aqueous pharmaceutical formulation described herein.

Another aspect of the disclosure provides methods of using a formulation as described herein for preventing or treating a disease responsive to a human anti-RANKL monoclonal antibody or an antigen-binding portion thereof. In exemplary aspects, the use encompasses therapeutic treatment of a subject encompassing treatment or prevention of a skeletal-related event (SRE), treatment or prevention of a giant cell tumor of bone, treatment or prevention of hypercalcemia of malignancy, treatment or prevention of osteoporosis, or increasing bone mass, in a subject. For instance, the therapeutic treatment encompasses (a) treatment or prevention of an SRE in a subject with bone metastases from solid tumors, (b) treatment or prevention of an SRE in a subject who is an adult or a skeletally mature adolescent with giant cell tumor of bone that is unresectable or where surgical resection is likely to result in severe morbidity, (c) treatment of hypercalcemia of malignancy refractory to bisphonsphonate therapy in a subject, (d) treatment or prevention of an SRE in a subject with multiple myeloma or with bone metastases from a solid tumor, (e) treatment of osteoporosis of postmenopausal women at high risk for fracture, (f) treatment to increase bone mass in women at high risk for fracture receiving adjuvant aromatase inhibitor therapy for breast cancer, (g) treatment to increase bone mass in men at high risk for fracture receiving androgen deprivation therapy for nonmetastatic prostate cancer, (h) treatment to increase bone mass in men with osteoporosis at high risk for fracture, (i) therapy with calcium or vitamin D.

Additional aspects of the disclosure include a method of preventing a skeletal-related event (SRE) in a patient in need thereof, a method of treating giant cell tumor of bone in a patient in need thereof, a method of treating hypercalcemia of malignancy in a patient in need thereof, a method of treating osteoporosis in a patient in need thereof, and a method of increasing bone mass in a patient in need thereof. The methods comprise administering to the patient an effective amount of any one of the formulations described herein. In exemplary instances, the formulation is subcutaneously delivered to the patient.

Another aspect of the disclosure provides the use of denosumab, or another human anti-RANKL monoclonal antibody or an antigen-binding portion thereof, in the manufacture of a medicament as described herein for treating a patient in need of a human anti-RANKL monoclonal antibody.

Another aspect of the disclosure is a kit including a composition or article described herein together with a package insert, package label, instructions, or other labeling directing or disclosing any of the methods or embodiments disclosed herein.

Another aspect of the disclosure is a method of improving the stability of an aqueous pharmaceutical formulation including a human anti-human receptor activator of nuclear factor kappa-B ligand (anti-RANKL) monoclonal antibody or an antigen-binding portion thereof, at a concentration of greater than 70 mg/mL, including the step of preparing the aqueous pharmaceutical formulation including the human anti-human receptor activator of nuclear factor kappa-B ligand (anti-RANKL) monoclonal antibody or an antigen-binding portion thereof at a pH in a range of about 5.0 to less than 5.2, wherein the aqueous pharmaceutical formulation demonstrates improved stability at the pH in a range of about 5.0 to less than 5.2 compared to an equivalent aqueous pharmaceutical formulation that is not at a pH in a range of about 5.0 to less than 5.2.

Another aspect of the disclosure is a method of improving the stability of an aqueous pharmaceutical formulation including a human anti-human receptor activator of nuclear factor kappa-B ligand (anti-RANKL) monoclonal antibody or an antigen-binding portion thereof, including the step of preparing the aqueous pharmaceutical formulation comprising the human anti-human receptor activator of nuclear factor kappa-B ligand (anti-RANKL) monoclonal antibody or an antigen-binding portion thereof in admixture with an amino acid aggregation inhibitor, wherein the aqueous pharmaceutical formulation demonstrates improved stability with the amino acid aggregation inhibitor compared to an equivalent aqueous pharmaceutical formulation without the amino acid aggregation inhibitor.

Another aspect of the disclosure is a method of reducing the level of HMWS aggregates in a solution of denosumab or another human anti-RANKL monoclonal antibody.

Further aspects and advantages will be apparent to those of ordinary skill in the art from a review of the following detailed description, taken in conjunction with the drawings. While the compositions, articles, and methods are susceptible of embodiments in various forms, the description hereafter includes specific embodiments with the understanding that the disclosure is illustrative, and is not intended to limit the invention to the specific embodiments described herein. For the compositions, articles, and methods described herein, optional features, including but not limited to components, compositional ranges thereof, substituents, conditions, and steps, are contemplated to be selected from the various aspects, embodiments, and examples provided herein.

BRIEF DESCRIPTION OF THE DRAWINGS

FIGS. 13 and 16 relate to formulations comprising aromatic amino acids, FIGS. 14 and 17 relate to formulations comprising polar/charged amino acids, and FIGS. 15 and 18 relate to formulations comprising hydrophobic amino acids.

FIG. 40A is a graph of the Fraction of Denatured denosumab as a function of denaturant concentration. FIG. 40B is a graph plotting dF/d[denaturant] as a function of denaturant concentration.

FIG. 41A is a graph of the Fraction of Denatured denosumab as a function of denaturant concentration. FIG. 41B is a graph plotting dF/d[denaturant] as a function of denaturant concentration.

DETAILED DESCRIPTION

Figure 1:
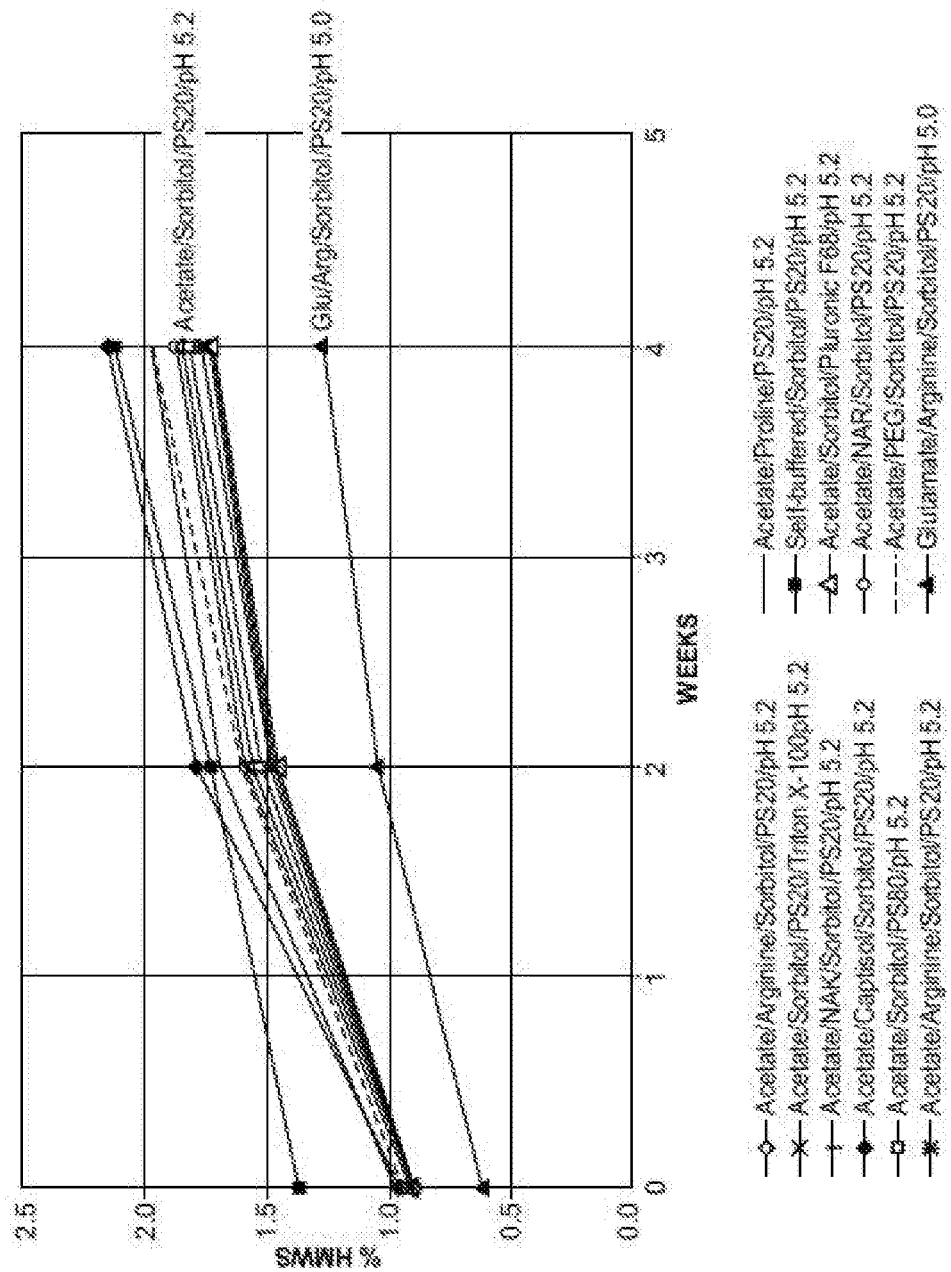
FIGS. 1, 2, and 8 show the percent HMWS monitored by SE-UHPLC as a function of formulation and time at 37° C. for various high-concentration denosumab formulations. The legend of FIG. 1 accords to the formulation having the Abbreviation shown in Table 1. The legend of FIG. 8 accords to the letter shown in Table 5.

It would be desirable to provide a more concentrated aqueous solution of denosumab, and other human anti-RANKL antibodies, and antigen-binding portions thereof, that are as stable as, or more stable than, dilute solutions. The more concentrated solution could provide patient convenience, for example by allowing administration of a smaller volume, such as 1 mL injection, to deliver 120 mg of active, such as denosumab, rather than a 1.7 mL or 2 mL injection of a more dilute active formulation. Still further, it would allow an even smaller volume of injection solution to deliver a lower dose of active, e.g. 0.5 mL of 120 mg/mL concentration denosumab to deliver a 60 mg dose. It would also be desirable to provide aqueous solution of denosumab, and other human anti-RANKL antibodies, and antigen-binding portions thereof, that are more stable than prior-known solutions. The stable, concentrated formulation will also have other benefits, such as allowing handling and shipment of lower volumes of product, and allowing longer shelf lives of products.

Aggregates in biologic products can differ in origin, size, and type. Aggregates that can affect a biologic product's efficacy or safety are of particular concern, e.g. aggregates that can enhance immune responses and cause adverse clinical effects. High molecular weight aggregates, aka High Molecular Weight Species (HMWS), particularly those that conserve most of the native configuration of the monomer counterpart, can be of particular concern. Aggregation can also potentially affect the subcutaneous bioavailability and pharmacokinetics of a therapeutic protein.

Aggregate formation can have various causes. Generally, protein aggregation results from conformational instability, which is the result of protein structural changes, and colloidal instability, which is dominated by intermolecular forces. In the case where a critical nucleation event is required to induce precipitation, the kinetics of protein aggregation can be characterized by inclusion of a lag time phase.

Aggregation due to conformational instability involves unfolding and association steps. Unfolding of the protein molecule exposes hydrophobic amino acid residues. The hydrophobic residues of the unfolded molecules can then undergo association, which leads to aggregation (e.g. as dimers, trimers, other multimers, and higher order aggregates). Such associations are concentration-dependent. An increase in protein concentration in an aqueous solvent generally increases the rate and extent of aggregation, including thermally-induced aggregation. Thus, additives which affect the free energy of protein unfolding in solution can affect conformational stability.

Colloidal instability results in aggregates via protein-protein intramolecular association forces. Such forces can be affected by one or more factors including ionic strength, solution pH, and types of buffers.

Denosumab is commercially available in solution forms at strengths of 60 mg/mL and 70 mg/mL. Attempts to formulate higher concentration solutions of denosumab using the same excipients showed that the higher concentration affected stability of the product, via a concomitant and proportional increase in HMWS. For example, a concentration of 120 mg/mL denosumab has a concentration more than 70% higher than 70 mg/mL denosumab, and is double the 60 mg/mL concentration.

Accordingly, a stabilized aqueous formulation according to the present disclosure will resist aggregate formation to a greater extent than previously-known formulations. One aspect of the disclosure is a stabilized aqueous formulation characterized by a pH of 5.0 to less than 5.2. Another nonexclusive aspect of the disclosure is a stabilized aqueous formulation including an amino acid aggregation inhibitor. Also provided are related dosage presentations, e.g. as single-use vials, syringes, and glass containers, and related methods of treatment. Methods of making stable, aqueous pharmaceutical formulations are additionally provided.

As described below, the pH and amino acid aggregation inhibitor (e.g., arginine, arginine-arginine dipeptide, arginine-phenylalanine dipeptide) are two levers shown to reduce the level of HMWS and rate of HMWS formation of denosumab at 120 mg/mL. HMWS can be described as intermolecular protein interactions that are either irreversible (e.g. covalent) or reversible (e.g. non-covalent self-associated interactions). There are four well-accepted causes for protein self-association reactions that can lead to increases in viscosity and HMWS; hydrophobic, charged, polar, and dipole interactions. Both formulation pH and arginine (a highly charged basic amino acid at neutral to acidic pH values) can interfere with charged protein intermolecular forces. Without intending to be bound by any particular theory, it is conceivable that HMWS formation of denosumab at 120 mg/mL is based on protein charge, and these formulation changes are disrupting the charge forces involved in the mechanism of HMWS formation. Further without intending to be bound by any particular theory, it is conceivable that there could also be hydrophobic protein self-association interactions in the formation of HMWS, since arginine contains a short aliphatic chain of hydrocarbons in the side chain. This aliphatic chain can disrupt hydrophobic interactions between proteins. This idea is further supported by the inclusion of phenylalanine in the formulation to have an additional reduction in the levels of HMWS. Without being bound to any particular theory, arginine stabilizes the anti-RANKL antibody in a manner different from that of phenylalanine, such that, if arginine interacts with the antibody via hydrophobic interactions, arginine may interact with the antibody in one or more other ways.

Other excipients that can have a potentially positive impact on reduction of HMWS level and rate of formation can have a similar positively charged group at neutral to acidic pH values when compared to arginine, and/or can be hydrophobic in nature similar to phenylalanine. Examples of these excipients can include lysine, N-acetyl arginine, N-acetyl lysine, tyrosine, tryptophan, and leucine.

The formulations, dosage presentations, and methods are contemplated to include embodiments including any combination of one or more of the additional optional elements, features, and steps further described below (including those shown in the figures), unless stated otherwise.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "comprising" indicates the potential inclusion of other agents, elements, steps, or features, in addition to those specified.

It should be understood that every maximum numerical limitation given throughout this specification includes as alternative aspects ranges formed with every corresponding lower numerical limitation, as if such ranges were expressly written. Every minimum numerical limitation given throughout this specification will include as alternative aspects ranges formed with every higher numerical limitation, as if such ranges were expressly written. Every numerical range given throughout this specification will include every narrower numerical range that falls within such broader numerical range, as if such narrower numerical ranges were all expressly written herein. The dimensions and values disclosed herein should be understood to include disclosure of both the recited value and the corresponding exact numerical, e.g. a value described as "about 10 mM" should be understood to include, as an alternative disclosure, "10 mM."

The terms "therapeutically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, or reduction in symptoms. The precise effective amount for a subject will depend upon the subject's body weight, size, and health; the nature and extent of the condition; and the therapeutic or combination of therapeutics selected for administration. Where a drug has been approved by the U.S. Food and Drug Administration (FDA), a "therapeutically effective amount" refers to the dosage approved by the FDA or its counterpart foreign agency for treatment of the identified disease or condition.

The present disclosure provides stabilized (or stable) aqueous pharmaceutical formulations as demonstrated by the reduced amounts of aggregates and/or reduced aggregate formation rates following storage. As described herein, the stability of such formulations is shown by the reduced amounts of HMWS and/or reduced HMWS formation rates following storage for varied time periods and at varied temperatures. In general, higher stability formulations are associated with lower amounts of HMWS, lower HMWS formation rates, and/or higher antibody main peaks at higher storage temperatures, relative to lower temperatures. As used herein, the term "high molecular weight species" or "HMWS" refers to higher order aggregates of the antibody of the formulations, as well as lower order aggregates of the antibody of the formulations. Lower order aggregates, include, for example, dimer species. The aggregate amounts and rates of formation may be measured or monitored by techniques, such as, e.g., SE-UHPLC. SE-UHPLC chromatograms of the antibody, in some instances, show a peak around 5.8 minutes representing the amount of HMWS of the aqueous pharmaceutical formulation, a peak around 6.7 minutes representing the dimer species, and a peak around 8.0 minutes reflecting the amount of intact, non-aggregated forms of the antibody. Relative to storage at 4° C., storage at 37° C. allows for the acceleration of a stability assay such that the stability of a particular formulation may be determined in a shorter period of time, relative to the storage time period at 4° C. For example, storage at 37° C. for 1, 2, or 3 months may be indicative or predictive of storage at 4° C. for 36 months.

In one type of embodiment, a stabilized formulation as described herein will show a reduced extent and rate of formation of HMWS following 3 months of storage at 37° C., as compared to an equivalent-concentration control formulation consisting of 10 mM acetate, 5% (w/v) sorbitol, 0.01% (w/v) polysorbate 20 as excipients and having a solution pH of 5.2.

In another type of embodiment, a stabilized formulation as described herein and including an amino acid aggregation inhibitor will show a reduced extent of formation of HWMS following 1 month of storage at 37° C., as compared to an equivalent control formulation without the amino acid aggregation inhibitor. For example, the extent of formation can be reduced such that the % amount of HMWS by SE-UPHLC is lower by at least about 0.1%, or about 0.2%, or about 0.3%, or about 0.4%, or about 0.5%, or about 0.6%, or about 0.7%, for example in a range of about 0.1% to about 2%, or about 0.1% to about 1%, compared to the control formulation following 1 month of storage at 37° C.

In another type of embodiment a stabilized formulation as described herein will have a low amount of HMWS following 1 month storage at 37° C., by SE-UHPLC. For example, the amount of HMWS can be not more than 2%, or less than 2%, or not more than 1.9%, or less than 1.9%, or not more than 1.8%, or less than 1.8%, or not more than 1.7%, or less than 1.7%, or not more than 1.6%, or less than 1.6%, or not more than 1.5%, or less than 1.5%, or not more than 1.4%, or less than 1.4%, or not more than 1.3%, or less than 1.3%, or not more than 1.2%, or less than 1.2%, for example in a range of about 0.01% to about 2%, or about 0.01% to about 1.9%, or about 0.01% to about 1.8%, or about 0.01% to about 1.7%, or about 0.01% to about 1.6%, or about 0.01% to about 1.5%, or about 0.01% to about 1.4%, or about 0.01% to about 1.3%, or about 0.01% to about 1.2%. In another type of embodiment, the amount of HMWS following 1 month storage at 37° C., by SE-UHPLC can be greater than 2%, e.g. greater than 2% and up to 3%, while the reduced rate of aggregation provided by the amino acid aggregation inhibitor will allow for a suitable product shelf life, e.g. up to three years, or up to two years.

In another type of embodiment a stabilized formulation as described herein will have a low amount of HMWS following 3 months storage at 37° C., by SE-UHPLC. For example, the amount of HMWS can be not more than 2%, or less than 2%, or not more than 1.9%, or less than 1.9%, or not more than 1.8%, or less than 1.8%, or not more than 1.7%, or less than 1.7%, or not more than 1.6%, or less than 1.6%, or not more than 1.5%, or less than 1.5%, or not more than 1.4%, or less than 1.4%, or not more than 1.3%, or less than 1.3%, or not more than 1.2%, or less than 1.2%, for example in a range of about 0.01% to about 2%, or about 0.01% to about 1.9%, or about 0.01% to about 1.8%, or about 0.01% to about 1.7%, or about 0.01% to about 1.6%, or about 0.01% to about 1.5%, or about 0.01% to about 1.4%, or about 0.01% to about 1.3%, or about 0.01% to about 1.2%.

In another type of embodiment a stabilized formulation as described herein will have a low amount of HMWS following 36 months storage at 4° C., by SE-UHPLC. For example, the amount of HMWS can be not more than 2%, or less than 2%, or not more than 1.9%, or less than 1.9%, or not more than 1.8%, or less than 1.8%, or not more than 1.7%, or less than 1.7%, or not more than 1.6%, or less than 1.6%, or not more than 1.5%, or less than 1.5%, or not more than 1.4%, or less than 1.4%, or not more than 1.3%, or less than 1.3%, or not more than 1.2%, or less than 1.2%, for example in a range of about 0.01% to about 2%, or about 0.01% to about 1.9%, or about 0.01% to about 1.8%, or about 0.01% to about 1.7%, or about 0.01% to about 1.6%, or about 0.01% to about 1.5%, or about 0.01% to about 1.4%, or about 0.01% to about 1.3%, or about 0.01% to about 1.2%.

In another type of embodiment a stabilized formulation as described herein will have a high amount of the denosumab or other antibody (or antigen-binding portion thereof) main peak following 1 month storage at 37° C., by SE-UHPLC. For example, the amount of the main peak can be at least 95%, or greater than 95%, or at least 96%, or greater than 96%, or at least 97%, or greater than 97%, or at least 97.5%, or greater than 97.5%, or at least 98%, or greater than 98%, or at least 98.1%, or greater than 98.1%, or at least 98.2%, or greater than 98.2%, or at least 98.3%, or greater than 98.3%, or at least 98.4%, or greater than 98.4%, or at least 98.5%, or greater than 98.5%, or at least 98.6%, or greater than 98.6%, for example in a range of about 95% to about 99.9%, or about 96% to about 99.9%, or about 97% to about 99.9%, or about 97.5% to about 99.9%, or about 98% to about 99.9%, or about 98.1% to about 99.9%, or about 98.2% to about 99.9%, or about 98.3% to about 99.9%, or about 98.4% to about 99.9%, or about 98.5% to about 99.9%, or about 98.6% to about 99.9%.

In another type of embodiment a stabilized formulation as described herein will have a high amount of the denosumab or other antibody (or antigen-binding portion thereof) main peak following 3 months storage at 37° C., by SE-UHPLC. For example, the amount of the main peak can be at least 95%, or greater than 95%, or at least 96%, or greater than 96%, or at least 97%, or greater than 97%, or at least 97.5%, or greater than 97.5%, or at least 98%, or greater than 98%, or at least 98.1%, or greater than 98.1%, or at least 98.2%, or greater than 98.2%, or at least 98.3%, or greater than 98.3%, or at least 98.4%, or greater than 98.4%, or at least 98.5%, or greater than 98.5%, or at least 98.6%, or greater than 98.6%, for example in a range of about 95% to about 99.9%, or about 96% to about 99.9%, or about 97% to about 99.9%, or about 97.5% to about 99.9%, or about 98% to about 99.9%, or about 98.1% to about 99.9%, or about 98.2% to about 99.9%, or about 98.3% to about 99.9%, or about 98.4% to about 99.9%, or about 98.5% to about 99.9%, or about 98.6% to about 99.9%.

In another type of embodiment a stabilized formulation as described herein will have a high amount of the denosumab or other antibody (or antigen-binding portion thereof) main peak following 36 months storage at 4° C., by SE-UHPLC. For example, the amount of the main peak can be at least 95%, or greater than 95%, or at least 96%, or greater than 96%, or at least 97%, or greater than 97%, or at least 97.5%, or greater than 97.5%, or at least 98%, or greater than 98%, or at least 98.1%, or greater than 98.1%, or at least 98.2%, or greater than 98.2%, or at least 98.3%, or greater than 98.3%, or at least 98.4%, or greater than 98.4%, or at least 98.5%, or greater than 98.5%, or at least 98.6%, or greater than 98.6%, for example in a range of about 95% to about 99.9%, or about 96% to about 99.9%, or about 97% to about 99.9%, or about 97.5% to about 99.9%, or about 98% to about 99.9%, or about 98.1% to about 99.9%, or about 98.2% to about 99.9%, or about 98.3% to about 99.9%, or about 98.4% to about 99.9%, or about 98.5% to about 99.9%, or about 98.6% to about 99.9%.

In further embodiments, it is contemplated that the stabilized formulation will have both a low amount of HMWS and a high amount of main peak, according to a specification described above, following storage.

In exemplary aspects, the aqueous pharmaceutical formulations comprise not more than about 4% high molecular weight species (HMWS) and/or comprise more than about 96% of the antibody main peak, as measured by SE-UHPLC, following storage. In exemplary aspects, the aqueous pharmaceutical formulations comprise not more than about 3% high molecular weight species (HMWS) and/or comprise more than about 97% of the antibody main peak, as measured by SE-UHPLC, following storage. In exemplary aspects, the aqueous pharmaceutical formulations comprise less than about 2% HMWS and/or more than about 98% of the antibody main peak, as measured by SE-UHPLC, following storage. In exemplary aspects, the storage is at a temperature of about 2° C. to about 8° C. (e.g., about 2° C., about 3° C., about 4° C., about 5° C., about 6° C., about 7° C., about 8° C.) for at least 12 months, 24 months, or 36 months (e.g., at least or about 12 months, at least or about 16 months, at least or about 20 months, at least or about 24 months, at least or about 28 months, at least or about 32 months, at least or about 36 months, optionally, longer). In exemplary aspects, the storage is at about 20° C. to about 30° C. (e.g., about 21° C. to about 30° C., about 22° C. to about 30° C., about 23° C. to about 30° C., about 24° C. to about 30° C., about 25° C. to about 30° C., about 26° C. to about 30° C., about 27° C. to about 30° C., about 28° C. to about 30° C., about 28° C. to about 30° C., about 20° C. to about 29° C., about 20° C. to about 28° C., about 20° C. to about 27° C., about 20° C. to about 26° C., about 20° C. to about 25° C., about 20° C. to about 24° C., about 20° C. to about 23° C., about 20° C. to about 22° C.) for about 1 month (e.g., about 26 days, about 27 days, about 28 days, about 29 days, about 30 days, about 31 days, about 32 days, about 33 days, about 34 days, about 35 days, about 36 days). In exemplary aspects, the storage comprises a first storage followed by a second storage and the first storage is at about 2° C. to about 8° C. for at least 12 months, 24 months, or 36 months and the second storage is at about 20° C. to about 30° C. for about 1 month. In exemplary instances, the aqueous pharmaceutical formulations comprise not more than 2% HMWS, or less than 2% HMWS, or not more than 1.9% HMWS, or less than 1.9% HMWS, or not more than 1.8% HMWS, or less than 1.8% HMWS, or not more than 1.7% HMWS, or less than 1.7% HMWS, or not more than 1.6% HMWS, or less than 1.6% HMWS, or not more than 1.5% HMWS, or less than 1.5% HMWS, or not more than 1.4% HMWS, or less than 1.4% HMWS, or not more than 1.3% HMWS, or less than 1.3% HMWS, or not more than 1.2% HMWS, or less than 1.2% HMWS, for example in a range of about 0.01% to about 2% HMWS, or about 0.01% to about 1.9% HMWS, or about 0.01% to about 1.8% HMWS, or about 0.01% to about 1.7% HMWS, or about 0.01% to about 1.6% HMWS, or about 0.01% to about 1.5% HMWS, or about 0.01% to about 1.4% HMWS, or about 0.01% to about 1.3% HMWS, or about 0.01% to about 1.2% HMWS, optionally, as measured by SE-UHPLC. In alternative or additional aspects, the aqueous pharmaceutical formulations comprise more than 98% of the antibody main peak, or at least 95% antibody main peak, or greater than 95% antibody main peak, or at least 96% antibody main peak, or greater than 96% antibody main peak, or at least 97% antibody main peak, or greater than 97% antibody main peak, or at least 97.5% antibody main peak, or greater than 97.5% antibody main peak, or at least 98% antibody main peak, or greater than 98% antibody main peak, or at least 98.1% antibody main peak, or greater than 98.1% antibody main peak, or at least 98.2% antibody main peak, or greater than 98.2% antibody main peak, or at least 98.3% antibody main peak, or greater than 98.3% antibody main peak, or at least 98.4% antibody main peak, or greater than 98.4% antibody main peak, or at least 98.5% antibody main peak, or greater than 98.5% antibody main peak, or at least 98.6% antibody main peak, or greater than 98.6% antibody main peak, for example in a range of about 95% to about 99.9% antibody main peak, or about 96% to about 99.9% antibody main peak, or about 97% to about 99.9% antibody main peak, or about 97.5% to about 99.9% antibody main peak, or about 98% to about 99.9% antibody main peak, or about 98.1% to about 99.9% antibody main peak, or about 98.2% to about 99.9% antibody main peak, or about 98.3% to about 99.9% antibody main peak, or about 98.4% to about 99.9% antibody main peak, or about 98.5% to about 99.9% antibody main peak, or about 98.6% to about 99.9% antibody main peak, optionally, as measured by SE-UHPLC.

As used herein, the term "antibody" refers to a protein having a conventional immunoglobulin format, comprising heavy and light chains, and comprising variable and constant regions. For example, an antibody may be an IgG which is a "Y-shaped" structure of two identical pairs of polypeptide chains, each pair having one "light" (typically having a molecular weight of about 25 kDa) and one "heavy" chain (typically having a molecular weight of about 50-70 kDa). An antibody has a variable region and a constant region. In IgG formats, the variable region is generally about 100-110 or more amino acids, comprises three complementarity determining regions (CDRs), is primarily responsible for antigen recognition, and substantially varies among other antibodies that bind to different antigens. See, e.g., Janeway et al., "Structure of the Antibody Molecule and the Immunoglobulin Genes", Immunobiology: The Immune System in Health and Disease, $4^{th}$ ed. Elsevier Science Ltd./Garland Publishing, (1999).

Briefly, in an antibody scaffold, the CDRs are embedded within a framework in the heavy and light chain variable region where they constitute the regions largely responsible for antigen binding and recognition. A variable region comprises at least three heavy chain CDRs or three light chain CDRs (Kabat et al., 1991, Sequences of Proteins of Immunological Interest, Public Health Service N.I.H., Bethesda, Md.; see also Chothia and Lesk, 1987, J. Mol. Biol. 196: 901-917; Chothia et al., 1989, Nature 342: 877-883), within a framework region (designated framework regions 1-4, FR1, FR2, FR3, and FR4, by Kabat et al., 1991; see also Chothia and Lesk, 1987, supra).

Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2. Embodiments of the disclosure include all such classes or isotypes of antibodies. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. Accordingly, in exemplary embodiments, the antibody is an antibody of isotype IgA, IgD, IgE, IgG, or IgM, including any one of IgG1, IgG2, IgG3 or IgG4. In exemplary aspects, the anti-RANKL antibody is an IgG1, IgG2, or IgG4 antibody.

In various aspects, the antibody can be a monoclonal antibody or a polyclonal antibody. In some aspects, the antibody comprises a sequence that is substantially similar to a naturally-occurring antibody produced by a mammal, e.g., mouse, rat, rabbit, goat, horse, chicken, hamster, pig, human, and the like. In this regard, the antibody may be considered as a mammalian antibody, e.g., a mouse antibody, rat antibody, rabbit antibody, goat antibody, horse antibody, chicken antibody, hamster antibody, pig antibody, human antibody, and the like. In certain aspects, the anti-RANKL antibody is a monoclonal human antibody. In certain aspects, the recombinant protein is a chimeric antibody or a humanized antibody. The term "chimeric antibody" is used herein to refer to an antibody containing constant domains from one species and the variable domains from a second, or more generally, containing stretches of amino acid sequence from at least two species. The term "humanized" when used in relation to antibodies refers to antibodies having at least CDR regions from a non-human source which are engineered to have a structure and immunological function more similar to true human antibodies than the original source antibodies. For example, humanizing can involve grafting CDR from a non-human antibody, such as a mouse antibody, into a human antibody. Humanizing also can involve select amino acid substitutions to make a non-human sequence look more like a human sequence.

An antibody, in various aspects, is cleaved into fragments by enzymes, such as, e.g., papain and pepsin. Papain cleaves an antibody to produce two Fab fragments and a single Fc fragment. Pepsin cleaves an antibody to produce a F(ab')$_2$ fragment and a pFc' fragment. In exemplary aspects, the aqueous pharmaceutical formulation comprises an antibody fragment, e.g., a Fab, Fc, F(ab')$_2$, or a pFc', that retains at least one antigen (RANKL) binding site. With regard to the aqueous pharmaceutical formulations and methods of the present disclosure, the antibody may lack certain portions of an antibody, and may be an antibody fragment which binds to RANKL. In exemplary aspects, the antibody fragment is an antigen-binding portion of an anti-RANKL antibody.

Antibody protein products can be an antigen binding format based on antibody fragments, e.g., scFvs, Fabs and VHH/VH, which retain full antigen-binding capacity. The smallest antigen-binding fragment that retains its complete antigen binding site is the Fv fragment, which consists entirely of variable (V) regions. A soluble, flexible amino acid peptide linker is used to connect the V regions to a scFv (single chain fragment variable) fragment for stabilization of the molecule, or the constant (C) domains are added to the V regions to generate a Fab fragment [fragment, antigen-binding]. Both scFv and Fab are widely used fragments that can be easily produced in hosts, e.g., prokaryotic hosts. Other antibody protein products include disulfide-bond stabilized scFv (ds-scFv), single chain Fab (scFab), as well as di- and multimeric antibody formats like dia-, tria- and tetra-bodies, or minibodies (miniAbs) that comprise different formats consisting of scFvs linked to oligomerization domains. The smallest fragments are VHH/VH of camelid heavy chain Abs as well as single domain Abs (sdAb). The building block that is most frequently used to create novel antibody formats is the single-chain variable (V)-domain antibody fragment (scFv), which comprises V domains from the heavy and light chain (VH and VL domain) linked by a peptide linker of ~15 amino acid residues. A peptibody or peptide-Fc fusion is yet another antibody protein product. The structure of a peptibody consists of a biologically active peptide grafted onto an Fc domain. Peptibodies are well-described in the art. See, e.g., Shimamoto et al., mAbs 4(5): 586-591 (2012).

Other antibody protein products include a single chain antibody (SCA); a diabody; a triabody; a tetrabody; bispecific or trispecific antibodies, and the like. Bispecific antibodies can be divided into five major classes: BsIgG, appended IgG, BsAb fragments, bispecific fusion proteins and BsAb conjugates. See, e.g., Spiess et al., Molecular Immunology 67(2) Part A: 97-106 (2015).

In exemplary aspects, the anti-RANKL antibody, or antigen binding portion thereof, comprises, consists essentially of, or consists of any one of these antibody protein products (e.g., scFv, Fab VHH/VH, Fv fragment, ds-scFv, scFab, dimeric antibody, multimeric antibody (e.g., a diabody, triabody, tetrabody), miniAb, peptibody VHH/VH of camelid heavy chain antibody, sdAb, diabody; a triabody; a tetrabody; a bispecific or trispecific antibody, BsIgG, appended IgG, BsAb fragment, bispecific fusion protein, and BsAb conjugate).

In exemplary aspects, the anti-RANKL antibody, or antigen binding portion thereof, comprises, consists essentially of, or consists of an antibody protein product in monomeric form, or polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

A human anti-human receptor activator of nuclear factor kappa-B ligand (anti-RANKL) antibody or an antigen-binding portion thereof for use in the formulation is an antibody or an antigen-binding portion thereof that specifically binds human RANKL protein or human osteoprotegrin (OPGL) protein of a fragment thereof and inhibits or neutralizes the activity of RANKL or OPGL protein and/or inhibits RANK/RANKL signaling pathway, and is referred to herein as a human anti-RANKL monoclonal antibody or an antigen-binding portion thereof. For example, the formulations described herein can comprise a human anti-RANKL monoclonal antibody that specifically binds to the amino acid sequence of human RANKL (SEQ ID NO: 12) or a portion thereof. The human RANKL protein is a transmembrane or soluble protein that is encoded by the polynucleotide sequence of SEQ ID NO: 11, which is known to be essential for the formation, function and survival of osteoclasts. For example, human anti-RANKL antibodies inhibit the interaction of RANKL with its receptor RANK.

An example of a human anti-RANKL monoclonal antibody is denosumab, which is sold in commercial form as Xgeva® and Prolia®. Xgeva® is a 120 mg dose formulation of denosumab in 1.7 mL solution (70 mg/mL) in a single-use vial, containing 120 mg denosumab, acetate (18 mM), sorbitol (4.6%), Water for Injection (USP), and sodium hydroxide to a pH of 5.2. Prolia® is available as 60 mg dose formulations of denosumab in 1 mL solution (60 mg/mL). Each 1 mL single-use prefilled syringe of Prolia® contains 60 mg denosumab (60 mg/mL solution), 4.7% sorbitol, 17 mM acetate, 0.01% polysorbate 20, Water for Injection (USP), and sodium hydroxide to a pH of 5.2. Formulations as described herein, and including denosumab or a portion thereof, are specifically contemplated. Denosumab is a fully human IgG2 monoclonal antibody that binds to human RANKL. Denosumab has an approximate molecular weight of 147 kDa and is expressed in the Chinese hamster ovary (CHO) cell line. The amino acid sequences of the denosumab variable light chain (LC) and variable heavy chain (HC) are set out at SEQ ID NO: 1 and 2, respectively and the full length LC and HC are set out as SEQ ID NO: 3 and 4; respectively. A nucleic acid comprising a nucleotide sequence encoding the amino acid sequence of SEQ ID NO: 1 (the denosumab variable LC) is, in some aspects, a nucleic acid of SEQ ID NO: 19. A nucleic acid comprising a nucleotide sequence encoding the amino acid sequence of SEQ ID NO: 2 (the denosumab variable HC) is, in some aspects, a nucleic acid of SEQ ID NO: 20. A nucleic acid comprising a nucleotide sequence encoding the amino acid sequence of SEQ ID NO: 3 (the full length denosumab LC) is, in some aspects, a nucleic acid of SEQ ID NO: 21. A nucleic acid comprising a nucleotide sequence encoding the amino acid sequence of SEQ ID NO: 4 (the full length denosumab HC) is, in some aspects, a nucleic acid of SEQ ID NO: 23. The mature form of the LC, which is represented as amino acids 21-235 of the full length LC, is set out as SEQ ID NO: 13, while the mature form of the HC, which is represented as amino acids 20-467 of the full length HC, is set out as SEQ ID NO: 14. A nucleic acid comprising a nucleotide sequence encoding the amino acid sequence of SEQ ID NO: 13 (the mature form of the LC) is, in some aspects, a nucleic acid of SEQ ID NO: 22. A nucleic acid comprising a nucleotide sequence encoding the amino acid sequence of SEQ ID NO: 14 (the mature form of the HC) is, in some aspects, a nucleic acid of SEQ ID NO: 24. In addition, the denosumab LC CDRs are set out as SEQ ID NO: 5 (LC CDR1), SEQ ID NO: 6 (LC CDR2) and SEQ ID NO: 7 (LC CDR3). Denosumab HC CDRs are set out as SEQ ID NO: 8 (HC CDR1), SEQ ID No: 9 (HC CDR2), and SEQ ID NO: 10 (HC CDR3). Denosumab has been described and claimed in International Patent Application No. WO 03/002713 and U.S. Pat. No. 7,364,736, the disclosures of which are hereby incorporated by reference in their entireties.

As used herein, the term "denosumab" includes biosimilars of denosumab. As used herein, "biosimilar" (of an approved reference product/biological drug, such as a protein therapeutic, antibody, etc.) refers to a biologic product that is similar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan. A biosimilar can be, for example, an antibody having the same primary amino acid sequence as a marketed antibody, but may be made in different cell types or by different production, purification or formulation methods.

The formulations can comprise a human anti-RANKL antibody comprising at least one of the amino acid sequences of SEQ ID NOS: 1-4, 13, 14, or a portion thereof. The formulations can comprise a human anti-RANKL antibody comprising at least one of the CDR amino acid sequences set out as SEQ ID NO: 5, SEQ ID NO: 6, SEQ ID NO: 7, SEQ ID NO: 8, SEQ ID NO: 9 or SEQ ID NO: 10, or at least two of the CDR amino acid sequences set out as SEQ ID NO: 5, SEQ ID NO: 6, SEQ ID NO: 7, SEQ ID NO: 8, SEQ ID NO: 9 or SEQ ID NO: 10, or at least three of the CDR amino acid sequences set out as SEQ ID NO: 5, SEQ ID NO: 6, SEQ ID NO: 7, SEQ ID NO: 8, SEQ ID NO: 9 or SEQ ID NO: 10, or at least four of the CDR amino acid sequences set out as SEQ ID NO: 5, SEQ ID NO: 6, SEQ ID NO: 7, SEQ ID NO: 8, SEQ ID NO: 9 or SEQ ID NO: 10, or at least five of the CDR amino acid sequences set out as SEQ ID NO: 5, SEQ ID NO: 6, SEQ ID NO: 7, SEQ ID NO: 8, SEQ ID NO: 9 or SEQ ID NO: 10, or at least six of the CDR amino acid sequences set out as SEQ ID NO: 5, SEQ ID NO: 6, SEQ ID NO: 7, SEQ ID NO: 8, SEQ ID NO: 9 or SEQ ID NO: 10.

The formulations can comprise a human anti-RANKL antibody comprising at least one amino acid sequence that is at least 80% identical to any one of SEQ ID NO: 1-4, 13, and 14 and inhibits the interaction between RANKL and its receptor, RANK, or a human anti-RANKL antibody comprising at least one amino acid sequence that is at least 85% identical to any one of SEQ ID NO: 1-4, 13, and 14 and inhibits the interaction between RANKL and its receptor, RANK, or a human anti-RANKL antibody comprising at least one amino acid sequence that is at least 90% identical to any one of SEQ ID NO: 1-4, 13, and 14 and inhibits the interaction between RANKL and its receptor, RANK, or a human anti-RANKL antibody comprising at least one amino acid sequence that is at least 91% identical to any one of SEQ ID NO: 1-4, 13, and 14 and inhibits the interaction between RANKL and its receptor, RANK, or a human anti-RANKL antibody comprising at least one amino acid sequence that is at least 92% identical to any one of SEQ ID NO: 1-4, 13, and 14 and inhibits the interaction between RANKL and its receptor, RANK, or a human anti-RANKL antibody comprising at least one amino acid sequence that is at least 93% identical to any one of SEQ ID NO: 1-4, 13, and 14 and inhibits the interaction between RANKL and its receptor, RANK, or a human anti-RANKL antibody comprising at least one amino acid sequence that is at least 94% identical to any one of SEQ ID NO: 1-4, 13, and 14 and inhibits the interaction between RANKL and its receptor, RANK, or a human anti-RANKL antibody comprising at least one amino acid sequence that is at least 95% identical to any one of SEQ ID NO: 1-4, 13, and 14 and inhibits the interaction between RANKL and its receptor, RANK, or a human anti-RANKL antibody comprising at least one amino acid sequence that is at least 96% identical to any one of SEQ ID NO: 1-4, 13, and 14 and inhibits the interaction between RANKL and its receptor, RANK, or a human anti-RANKL antibody comprising at least one amino acid sequence that is at least 97% identical to any one of SEQ ID NO: 1-4, 13, and 14 and inhibits the interaction between RANKL and its receptor, RANK, or a human anti-RANKL antibody comprising at least one amino acid sequence that is at least 98% identical to any one of SEQ ID NO: 1-4, 13, and 14 and inhibits the interaction between RANKL and its receptor, RANK, or a human anti-RANKL antibody comprising at least one amino acid sequence that is at least 99% identical to any one of SEQ ID NO: 1-4, 13, and 14 and inhibits the interaction between RANKL and its receptor, RANK.

In exemplary embodiments, the aqueous pharmaceutical formulation comprises an anti-RANKL antibody, or an antigen-binding portion thereof, including, an antibody protein product, as described herein. In exemplary aspects, the anti-RANKL antibody, or antigen-binding portion thereof, comprises a light chain variable domain comprising a light chain CDR1 sequence comprising the amino acid sequence set forth in SEQ ID NO: 5. In alternative or additional instances, the anti-RANKL antibody, or antigen-binding portion thereof, comprises a light chain variable domain comprising a light chain CDR2 sequence comprising the amino acid sequence set forth in SEQ ID NO: 6. In alternative or additional aspects, the anti-RANKL antibody, or antigen-binding portion thereof, comprises a heavy chain variable domain comprising a heavy chain CDR3 sequence comprising the amino acid sequence set forth in SEQ ID NO: 10. In some instances, the anti-RANKL antibody, or antigen-binding portion thereof, comprises a SEQ ID NO: 5, SEQ ID NO: 6, and SEQ ID NO: 10. In exemplary aspects, the anti-RANKL antibody, or antigen-binding portion thereof, comprises (i) a light chain variable domain comprising a light chain CDR3 sequence comprising the amino acid sequence set forth in SEQ ID NO:7; (ii) a heavy chain variable domain comprising a heavy chain CDR1 sequence comprising the amino acid sequence set forth in SEQ ID NO: 8, optionally, SEQ ID NO: 27; (iii) a heavy chain variable domain comprising a heavy chain CDR2 sequence comprising the amino acid sequence set forth in SEQ ID NO: 9, or (iv) any combination thereof. In some aspects, the anti-RANKL antibody, or antigen-binding portion thereof, comprises (A) a light chain variable domain comprising a light chain CDR1 comprising the amino acid sequence of SEQ ID NO: 5, a light chain variable domain comprising a light chain CDR2 comprising the amino acid sequence of SEQ ID NO: 6, and a light chain variable domain comprising a light chain CDR3 comprising the amino acid sequence of SEQ ID NO:7; and (B) a heavy chain variable domain comprising a heavy chain CDR1 comprising the amino acid sequence of SEQ ID NO: 8 (optionally, SEQ ID N: 27), a heavy chain variable domain comprising a heavy chain CDR2 comprising the amino acid sequence of SEQ ID NO: 9, and a heavy chain variable domain comprising a heavy chain CDR3 comprising the amino acid sequence of SEQ ID NO: 10. In exemplary aspects, the anti-RANKL antibody, or antigen-binding portion thereof, comprises: (A) a light chain variable domain selected from the group consisting of: (i) a light chain variable domain comprising an amino acid sequence that is at least 80% (e.g., at least 85%, at least 90%, at least 91%, at least 92%, at least 93%, at least 94%, at least 95%, at least 96%, at least 97%, at least 98%, at least 99%) identical to SEQ ID NO: 1; (ii) a light chain variable domain comprising an amino acid sequence encoded by a polynucleotide sequence comprising SEQ ID NO: 19; and (iii) a light chain variable domain comprising an amino acid sequence encoded by a polynucleotide that hybridizes under stringent conditions to the complement of a polynucleotide consisting of SEQ ID NO: 19; or (B) the heavy chain variable domain selected from the group consisting of: (i) a heavy chain variable domain comprising an amino acid sequence that is at least 80% (e.g., at least 85%, at least 90%, at least 91%, at least 92%, at least 93%, at least 94%, at least 95%, at least 96%, at least 97%, at least 98%, at least 99%) identical to SEQ ID NO: 2; (ii) a heavy chain variable domain comprising an amino acid sequence encoded by a polynucleotide sequence comprising SEQ ID NO: 20, and (iii) a heavy chain variable domain comprising an amino acid sequence encoded by a polynucleotide that hybridizes under stringent conditions to the complement of a polynucleotide consisting of SEQ ID NO: 20; or (C) a light chain variable domain of (A) and a heavy chain variable domain of (B). In exemplary aspects, the anti-RANKL antibody is a fully human antibody, a humanized antibody, or a chimeric antibody. In exemplary instances, the antigen-binding portion is an a Fab, Fab', F(ab')2, or a single chain Fv. In exemplary aspects, the anti-RANKL antibody is an $IgG_1$, $IgG_2$, or $IgG_4$ antibody, optionally, wherein the anti-RANKL antibody comprises a sequence of SEQ ID NO: 15. In some aspects, the anti-RANKL antibody comprises a sequence of SEQ ID NO: 16, SEQ ID NO: 17, or SEQ ID NO: 18. In exemplary aspects, the anti-RANKL antibody, or antigen-binding portion thereof, comprises: (A) a light chain selected from the group consisting of: (i) a light chain comprising an amino acid sequence that is at least 80% (e.g., at least 85%, at least 90%, at least 91%, at least 92%, at least 93%, at least 94%, at least 95%, at least 96%, at least 97%, at least 98%, at least 99%) identical to SEQ ID NO: 3 or SEQ ID NO: 13; (ii) a light chain comprising an amino acid sequence encoded by a polynucleotide sequence of SEQ ID NO: 21 or 23; and (iii) a light chain comprising an amino acid sequence encoded by a polynucleotide that hybridizes under stringent conditions to the complement of a polynucleotide consisting of SEQ ID NO: 21 or 23; or (B) a heavy chain selected from the group consisting of: (i) a heavy chain comprising an amino acid sequence that is at least 80% (e.g., at least 85%, at least 90%, at least 91%, at least 92%, at least 93%, at least 94%, at least 95%, at least 96%, at least 97%, at least 98%, at least 99%) identical to SEQ ID NO: 4 or SEQ ID NO: 14; (ii) a heavy chain comprising an amino acid sequence encoded by a polynucleotide sequence of SEQ ID NO: 22 or 24, and (iii) a heavy chain comprising an amino acid sequence encoded by a polynucleotide that hybridizes under stringent conditions to the complement of a polynucleotide consisting of SEQ ID NO: 22 or 24; or (C) a light chain variable domain of (A) and a heavy chain variable domain of (B).

The concentration of denosumab or other human anti-RANKL antibody, or antigen-binding portion thereof, in the aqueous formulation can generally be in any useful range, e.g. about 0.1 to about 200 mg/mL. As the concentration is increased, there is an increase in viscosity, which can hinder processing of the formulation into a sterile dosage presentation for pharmaceutical use.

In one aspect, the improved stability of the formulation by an amino acid aggregation inhibitor can exist at any concentration of denosumab or other human anti-RANKL antibody, or antigen-binding portion thereof, including about 10 mg/mL to about 200 mg/mL, or about 15 mg/mL to about 150 mg/mL, or about 30 mg/mL to about 200 mg/mL, or about 60 mg/mL to about 200 mg/mL, or about 60 mg/mL to about 180 mg/mL, or about 60 mg/mL to about 160 mg/mL, or about 60 mg/mL to about 150 mg/mL, or about 60 mg/mL to about 140 mg/mL, or about 60 mg/mL to about 130 mg/mL, or about 60 mg/mL to about 120 mg/mL, or about 60 mg/mL to about 110 mg/mL, or about 60 mg/mL to about 100 mg/mL, or about 60 mg/mL to about 90 mg/mL, or about 60 mg/mL to about 80 mg/mL, or about 60 mg/mL to about 70 mg/mL, or about 70 mg/mL to about 200 mg/mL, or about 70 mg/mL to about 180 mg/mL, or about 70 mg/mL to about 160 mg/mL, or about 70 mg/mL to about 150 mg/mL, or about 70 mg/mL to about 140 mg/mL, or about 70 mg/mL to about 130 mg/mL, or about 70 mg/mL to about 120 mg/mL, or about 70 mg/mL to about 110 mg/mL, or about 70 mg/mL to about 100 mg/mL, or about 70 mg/mL to about 90 mg/mL, or about 70 mg/mL to about 80 mg/mL, for example 120 mg/mL.

In another aspect, the concentration of denosumab or other human anti-RANKL antibody, or antigen-binding portion thereof, for formulations having a pH of about 5.0 to less than 5.2 is contemplated to include ranges of greater than 70 mg/mL, or at least 71 mg/mL, or at least about 75 mg/mL, or at least about 80 mg/mL, or at least about 85 mg/mL, or at least about 90 mg/mL, or at least about 95 mg/mL, or at least about 100 mg/mL, or at least about 105 mg/mL, or at least about 110 mg/mL, or at least about 115 mg/mL, or at least about 120 mg/mL, and up to about 200 mg/mL. For example contemplated ranges include, 71 mg/mL to about 200 mg/mL, or about 75 mg/mL to about 200 mg/mL, or about 75 mg/mL to about 180 mg/mL, or about 75 mg/mL to about 160 mg/mL, or about 75 mg/mL to about 150 mg/mL, or about 75 mg/mL to about 140 mg/mL, or about 75 mg/mL to about 130 mg/mL, or about 75 mg/mL to about 120 mg/mL, or about 75 mg/mL to about 110 mg/mL, or about 75 mg/mL to about 100 mg/mL, or about 75 mg/mL to about 90 mg/mL, or about 120 mg/mL to about 200 mg/mL, or about 120 mg/mL to about 180 mg/mL, or about 120 mg/mL to about 160 mg/mL, or about 120 mg/mL to about 140 mg/mL, for example 120 mg/mL.

In exemplary aspects, the aqueous pharmaceutical formulation comprises the antibody, or antigen-binding portion thereof, at a concentration greater than 70 mg/mL, e.g., greater than 80 mg/mL, greater than 90 mg/mL, greater than 100 mg/mL, greater than 125 mg/mL, greater than 150 mg/mL, greater than 175 mg/mL, greater than 200 mg/mL, greater than 225 mg/mL, greater than 250 mg/mL, greater than 275 mg/mL. In exemplary aspects, the aqueous pharmaceutical formulation comprises the antibody, or antigen-binding portion thereof, at a concentration less than about 300 mg/mL, e.g., less than about 275 mg/mL, less than about 250 mg/mL, less than about 225 mg/mL, less than about 200 mg/mL, less than about 175 mg/mL, or less than about 150 mg/mL. In exemplary aspects, the concentration of the antibody, or antigen-binding portion thereof, in the formulation is in a range of about 10 mg/mL to about 300 mg/mL, e.g., about 25 mg/mL to about 300 mg/mL, about 50 mg/mL to about 300 mg/mL, about 75 mg/mL to about 300 mg/mL, about 125 mg/mL to about 300 mg/mL, about 150 mg/mL to about 300 mg/mL, about 175 mg/mL to about 300 mg/mL, about 200 mg/mL to about 300 mg/mL, about 225 mg/mL to about 300 mg/mL, about 250 mg/mL to about 300 mg/mL, about 275 mg/mL to about 300 mg/mL, about 10 mg/mL to about 275 mg/mL, about 10 mg/mL to about 250 mg/mL, about 10 mg/mL to about 225 mg/mL, about 10 mg/mL to about 200 mg/mL, about 10 mg/mL to about 175 mg/mL, about 10 mg/mL to about 150 mg/mL, about 10 mg/mL to about 125 mg/mL, about 10 mg/mL to about 100 mg/mL, about 10 mg/mL to about 75 mg/mL, about 10 mg/mL to about 50 mg/mL, or about 10 mg/mL to about 25 mg/mL. In exemplary aspects, the aqueous pharmaceutical formulation comprises a concentration of the antibody or antigen-binding portion thereof, in a range of greater than 70 mg/mL to about 300 mg/mL, e.g., greater than 80 mg/mL to about 300 mg/mL, greater than 90 mg/mL to about 300 mg/mL, greater than 100 mg/mL to about 300 mg/mL, greater than 125 mg/mL to about 300 mg/mL, greater than 150 mg/mL to about 300 mg/mL, greater than 175 mg/mL to about 300 mg/mL, greater than 200 mg/mL to about 300 mg/mL, greater than 70 mg/mL to about 275 mg/mL, greater than about 70 mg/mL to about 250 mg/mL, greater than about 70 mg/mL to about 225 mg/mL, greater than about 70 mg/mL to about 200 mg/mL, greater than about 70 mg/mL to about 175 mg/mL, greater than about 70 mg/mL to about 150 mg/mL, greater than about 70 mg/mL to about 125 mg/mL, greater than about 70 mg/mL to about 100 mg/mL. In exemplary aspects, the aqueous pharmaceutical formulation comprises a concentration of the antibody or antigen-binding portion thereof in a range of about 100 to about 140 mg/mL, e.g., about 110 mg/mL, about 120 mg/mL, about 130 mg/mL. The aqueous pharmaceutical formulation in some aspects, comprises a concentration of the antibody or antigen-binding portion thereof that is about 120 mg/mL±12 mg/mL, e.g., about 108 mg/mL to about 132 mg/mL, about 115 mg/mL to about 125 mg/mL, about 116 mg/mL, about 117 mg/mL, about 118 mg/mL, about 119 mg/mL, about 120 mg/mL, about 121 mg/mL, about 122 mg/mL, about 123 mg/mL, about 124 mg/mL.

Denosumab and other human anti-RANKL monoclonal antibodies and antigen-binding portions thereof can be prepared according to the description provided in international patent publication WO 2003002713 A2.

Formulation studies on high concentration denosumab solutions (e.g. 120 mg/mL), described below, showed a large increase in HMWS formation (rate and extent) below pH 5 and especially at lower pH (e.g. pH 4.5). As pH increased, there was shown to be an increase in formation of the dimer species. Balancing the two effects, it is contemplated that a formulation described herein will have a pH in a range of about 5.0 to less than 5.2, or about 5.0 to about 5.19, or about 5.0 to about 5.15, or about 5.0 to about 5.10, for example about 5.0, about 5.05, about 5.1, or about 5.15.

The studies described herein also showed an independent stabilizing and aggregation-reducing effect made possible by inclusion of an amino acid aggregation inhibitor. Accordingly, it is contemplated that when an amino acid aggregation inhibitor is included, the formulation pH can be in a range of about 4.9 to about 5.4, or about 5.0 to about 5.4, or about 5.0 to about 5.2, or about 5.0 to less than 5.2, or about 5.0 to 5.19, or about 5.0 to about 5.15, or about 5.0 to about 5.10, for example about 5.0, about 5.05, about 5.1, or about 5.15, or about 5.2.

The aqueous formulation can be buffered. When used, the buffer can be an organic buffer. The buffer system can be centered at 25° C. around pH 4 to 5.5, or 4.5 to 5.5, or 4.5 to 5, for example. For example, the buffer system can have a pKa within one pH unit of pH 5.0-5.2 at 25° C. One such buffer system is acetic acid/acetate, having a pKa of about 4.75 at 25° C. Another such buffer system is glutamic acid/glutamate, having a pKa of about 4.27 at 25° C. Other alternative buffer systems contemplated include systems based on ions including succinate (pKa of 4.21 at 25° C.), propionate (pKa of 4.87 at 25° C.), malate (pKa of 5.13 at 25° C.), pyridine (pKa of 5.23 at 25° C.) and piperazine (pKa of 5.33 at 25° C.). It is contemplated that the buffer can be provided as the sodium salt (or disodium salt, as appropriate), or in the alternative as a potassium, magnesium, or ammonium salt. Buffers can be based on acetate, citrate, succinate, phosphate, and hydroxymethylaminomethane (Tris), for example. Buffers based on acetate, glutamate, and succinate are particularly contemplated, e.g. acetate or glutamate.

A comparison of HMWS formation by Size Exclusion Ultra High Performance Liquid Chromatography (SE-UHPLC) in 120 mg/mL denosumab formulations having acetate or glutamate buffers, but otherwise equivalent, showed that there was no difference between the buffer type when evaluated over four weeks of storage at 37° C.

When used, the buffer will be included in a sufficient amount to maintain the selected pH of the formulation at storage conditions for the product shelf life, e.g. 3 years at 4° C., or 1 month at 25° C., or 2 weeks at 25° C., or 7 days at 25° C. The buffer concentration can be in a range of about 2 mM to about 40 mM, or about 5 mM to about 20 mM, or about 10 mM to about 25 mM, or about 15 mM to about 25 mM, for example 10 mM, or 15 mM, or 18 mM, or 25 mM. For example, an acetate buffer used with the anti-RANKL monoclonal antibody (e.g. denosumab) and phenylalanine can be in a range of about 2 mM to about 30 mM, or about 16 mM to about 41 mM, or about 25 mM to about 39 mM, or about 30 mM to about 34 mM. Put another way, a diafiltration buffer used for concentrating the antibody to a concentration greater than 70 mg/mL (e.g. 120 mg/mL) can be in a range of 5 mM to about 30 mM, or about 15 mM to about 25 mM, or about 20 mM. It is also contemplated to provide an amino acid-stabilized formulation that is self-buffered. In exemplary aspects, the buffer is included in a sufficient amount to maintain the selected pH of the formulation at storage conditions for the product shelf life, e.g., 36 months at about 2° C. to about 8° C., optionally, followed by about 1 month at about 20° C. to about 30° C.

The aqueous pharmaceutical formulation in some aspects, comprises a buffer, and optionally, the buffer is centered, at 25° C., in a range of about pH 4.0 to about pH 5.5. In some aspects, the buffer has a pKa within one pH unit of pH 5.0-5.2 at 25° C. The aqueous pharmaceutical formulation in certain aspects, comprises about 5 mM to about 60 mM buffer, about 5 mM to about 50 mM buffer, or about 9 mM to about 45 mM buffer (e.g., about 15 mM to about 30 mM buffer, e.g., about 20 mM, about 25 mM buffer). In exemplary aspects, the buffer is acetate or glutamate.

The formulation can also include one or more stabilizers against protein aggregation and other formulation excipients. Such stabilizers and excipients are contemplated to include, but are not limited to, amino acid aggregation inhibitors, tonicity modifiers, surfactants, solubilizing agents (e.g. N-Methyl-2-pyrrolidone), PEG conjugation, and cyclodextrins (e.g., Captisol®).

The term "amino acid aggregation inhibitor" refers to an amino acid or a combination of amino acids (e.g. mixtures, or dipeptides, or oligopeptides having 2 to 10 residues), where any given amino acid is present either in its free base form or in its salt form (e.g. arginine HCl), or an amino acid analog, and which reduces HMWS or inhibits formation of HMWS. Salts including sodium salts, potassium salts, and hydrochloride salts are contemplated. In addition, arginine salts with hydrochloride, glutamate, butyrate, and glycolate are contemplated. Where a combination of amino acids is used, all of the amino acids may be present in their free base forms, all may be present in their salt forms, or some may be present in their free base forms while others are present in their salt forms. In addition to or in the alternative to dipeptides and oligopeptides, mixtures of one or more amino acids can be used, e.g. a mixture of arginine and phenylalanine. In alternative embodiments, only one type of amino acid aggregation inhibitor is present in the aqueous pharmaceutical formulation. In exemplary aspects, only one amino acid is present, e.g., only L-arginine or only L-phenylalanine is present in the formulation.

It is contemplated to use one or more amino acids which carry a charged side chain, for example one or more of arginine, lysine, histidine, aspartate, and glutamate. The amino acids can be selected from basic amino acids, e.g., arginine, lysine, histidine, or a combination thereof. Arginine is particularly contemplated. Any stereoisomer (i.e., L, D, or DL isomer) of a particular amino acid, or combinations of these stereoisomers, may be used in the present method or formulation so long as the particular amino acid is present in its free base form or its salt form. An L-stereoisomer is particularly contemplated, e.g. L-arginine. Optionally the amino acid is one having a positively charged side chain, e.g. arginine.

In another aspect, it is contemplated to use one or more amino acids which have aromatic rings in their side chains, e.g. phenylalanine, tyrosine, tryptophan, or a combination thereof. Phenylalanine is particularly contemplated.

In another aspect, it is contemplated to use one or more hydrophobic amino acids, for example alanine, isoleucine, leucine, phenylalanine, valine, proline, or glycine.

In another aspect, it is contemplated to use one or more aliphatic, hydrophobic amino acids, for example, alanine, isoleucine, leucine, or valine. Leucine is particularly contemplated.

Analogs of amino acids which show aggregation reducing or inhibiting effects could also be used in the present method or formulation. The term "amino acid analog" refers to a derivative of the naturally occurring amino acid. Contemplated analogs include for example, amino- and N-monoethyl-, and n-acetyl-derivatives. Other contemplated analogs include dipeptides, or oligopeptides having 2 to 10 residues, e.g. arginine-arginine and phenylalanine-arginine. In one type of embodiment, it is contemplated that n-acetyl arginine and n-acetyl lysine will not be used alone, but can be used in combination with another amino acid aggregation inhibitor. As with the amino acids, the amino acid analogs are used in the present method or formulation in either their free base form or their salt form.

The amino acid aggregation inhibitor(s) used in the present method or formulation protect the therapeutically active protein against various stresses thereby increasing or/and maintaining stability of the protein or formulation containing the protein during the lifetime of the protein (before and during storage, before use). Herein, the term "stress" includes but is not limited to heat, freezing, pH, light, agitation, oxidation, dehydration, surfaces, shear, freeze/thawing, pressure, heavy metals, phenolic compounds, denaturants, etc., from any source, e.g. transportation. Heat stress is particularly contemplated. The term stress encompasses any factor that modulates (i.e. reduces, maintains or increases) the stability of a protein or a formulation containing the protein. Increased and/or maintained stability with addition of an amino acid aggregation inhibitor occurs in a concentration dependent manner. That is, increasing concentrations of amino acid aggregation inhibitor lead to increased and/or maintained stability of a protein or a formulation containing a protein of the present invention when that protein or formulation containing that protein normally exhibits aggregate formation in the absence of the amino acid aggregation inhibitor. As shown in the Examples below, inclusion of an amino acid aggregation inhibitor in the formulation can also reduce the amount of already-formed HMWS. For example, such amino acid aggregation inhibitors include arginine and arginine-phenylalanine dipeptide. Determination of the amount of a particular amino acid aggregation inhibitor to be used in the present method or formulation to decrease aggregate formation thereby increasing protein stability, and thus increasing stability of the formulation during the entire lifetime of the protein, can readily be determined for denosumab or any particular human anti-RANKL monoclonal antibody of interest in view of the disclosure herein.

The presence of an amino acid aggregation inhibitor in the formulation has been shown to reduce the amount of dimer species and its kinetic rate of formation. For example, including arginine at a concentration of 75 mM in a denosumab formulation having a pH of 5.2 resulted in an approximately 0.3% and 25% reduction in the amounts of the dimer species and its kinetic rate of formation, respectively, after 1 month at 37° C. when compared to a similar formulation without arginine at a pH of 5.2. In contrast, a monoclonal antibody which is not a human anti-RANKL monoclonal antibody was found to not be stabilized by inclusion of arginine, and instead resulted in increased HMWS. Accordingly, another method of the disclosure is a method of reducing HMWS in a formulation of denosumab or another human anti-RANKL monoclonal antibody by addition of an amino acid aggregation inhibitor, e.g. arginine or phenylalanine.

Accordingly, in exemplary embodiments, the aqueous pharmaceutical formulation comprises an amino acid aggregation inhibitor, which optionally is an amino acid. In exemplary aspects, the amino acid is an L-stereoisomer amino acid (L-amino acid), though D-stereoisomer amino acids (D-amino acids) are contemplated. In some aspects, the amino acid aggregation inhibitor comprises an amino acid comprising a charged side chain, also referred to herein as a "charged amino acid". The term "charged amino acid" refers to an amino acid that comprises a side chain that is negative-charged (i.e., de-protonated) or positive-charged (i.e., protonated) in aqueous solution at physiological pH. For example negative-charged amino acids include, for instance, aspartic acid and glutamic acid, whereas positive-charged amino acids include, for example, arginine, lysine and histidine. Charged amino acids include the charged amino acids among the 20 coded amino acids, as well as atypical or non-naturally occurring or non-coded amino acids. Accordingly, in exemplary aspects, the amino acid aggregation inhibitor is an amino acid comprising a positive-charged side chain. In exemplary instances, the amino acid comprising a positive-charged side chain comprises a side chain structure of Formula I or Formula II:

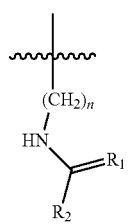

[Formula I]

wherein n is 1 to 7, wherein each of $R_1$ and $R_2$ is independently selected from the group consisting of H, $C_1$-$C_{18}$ alkyl, ($C_1$-$C_{18}$ alkyl)OH, ($C_1$-$C_{18}$ alkyl)NH$_2$, NH, NH$_2$($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl), wherein $R_7$ is H or OH, wherein optionally one of $R_1$ and $R_2$ is a free amino group (—NH$_3^+$),

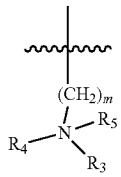

[Formula II]

wherein m is 1 to 7, wherein each of $R_3$ and $R_4$ is independently selected from Group A consisting of: H, $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_8$, and ($C_1$-$C_4$ alkyl)($C_3$-$C_9$ heteroaryl), wherein $R_8$ is H or OH, wherein, $R_5$ is optionally present, and, when present, is selected from Group A, optionally, wherein each of $R_3$ and $R_4$ and $R_5$ is H.

In exemplary aspects, the amino acid comprising a positive-charged side chain comprises a side chain structure of Formula I and, n is in a range of 2 to 4. In alternative or additional aspects, $R_1$ is NH or NH$_2$. In exemplary aspects, $R_2$ is NH$_2$ or NH$_3^+$. The amino acid comprising a positive-charged side chain in exemplary instances is arginine. In exemplary aspects, the amino acid comprising a positive-charged side chain comprises a side chain structure of Formula II and, m is in a range of 3 to 5. In some aspects, each of $R_3$ and $R_4$ is H. In certain instances, $R_5$ is present, and optionally is H. In some instances, the amino acid comprising a positive-charged side chain is lysine. The amino acid comprising a positive-charged side chain is present in the formulation as a salt, in some aspects, optionally, a hydrochloride (HCl) salt. Accordingly, in exemplary aspects, the aqueous pharmaceutical composition comprises L-arginine HCl or L-lysine HCl.

In exemplary aspects, the amino acid aggregation inhibitor is an aromatic amino acid. In some instances, the aromatic amino acid comprises a phenyl or an indole. In exemplary aspects, the aromatic amino acid comprises a $C_1$-$C_6$ alkyl chain (e.g., a $C_1$-$C_3$ alkyl chain) between the alpha carbon and the phenyl or indole. In exemplary instances, the aromatic amino acid is L-phenylalanine. In other instances, the aromatic amino acid is L-tryptophan.

In exemplary aspects, the amino acid aggregation inhibitor is a hydrophobic amino acid. Hydrophobicity may be measured or scored according to any one of the hydrophobicity scales known in the art. In general, the more positive the score, the more hydrophobic is the amino acid. In some instances, the hydrophobicity is scored on the Kyte and Doolittle hydrophobicity scale (Kyte J, Doolittle R F (May 1982). "A simple method for displaying the hydropathic character of a protein". J. Mol. Biol. 157 (1): 105-32.) In some aspects, the hydrophobic amino acid has a score greater than about 2.5 on the Kyte and Doolittle hydrophobicity scale. The hydrophobic amino acid in certain aspects comprises a side chain comprising a $C_2$ to $C_{12}$ alkyl, branched or straight-chained, or a $C_4$ to $C_8$ cycloalkyl, a $C_4$ to $C_8$ heterocycle comprising a nitrogen heteroatom, optionally, wherein the heterocycle is an imidazole, pyrrole, or indole. For purposes herein, the term "cycloalkyl" encompasses any carbon cycle, including carbon bi-cycles or tri-cycles.

In exemplary aspects, the hydrophobic amino acid comprises a $C_3$ to $C_8$ alkyl, optionally, the hydrophobic amino acid comprises a branched $C_3$ alkyl or branched $C_4$ alkyl.

The hydrophobic amino acid is L-valine, L-leucine, or L-isoleucine, in certain aspects.

The amino acid aggregation inhibitor is used in an amount effective to provide increased stability, and can be used at a concentration in a range of about 10 mM to about 200 mM, for example a range of about 30 mM to about 120 mM, or about 38 mM to about 150 mM, or about 38 mM to about 113 mM, or about 38 mM to about 75 mM, for example about 10 mM, about 38 mM, about 75 mM, about 113 mM, or about 150 mM. In exemplary aspects, the aqueous pharmaceutical formulation comprises about 5 mM to about 300 mM amino acid aggregation inhibitor, optionally, about 25 mM to about 90 mM amino acid aggregation inhibitor. In some aspects, aqueous pharmaceutical formulation comprises about 5 mM to about 150 mM (e.g., about 10 mM to about 150 mM, about 15 mM to about 150 mM, about 20 mM to about 150 mM, about 25 mM to about 150 mM, about 5 mM to about 140 mM, about 5 mM to about 130 mM, about 5 mM to about 120 mM, about 5 mM to about 110 mM, about 5 mM to about 100 mM, about 5 mM to about 90 mM) amino acid aggregation inhibitor, when the amino acid aggregation inhibitor is an amino acid comprising a positive-charged side chain, optionally, L-arginine. In some aspects, the aqueous pharmaceutical formulation comprises about 30 mM to about 80 mM (e.g., about 35 mM, about 40 mM, about 45 mM, about 50 mM, about 55 mM, about 60 mM, about 65 mM, about 70 mM, about 75 mM) amino acid aggregation inhibitor, when the amino acid aggregation inhibitor is an amino acid comprising a positive-charged side chain, optionally, L-arginine.

In some aspects, the aqueous pharmaceutical formulation comprises about 5 mM to about 180 mM (e.g., about 10 mM to about 180 mM, about 15 mM to about 180 mM, about 20 mM to about 180 mM, about 25 mM to about 180 mM, about 5 mM to about 170 mM, about 5 mM to about 170 mM, about 5 mM to about 160 mM, about 5 mM to about 150 mM, about 5 mM to about 140 mM, about 5 mM to about 130 mM, about 5 mM to about 120 mM, about 5 mM to about 110 mM) amino acid aggregation inhibitor, when the amino acid aggregation inhibitor is an aromatic amino acid, optionally, L-phenylalanine. In exemplary instances, the aqueous pharmaceutical formulation comprises about 5 mM to about 100 mM (e.g., about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM) amino acid aggregation inhibitor, optionally, about 20 mM to about 50 mM amino acid aggregation inhibitor, when the amino acid aggregation inhibitor is an aromatic amino acid, optionally, L-phenylalanine.

Optionally, the aqueous pharmaceutical formulation comprises about 5 mM to about 300 mM amino acid aggregation inhibitor, when the amino acid aggregation inhibitor is a hydrophobic amino acid, optionally, L-valine, L-isoleucine, or L-leucine. Optionally, the aqueous pharmaceutical formulation comprises about 5 mM to about 200 mM (e.g., about 10 mM to about 200 mM, about 20 mM to about 200 mM, about 30 mM to about 200 mM, about 40 mM to about 200 mM, about 50 mM to about 200 mM, about 60 mM to about 200 mM, about 70 mM to about 200 mM, about 80 mM to about 200 mM, about 90 mM to about 200 mM, about 100 mM to about 200 mM, about 5 mM to about 290 mM, about 5 mM to about 280 mM, about 5 mM to about 270 mM, about 5 mM to about 260 mM, about 5 mM to about 250 mM, about 5 mM to about 240 mM, about 5 mM to about 230 mM, about 5 mM to about 220 mM, about 5 mM to about 210 mM) amino acid aggregation inhibitor, optionally, about 20 mM to about 50 mM amino acid aggregation inhibitor, when the amino acid aggregation inhibitor is a hydrophobic amino acid, optionally, L-valine, L-isoleucine, or L-leucine. In exemplary aspects, the aqueous pharmaceutical composition comprises: about 30 mM to about 80 mM L-arginine hydrochloride; about 20 mM to about 50 mM L-phenylalanine; about 20 mM to about 50 mM L-tryptophan; about 30 mM to about 80 mM L-lysine hydrochloride; about 20 mM to about 50 mM L-leucine; about 20 mM to about 50 mM L-isoleucine; about 20 mM to about 50 mM L-valine; or any combination thereof.

In exemplary aspects, the concentration of the amino acid aggregation inhibitor is in molar ratio with the antibody. The molar ratio of the amino acid aggregation inhibitor to the anti-RANKL antibody is, in some aspects, about 10 to about 200 (e.g., about 25 to about 150, about 50 to about 100), when the amino acid aggregation inhibitor is an aromatic amino acid, optionally, L-phenylalanine. Optionally, the molar ratio is about 20 to about 90. In exemplary aspects, the molar ratio of the amino acid aggregation inhibitor to the anti-RANKL antibody is about 20 to 300, when the amino acid aggregation inhibitor is an amino acid comprising a positive-charged side chain, optionally, L-arginine. Optionally, the molar ratio is about 45 to about 180.

Surfactants are surface active agents that are amphipathic (having a polar head and hydrophobic tail). Surfactants preferentially accumulate at interfaces, resulting in reduced interfacial tension. A surfactant can optionally be included in the formulation. Use of a surfactant can also help to mitigate formation of large proteinaceous particles.

In one type of embodiment, the surfactant can be a nonionic surfactant. Examples include polyoxyethylene sorbitan fatty acid esters (e.g. polysorbate 20, polysorbate 80), alkylaryl polyethers, e.g. oxyethylated alkyl phenol (e.g. Triton™ X-100), and poloxamers (e.g. Pluronics®, e.g. Pluronic® F68), and combinations of any of the foregoing, either within a class of surfactants or among classes of surfactants. Polysorbate 20 and polysorbate 80 are particularly contemplated.

A surfactant concentration in a range of about 0.004% (w/v) to about 0.1% (w/v) (e.g., for polysorbate 20 or polysorbate 80) is suitable, for example about 0.004% to about 0.05%, or about 0.004% to about 0.02%, or about 0.01%. In exemplary aspects, the formulation comprises at least about 0.004 (w/v) % surfactant, and optionally, less than about 0.15 (w/v) %. In exemplary aspects, about 0.005 (w/v) % to about 0.015 (w/v) % surfactant is present in the formulation, optionally, about 0.005 (w/v) %, about 0.006 (w/v) %, about 0.007 (w/v) %, about 0.008 (w/v) %, about 0.009 (w/v) %, about 0.010 (w/v) %, about 0.011 (w/v) %, about 0.012 (w/v) %, about 0.013 (w/v) %, or about 0.014 (w/v) %.

The stabilized aqueous formulation can be suitable for administration by any acceptable route, including parenteral, and specifically subcutaneous. For example, the subcutaneous administration can be to the upper arm, upper thigh, or abdomen. Other routes include intravenous, intradermal, intramuscular, intraperitoneal, intranodal and intrasplenic, for example. The subcutaneous route is preferred.

If the solution is in a form intended for administration to a subject, it can be made to be isotonic with the intended site of administration. For example, the osmolality can be in a range of about 270 to about 350 mOsm/kG, or about 285 to about 345 mOsm/kG, or about 300 to about 315 mOsm/kG. For example, if the solution is in a form intended for administration parenterally, it can be isotonic with blood (about 300 mOsm/kG osmolality). In exemplary aspects, the aqueous pharmaceutical formulation has an osmolality in a range of about 200 mOsm/kg to about 500 mOsm/kg, or about 225 mOsm/kg to about 400 mOsm/kg, or about 250 mOsm/kg to about 350 mOsm/kg.

In exemplary aspects, the aqueous pharmaceutical formulation has a conductivity in a range of about 500 µS/cm to about 5500 µS/cm, optionally, wherein the conductivity is in a range of about 2500 µS/cm to about 5500 µS/cm, when the formulation comprises an amino acid comprising a positive-charged side chain, or in a range of about 500 µS/cm to about 2000 µS/cm, when the formulation comprises an aromatic amino acid or lacks amino acid aggregation inhibitor. The aqueous pharmaceutical formulation of any one of the preceding claims, having a viscosity that is not more than about 6 cP at 5° C., optionally, wherein the viscosity is about 4.5 cP to about 5.5 cP. The aqueous pharmaceutical formulation in certain aspects has a viscosity that is less than about 13 cP at 25° C., optionally, about 2.0 cP to about 10 cP, optionally, about 2.5 cP to about 4 cP.

Tonicity modifiers, or tonicity adjusting agents are known in the art, and include compounds such as salts (e.g., sodium chloride, potassium chloride, calcium chloride, sodium phosphate, potassium phosphate, sodium bicarbonate, calcium carbonate, sodium lactate), sugars (e.g., dextran, dextrose, lactose, trehalose), and sugar alcohols (e.g., mannitol, sorbitol, xylitol, glycerol, propylene glycol). In certain aspects, the tonicity modifier is selected from the group consisting of: sorbitol, mannitol, sucrose, trehalose, glycerol, and combinations thereof. In exemplary instances, the tonicity modifier is sorbitol. Sorbitol can be used, e.g. at a concentration in a range of 0.1% (w/v) to 5% (w/v), or 1.2% (w/v) to 5% (w/v), for example 3.6% (w/v), 4.6% (w/v), or 4.7% (w/v). Optionally, the formulation comprises about 1.0 (w/w) % to about 5.0 (w/w) % tonicity modifier. For instance, the formulation comprises about 2.0 (w/w) % to about 5.0 (w/w) % sorbitol, or about 3.5 (w/w) % to about 5.0 (w/w) % sorbitol, or about 4.0% (w/w) to about 5.0 (w/w) % sorbitol. In some aspects, the formulation does not comprise any sorbitol or is free of sorbitol. In exemplary aspects, the formulation does not comprise any tonicity modifier.

Other excipients known in the art can be used in the formulation, as long as they do not negatively affect the stability. Sugars and polyols can be used to protect proteins from aggregation, including providing freeze/thaw stability. Such compounds include sorbitol, mannitol, glycerol, erythritol, caprylate, tryptophanate, sarcoside, and glycine. Stabilizers for preparing lyophilized preparations can also be used, for example stabilizing sugars, e.g. disaccharides such as trehalose and sucrose. A lyophilized preparation can also include a bulking agent, as is known in the art. Other excipients known in the art for protein stabilization include, solubilizing agents (e.g. N-Methyl-2-pyrrolidone), polyethylene glycol (PEG), and cyclodextrins (e.g., Captisol®). Pharmaceutically-acceptable acids and bases can be used to adjust solution pH, e.g. sodium hydroxide.

For parenteral administration, the formulation can be in the form of a pyrogen-free, parenterally acceptable, sterile aqueous solution comprising denosumab or another human anti-RANKL monoclonal antibody, with or without additional therapeutic agents, in a pharmaceutically acceptable vehicle. In certain embodiments, a vehicle for parenteral injection is sterile distilled water in which the denosumab or another human anti-RANKL monoclonal antibody, with or without at least one additional therapeutic agent, is formulated as a sterile, isotonic solution. The formulation will contain pharmaceutically acceptable excipients, e.g. USP (United States Pharmacopeia) grade excipients.

A "preservative" is a compound which can be included in a pharmaceutical formulation to reduce bacterial action therein, for example thus facilitating the production of a multi-use formulation. Examples of preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols including phenol, butyl and benzyl alcohol, alkyl parabens including methyl and propyl paraben, catechol, resorcinol, cyclohexanol, 3-pentanol, and m-cresol. In the alternative, the formulation can be free of preservatives. For example, the formulation when presented in a single-use dosage form can be free of preservatives.

While the formulation has been described herein in its aqueous form, the stabilized formulation can also be subsequently lyophilized to prepare a lyophilizate. Accordingly, unless context dictates otherwise, references to the formulation and its method of use are contemplated to include a lyophilizate resulting from the stabilized aqueous solution.

The pharmaceutical formulation to be used for in vivo administration typically is sterile. In certain embodiments, this may be accomplished by filtration through sterile filtration membranes. In certain embodiments, parenteral compositions generally are placed into a container having a sterile access port, for example, an intravenous solution bag, or vial having a stopper pierceable by a hypodermic injection needle, or a prefilled syringe. In certain embodiments, the formulation may be stored either in a ready-to-use form or in a form (e.g., lyophilized) that is reconstituted or diluted prior to administration.

In certain embodiments, the present invention is directed to kits for producing a single-dose administration unit. In certain embodiments, the kits may each contain both a first container having a dried preparation of denosumab or other human anti-RANKL monoclonal antibody made from a solution formulation described herein, and a second container having sterile water or an aqueous solution. In certain embodiments of this invention, kits containing single and multi-chambered pre-filled syringes (e.g., liquid syringes and lyosyringes) are included.

The stabilized formulation described herein can be used together with one or more additional therapeutic agents, e.g. calcium and a vitamin D compound. The stabilized formulation described herein can be administered to a patient receiving therapy with an additional therapeutic agent, or the stabilized formulation described herein can be co-administered with an additional therapeutic agent.

The stabilized formulation, in any of its aspects and embodiments described herein, can be used to prevent or treat any disease responsive to denosumab or another human anti-RANKL monoclonal antibody, or an antigen-binding portion thereof. Such uses and related methods include, but are not limited to, the aspects and embodiments described below.

In one aspect the formulation can be used for preventing a skeletal-related event (SRE) in a patient in need thereof, including administering an effective amount of a stabilized formulation described herein. The SRE can be selected from the group consisting of a pathologic fracture, radiation therapy to bone, surgery to bone, and spinal cord compression, for example. The patient can be one having a bone metastasis from a solid tumor. The solid tumor can be one or more of breast cancer, prostate cancer, lung cancer, non-small cell lung cancer and renal cell carcinoma, for example. The amount of the formulation can be effective to reduce the bone turnover marker urinary N-terminal telopeptide corrected for creatinine (uNTx/Cr), optionally by at least 80%. The patient can be a patient with multiple myeloma.

In another aspect the formulation can be used for treating a patient with giant cell tumor of bone, including administering an effective amount of a stabilized formulation described herein. In one type of embodiment, the patient has giant cell tumor of bone that is recurrent, unresectable, or for which surgical resection is likely to result in severe morbidity. The patient can be an adult or a skeletally-mature adolescent, for example.

In another aspect the formulation can be used for treating a patient with hypercalcemia of malignancy bone, including administering an effective amount of a stabilized formulation described herein. In one aspect, the malignancy can be refractory to bisphosphonate therapy. The method or use can include administering an amount of the formulation effective to reduce or maintain the patient's serum calcium at a level less than or equal to about 11.5 mg/dL.

In another aspect the formulation can be used for treating osteoporosis in a patient in need thereof, including administering an effective amount of a stabilized formulation described herein. For example, the patient can be a post-menopausal woman at high risk for fracture. In another type of embodiment, the patient can be a man at high risk for fracture.

In another aspect the formulation is used for increasing bone mass in a patient in need thereof, including administering an effective amount of a stabilized formulation described herein. For example, the amount of the formulation administered can be an amount effective to decrease the incidence of new vertebral fractures and/or nonvertebral fractures. In another type of embodiment, the amount of the formulation administered can be an amount effective to decrease bone resorption. In another type of embodiment, the amount of the formulation can be an amount effective to increase bone density in the patient in at least one area selected from lumbar spine, total hip, and femoral neck. In another type of embodiment, the amount of the formulation can be an amount effective to increase bone mass in the patient's cortical bone and/or trabecular bone. In another type of embodiment, the amount of the formulation can be an amount effective to reduce the bone resorption marker serum type 1 C-telopetide (CTX). The patient in need thereof can optionally have osteoporosis. In another type of embodiment, the patient in need thereof can be a woman at high risk for fracture receiving adjuvant aromatase inhibitor therapy for breast cancer. In another type of embodiment, the patient in need thereof can be a man at high risk for fracture receiving androgen deprivation therapy for non-metastatic prostate cancer. In another type of embodiment, the patient in need thereof can be a man with osteoporosis at high risk for fracture.

In another aspect, the formulation can be used as adjuvant treatment for post-menopausal women with early stage breast cancer at high risk of disease recurrence receiving adjuvant/neoadjuvant cancer therapy.

In another aspect, the formulation can be used as first-line treatment of patients with metastatic non-small cell lung cancer in combination with platinum-based chemotherapy.

In another aspect the formulation can be used for treating idiopathic subglottic stenosis (ISS).

In another aspect the formulation can be used for breast cancer and ovarian cancer prevention in BRCA-1 mutated healthy females.

Optionally, the formulation can used in combination with an immune checkpoint inhibitor. Optionally, the immune checkpoint inhibitor is specific for a protein which functions in an immune-checkpoint pathway, e.g., for example, CTLA4, LAG3, PD-1, PD-L1, PD-L2, B7-H3, B7H4, BTLA, SLAM, 2B4, CD160, KLRG-1 or TIM3. Optionally, the immune checkpoint inhibitor is an antibody, antigen-binding fragment thereof, or an antibody protein product specific for CTLA4, LAG3, PD-1, PD-L1, PD-L2, B7-H3, B7H4, BTLA, SLAM, 2B4, CD160, KLRG-1 or TIM3. Such immune checkpoint inhibitors include but are not limited to: atezolizumab, avelumab, ipilimumab, tremelimumab, BMS-936558, MK3475, CT-011, AM-224, MDX-1105, IMP321, MGA271. PD-1 inhibitors include, for example, pembrolizumab and nivolumab. PD-L1 inhibitors include, for instance, atezolizumab, avelumab, and durvalumab. CTLA4 inhibitors include, e.g., ipilimumab. In another aspect the formulation can be used for treating melanoma patients with bone metastases, optionally in combination with a PD-1 antibody (e.g., nivolumab, pembrolizumab). In another aspect the formulation can be used for treating breast cancer patients, optionally, in combination with a CTLA4 inhibitor, such as ipilimumab.

In another aspect the formulation can be used to treat Giant cell rich tumors, e.g. in hyperparathyroidism or with a secondary aneurysmal bone cyst.

In another aspect the formulation can be used to treat progressive Metastatic Castration-Resistant Prostate Cancer (mCRPC). In another aspect the formulation can be used to treat castrate sensitive prostate cancer. In another aspect the formulation can be used to treat hormone resistant prostate cancer.

In another aspect the formulation can be used to treat Metastatic Breast Cancer (mBC). In another aspect the formulation can be used to treat pre-operative Breast Cancer. In another aspect the formulation can be used to treat early Breast Cancer. In other aspects the formulation can be used to treat hormone-receptor-negative, RANK-positive or RANK-negative primary breast cancer. In another aspect the formulation can be used to treat post-menopausal HER2 negative Breast Cancer.

In another aspect the formulation can be used to treat myelodysplastic syndrome, e.g. in an elderly patient.

In another aspect the formulation can be used to treat cancer treatment-induced bone loss (CTIBL).

In another aspect the formulation can be used to treat a uterine tumor of the cervix.

In another aspect the formulation can be used to induce immunomodulatory effects in patients with or without immunotherapy.

In another aspect the formulation can be used to prevent or treat bone loss associated with osteoporosis, Paget's disease, osteomyelitis, hypercalcemia, osteopenia, osteonecrosis, and rheumatoid arthritis. In another aspect the formulation can be used to prevent or treat inflammatory conditions with bone loss. In another aspect the formulation can be used to prevent or treat autoimmune conditions with bone loss. In another aspect the formulation can be used to prevent or treat bone loss associated with cancer, including breast, prostate, thyroid, kidney, lung, esophageal, rectal, bladder, cervical, ovarian, liver, and gastrointestinal cancers, multiple myeloma, lymphoma, and Hodgkin's Disease.

The formulation can be administered on any suitable timing schedule. In one embodiment, the administration is schedule is once every four weeks. Optionally, the administration can include administration on days 8 and 15 of the first month of therapy. In another type of embodiment, the administration can be on a schedule of once every six months. A schedule of once every six months is contemplated for use with osteoporosis and increasing bone mass, for example. Other contemplated maintenance doses are every 3 weeks, every 3 months, and every 6 weeks.

In some aspects, the aqueous pharmaceutical formulation is used to treat a patient with Multiple Myeloma or a Bone Metastasis from a Solid Tumor. In certain aspects, the formulation is administered at a dose of about 120 mg every 4 weeks as a subcutaneous injection in the upper arm, upper thigh, or abdomen.

In some aspects, the aqueous pharmaceutical formulation is used to treat a patient with a Giant Cell Tumor of Bone. In certain aspects, the formulation is administered at a dose of about 120 mg every 4 weeks with additional 120 mg doses on Days 8 and 15 of the first month of therapy. In some aspects, the formulation is administered subcutaneously in the upper arm, upper thigh, or abdomen of the patient. In some instances, calcium and vitamin D are administered to the patient to treat or prevent hypocalcemia.

In some aspects, the aqueous pharmaceutical formulation is used to treat a patient with hypercalcemia of Malignancy. In certain aspects, the formulation is administered at a dose of about 120 mg every 4 weeks with additional 120 mg doses on Days 8 and 15 of the first month of therapy. In some aspects, the formulation is administered subcutaneously in the upper arm, upper thigh, or abdomen.

In some aspects, the aqueous pharmaceutical formulation is used to treat postmenopausal women with osteoporosis at high risk for fracture, or used to increase bone mass in men at high risk for fracture receiving androgen deprivation therapy for nonmetastatic prostate cancer or in women at high risk for fracture receiving adjuvant aromatase inhibitor therapy for breast cancer. In some aspects, the aqueous pharmaceutical formulation is administered by a healthcare professional and at a dose of 60 mg every 6 months as a subcutaneous injection in the upper arm, upper thigh, or abdomen. In some aspects, the patient is also instructed to take calcium 1000 mg daily and at least 400 IU vitamin D daily.

One type of formulation according to the disclosure will contain denosumab, acetate, and arginine. The arginine is optionally L-arginine. The arginine is optionally L-arginine hydrochloride. The formulation can optionally include sorbitol. The formulation can optionally include polysorbate. The polysorbate can optionally be polysorbate 20. The pH can optionally be about 5.0 to about 5.2, or less than 5.2.

Another type of formulation according to the disclosure will contain denosumab, acetate, and phenylalanine. The formulation can optionally include sorbitol. The formulation can optionally include polysorbate. The polysorbate can optionally be polysorbate 20. The pH can optionally be about 5.0 to about 5.2, or less than 5.2. For instance, the formulation can include denosumab at a concentration of about 108 mg/mL to about 132 mg/mL, about 28.8 mM to about 35.2 mM acetate, 33.3 mM to about 40.7 mM phenylalanine, 3.51% (w/v) to about 4.29% (w/v) sorbitol, and about 0.009% (w/v) to about 0.011% (w/v) polysorbate 20, at pH 5.1, and optionally can be contained in a PFS, optionally containing about 1 mL or less than about 1 mL (e.g., about 0.5 mL) of the formulation. For example, the formulation can include denosumab at a concentration of 120 mg/mL, 32 mM acetate, 37 mM phenylalanine, 3.9% (w/v) sorbitol, and 0.01% (w/v) polysorbate 20, at pH 5.1, and optionally can be contained in a PFS, optionally containing about 1 mL or less than about 1 mL (e.g. about 0.5 mL) of the formulation. The formulation can be made by concentrating the denosumab using a diafiltration buffer containing 20 mM acetate, 4.2% (w/v) sorbitol, and 40 mM phenylalanine, at pH 4.7.

Another type of formulation according to the disclosure will contain denosumab, glutamate, and arginine. The arginine is optionally L-arginine. The arginine is optionally L-arginine hydrochloride. The formulation can optionally include sorbitol. The formulation can optionally include polysorbate. The polysorbate can optionally be polysorbate 20. The pH can optionally be about 5.0 to about 5.2, or less than 5.2.

Another type of formulation according to the disclosure will contain denosumab, acetate, arginine, and phenylalanine. The formulation can optionally include sorbitol. The formulation can optionally include polysorbate. The polysorbate can optionally be polysorbate 20. The pH can optionally be about 5.0 to about 5.2, or less than 5.2.

Another type of formulation according to the disclosure will contain denosumab, glutamate, arginine, and phenylalanine. The arginine is optionally L-arginine. The arginine is optionally L-arginine hydrochloride. The formulation can optionally include sorbitol. The formulation can optionally include polysorbate. The polysorbate can optionally be polysorbate 20. The pH can optionally be about 5.0 to about 5.2, or less than 5.2.

The formulations according to the disclosure can be made by any suitable method. In one type of method, a solution containing an anti-RANKL monoclonal antibody (e.g., denosumab) can be prepared at a concentration less than 70 mg/mL, a suitable amount of the amino acid aggregation inhibitor described herein can be added to the solution, and then the solution can be concentrated to an amount greater than 70 mg/mL described herein, e.g. 120 mg/mL. Optionally, the solution can be first over-concentrated, i.e. to a concentration of anti-RANKL monoclonal antibody (e.g., denosumab) greater than the final target concentration, and then the over-concentrated solution can be diluted, e.g. with a pH-adjusted buffer solution, to the final target concentration and pH. For example, the over-concentration can result in an amount of anti-RANKL monoclonal antibody (e.g., denosumab) in a range of 130 mg/mL to 300 mg/mL or 180 mg/mL to 300 mg/mL. The initial concentration of denosumab before concentration is not particularly limited, and can be, for example about 1 mg/mL, or about 2 mg/mL, or about 5 mg/mL, or about 8 mg/mL, or about 10 mg/mL, or about 20 mg/mL, or about 30 mg/mL, or about 40 mg/mL, or about 50 mg/mL, or about 60 mg/mL, or about 70 mg/mL, or in a range bracketed by any such concentrations, e.g. about 1 mg/mL to about 70 mg/mL, or about 1 mg/mL to about 10 mg/mL.

Concentration of the formulation can be carried out by any suitable method. In one aspect, the concentration process can include centrifugation. In another aspect, the concentration process can include ultrafiltration.

Introduction of the amino acid aggregation inhibitor into the formulation can be done by any suitable process. For example, the amino acid aggregation inhibitor can be introduced into the formulation via simple addition (spiking) into the formulation, e.g. as described in the Examples below. In another method, the amino acid aggregation inhibitor can be introduced into the formulation via diafiltration against a buffer solution containing the amino acid aggregation inhibitor, e.g. as described in the Examples below. The amino acid aggregation inhibitor can be introduced into the formulation before or after concentrating the anti-RANKL monoclonal antibody above 70 mg/mL. As shown in the Examples below, there is a benefit to adding the amino acid aggregation inhibitor to the solution prior to concentration, as it inhibits aggregation during the concentration process.

Accordingly, the disclosure provides methods of making a stable, aqueous pharmaceutical formulation comprising a human anti-human receptor activator of nuclear factor kappa-B ligand (anti-RANKL) monoclonal antibody, or an antigen-binding portion thereof. In exemplary instances, the method comprises combining the anti-RANKL monoclonal antibody, or antigen-binding portion thereof, at a concentration greater than 70 mg/mL with an amino acid aggregation inhibitor, a buffer, a surfactant, and optionally, a tonicity modifier. The antibody, or antigen binding portion may be any of those described herein, and the concentration of the antibody, or antigen binding portion thereof, may accord with the teachings herein. The amino acid aggregation inhibitor may be any of those described herein. For example, the amino acid aggregation inhibitor may be a positive charged amino acid, an aromatic amino acid, or a hydrophobic amino acid. The amino acid aggregation inhibitor may be in molar ratio with the antibody as described herein. The amount and selection of aggregation inhibitor, surfactant, tonicity modifier, and buffer is as described above. The disclosure also provides the formulations made by the methods of making, described herein.

A formulation according to the disclosure herein can include pH-adjusting a high-concentration solution of anti-RANKL monoclonal antibody (e.g., denosumab) described herein, e.g. one having a concentration greater than 70 mg/mL, or 120 mg/mL. In another aspect, the formulation can be prepared by pH-adjusting a low-concentration solution of anti-RANKL monoclonal antibody (e.g., denosumab) and then concentrating the solution to the desired, higher final concentration. Suitable pH adjusting agents are known in the art.

Embodiments

The following is a list of specific contemplated embodiments:

1. An aqueous pharmaceutical formulation comprising a human anti-human receptor activator of nuclear factor kappa-B ligand (anti-RANKL) monoclonal antibody or an antigen-binding portion thereof, at a concentration of greater than 70 mg/mL and having a pH in a range of about 5.0 to less than 5.2.

2. The formulation of embodiment 1, having a pH in a range of about 5.0 to 5.19, or about 5.0 to about 5.15, or about 5.0 to about 5.1.

3. The formulation of embodiment 2, having a pH of about 5.1

4. The formulation of any one of embodiments 1 to 3, further comprising an amino acid aggregation inhibitor.

5. An aqueous pharmaceutical formulation comprising a mixture of a human anti-human receptor activator of nuclear factor kappa-B ligand (anti-RANKL) monoclonal antibody or an antigen-binding portion thereof, and an amino acid aggregation inhibitor.

6. The formulation of embodiment 5, having a pH in a range of about 5.0 to about 5.4, or about 5.0 to about 5.2, or about 5.0 to less than 5.2, or about 5.0 to 5.19, or about 5.0 to about 5.15, or about 5.0 to about 5.1.

7. The formulation of embodiment 6, having a pH of about 5.1.

8. The formulation of any one of the preceding embodiments, further comprising a pH buffer.

9. The formulation of any one of embodiments 5 to 8, wherein the concentration of the antibody or antigen-binding portion thereof is in a range of about 10 mg/mL to about 200 mg/mL.

10. The formulation of any one of the preceding embodiments, wherein the concentration of the antibody or antigen-binding portion thereof is in a range of greater than 70 mg/mL to about 200 mg/mL.

11. The formulation of embodiment 10, wherein the concentration of the antibody or antigen-binding portion thereof is in a range of about 100 to about 140 mg/mL.

12. The formulation of embodiment 11, wherein the concentration of the antibody or antigen-binding portion thereof is about 120 mg/mL.

13. The formulation of any one of the preceding embodiments, wherein the antibody is denosumab or a biosimilar thereof.

14. The formulation of embodiment 13, wherein the antibody is denosumab.

15. The formulation of any one of the preceding embodiments, wherein the amino acid aggregation inhibitor is selected from one or more amino acids, dipeptides thereof, or oligopeptides having 2 to 10 residues.

16. The formulation of embodiment 15, wherein the amino acid aggregation inhibitor includes a mixture of at least two amino acids.

17. The formulation of embodiment 16, wherein the amino acids include arginine and phenylalanine.

18. The formulation of any one of the preceding embodiments, wherein the amino acid aggregation inhibitor is selected from one or more hydrophobic amino acids, dipeptides thereof, or oligopeptides having 2 to 10 residues and containing one or more hydrophobic amino acids.

19. The formulation of any one of the preceding embodiments, wherein the amino acid aggregation inhibitor is selected from one or more amino acids carrying a charged side chain, dipeptides thereof, or oligopeptides having 2 to 10 residues and containing one or more amino acids carrying a charged side chain.

20. The formulation of any one of the preceding embodiments, wherein the amino acid aggregation inhibitor is selected from one or more basic amino acids, dipeptides thereof, or oligopeptides having 2 to 10 residues and containing one or more basic amino acids.

21. The formulation of any one of the preceding embodiments, wherein the amino acid aggregation inhibitor is selected from one or more dipeptides.

22. The formulation of any one of the preceding embodiments, wherein the amino acid aggregation inhibitor is selected from one or more oligopeptides having 2 to 10 amino acid residues.

23. The formulation of any one of the preceding embodiments, wherein the amino acid aggregation inhibitor comprises an arginine residue, or the amino acid aggregation inhibitor comprises arginine.

24. The formulation of any one of the preceding embodiments, wherein the amino acid aggregation inhibitor comprises an arginine-phenylalanine dipeptide.

25. The formulation of any one of the preceding embodiments, wherein the amino acid aggregation inhibitor is present in the formulation at a concentration in a range of about 10 mM to about 200 mM.

26. The formulation of any one of the preceding embodiments, further comprising a surfactant.

27. The formulation of embodiment 26, wherein the surfactant is selected from one or more polyoxyethylene sorbitan fatty acid esters (e.g. polysorbate 20, polysorbate 80), or one or more alkylaryl polyethers, e.g. oxyethylated alkyl phenol (e.g. Triton® X-100), or one or more poloxamers (e.g. Pluronics®, e.g. Pluronic® F68), and combinations thereof.

28. The formulation of embodiment 26 or 27, wherein the surfactant is present at a concentration in a range of about 0.004% (w/v) to about 0.1% (w/v).

29. The formulation of embodiment 28, wherein the surfactant is present at a concentration of about 0.01% (w/v).

30. The formulation of any one of the preceding embodiments, further comprising a buffer.

31. The formulation of embodiment 30, wherein the buffer is centered, at 25° C., in a range of about pH 4 to about pH 5.5.

32. The formulation of embodiment 30 or 31, wherein the buffer has a pKa within one pH unit of pH 5.0-5.2 at 25° C.

33. The formulation of any one of embodiments 30 to 32, wherein the buffer comprises acetate.

34. The formulation of any one of embodiments 30 to 32, wherein the buffer comprises glutamate.

35. The formulation of any one of the preceding embodiments, further comprising a tonicity modifier.

36. The formulation of embodiment 35, wherein the tonicity modifier is selected from one or more of sorbitol, mannitol, sucrose, trehalose, glycerol, and combinations thereof.

37. The formulation of embodiment 36, wherein the tonicity modifier comprises sorbitol.

38. The formulation of any one of the preceding embodiments, further comprising one or more additional excipients selected from sugars, polyols, solubilizing agents (e.g. N-Methyl-2-pyrrolidone), hydrophobic stabilizers (e.g., proline), polyethylene glycol, cyclodextrins, and combinations thereof.

39. The formulation of any one of the preceding embodiments, comprising less than 2% high molecular weight species of the human anti-RANKL monoclonal antibody by SE-UHPLC following storage at 37° C. for three months.

40. The formulation of any one of the preceding embodiments, comprising less than 2% high molecular weight species of the human anti-RANKL monoclonal antibody by SE-UHPLC following storage at 4° C. for 36 months.

41. The formulation of any one of the preceding embodiments, comprising at least 98% of the antibody main peak by SE-UHPLC following storage at 37° C. for three months.

42. The formulation of any one of the preceding embodiments, comprising at least 98% of the antibody main peak by SE-UHPLC following storage at 4° C. for 36 months.

43. The formulation of any one of the preceding embodiments, comprising denosumab; an amino acid aggregation inhibitor selected from one or more of arginine, a dipeptide thereof, or an oligomer having 2-10 residues and comprising arginine; an acetate buffer; sorbitol; and a surfactant, and having a pH in a range of about 5.0 to less than 5.2.

44. The formulation of embodiment 43, wherein the amino acid aggregation inhibitor is selected from arginine, arginine-arginine, or arginine-phenylalanine.

45. The formulation of embodiment 43, wherein the amino acid aggregation inhibitor comprises a mixture of arginine and phenylalanine.

46. The formulation of any one of embodiments 43 to 45, wherein the acetate buffer is present in a range of about 5 mM to about 25 mM.

47. The formulation of any one of embodiments 43 to 46, wherein the sorbitol is present in a range of 0.1% (w/v) to 5% (w/v).

48. The formulation of any one of embodiments 43 to 47, wherein the surfactant is selected from one or more of polysorbate 20 and polysorbate 80.

49. The formulation of any one of embodiments 43 to 48, wherein the pH is in a range of about 5.0 to about 5.15.

50. The formulation of embodiment 49, wherein the pH is about 5.10.

51. The formulation of any one of the preceding embodiments, wherein the formulation is suitable for subcutaneous injection.

52. The formulation of any one of the preceding embodiments, wherein the formulation is sterile and preservative-free.

53. The formulation of any one of the preceding embodiments, wherein the human anti-RANKL monoclonal antibody or an antigen-binding portion thereof comprises (1) a heavy chain variable region comprising SEQ ID NO: 2 and a light chain variable region comprising SEQ ID NO: 1; or (2) heavy chain CDR1, CDR2, and CDR3 regions comprising SEQ ID NO: 8, 9, and 10, respectively, and light chain CDR1, CDR2, and CDR3 regions comprising SEQ ID NO: 5, 6, and 7, respectively.

54. The formulation of any one of the preceding embodiments, wherein the human anti-RANKL monoclonal antibody or an antigen-binding portion thereof is an antibody.

55. The formulation of any one embodiments 1-53, wherein the human anti-RANKL monoclonal antibody or an antigen-binding portion thereof is an antigen-binding portion.

56. A vial, pre-filled syringe, or glass container containing a formulation of any one of embodiments 1 to 55.

57. The vial, pre-filled syringe, or glass container of embodiment 56, containing about 1 mL or less of the formulation.

58. A method of preventing a skeletal-related event (SRE) in a patient in need thereof comprising administering an effective amount of a formulation according to any one of embodiments 1 to 55.

59. The method of embodiment 58, wherein the SRE is selected from the group consisting of a pathologic fracture, radiation therapy to bone, surgery to bone, and spinal cord compression.

60. The method of embodiment 58 or 59, wherein the patient has a bone metastasis from a solid tumor.

61. The method of embodiment 60, wherein the solid tumor is selected from breast cancer, prostate cancer, lung cancer, non-small cell lung cancer, and renal cell carcinoma 62. The method of embodiment 58 or 59, wherein the patient has multiple myeloma.

63. The method of any one of embodiments 58 to 62, comprising administering an amount of the formulation effective to reduce the bone turnover marker urinary N-terminal telopeptide corrected for creatinine (uNTx/Cr), optionally by at least 80%.

64. A method of treating giant cell tumor of bone in a patient in need thereof comprising administering an effective amount of a formulation according to any one of embodiments 1 to 55.

65. The method of embodiment 64, wherein the patient has giant cell tumor of bone that is recurrent, unresectable or for which surgical resection is likely to result in severe morbidity.

66. A method of treating hypercalcemia of malignancy in a patient in need thereof comprising administering an effective amount of a formulation according to any one of embodiments 1 to 55.

67. The method of embodiment 66, wherein the malignancy is refractory to bisphosphonate therapy.

68. The method of embodiment 66 or 67, comprising administering an amount of the formulation effective to reduce or maintain the patient's serum calcium at a level less than or equal to about 11.5 mg/dL.

69. The method of any of embodiments 58-68, wherein the formulation comprises the human anti-RANKL antibody at a concentration of about 120 mg/mL.

70. The method of any of embodiments 58-69, comprising administering the formulation on a schedule of once every four weeks.

71. The method of any of embodiments 58-70, comprising administering the formulation on days 8 and 15 of the first month of therapy.

72. A method of treating osteoporosis in a patient in need thereof, comprising administering an effective amount of a formulation according to any one of embodiments 1 to 55.

73. The method of embodiment 72, wherein the patient is a postmenopausal woman at high risk for fracture.

74. The method of embodiment 72, wherein the patient is a man at high risk for fracture.

75. A method of increasing bone mass in a patient in need thereof, comprising administering an effective amount of a formulation according to any one of embodiments 1 to 55.

76. The method of embodiment 75, wherein the patient has osteoporosis.

77. The method of embodiment 75, wherein the patient is a woman at high risk for fracture receiving adjuvant aromatase inhibitor therapy for breast cancer.

78. The method of embodiment 75, wherein the patient is a man at high risk for fracture receiving androgen deprivation therapy for nonmetastatic prostate cancer.

79. The method of any of embodiments 75-78, comprising administering an amount of the formulation effective to decrease the incidence of new vertebral fractures and/or nonvertebral fractures.

80. The method of any of embodiments 75-79, comprising administering an amount of the formulation effective to decrease bone resorption.

81. The method of any of embodiments 75-80, comprising administering an amount of the formulation effective to increase bone density in the patient in at least one area selected from lumbar spine, total hip, and femoral neck.

82. The method of any one of embodiments 75 to 81, comprising administering an amount of the formulation effective to increase bone mass in the patient's cortical bone and/or trabecular bone.

83. The method of any one of embodiments 75 to 82, comprising administering an amount of the formulation effective to reduce the bone resorption marker serum type 1 C-telopetide (CTX).

84. The method of any one of embodiments 75 to 83, comprising administering the formulation on a schedule of once every six months.

85. The method of any one of embodiments 58 to 84, comprising administering the formulation in a volume of 1 mL or less.

86. The method of any one of embodiments 58 to 85, comprising administering the formulation subcutaneously.

87. The method of embodiment 86, comprising administering the formulation subcutaneously to the upper arm, upper thigh, or abdomen.

88. The method of any of embodiments 58 to 87, wherein the patient is receiving one or both of calcium and vitamin D.

89. A method of improving the stability of an aqueous pharmaceutical formulation comprising a human anti-human receptor activator of nuclear factor kappa-B ligand (anti-RANKL) monoclonal antibody or an antigen-binding portion thereof, at a concentration of greater than 70 mg/mL, comprising:

preparing said aqueous pharmaceutical formulation comprising said human anti-human receptor activator of nuclear factor kappa-B ligand (anti-RANKL) monoclonal antibody or an antigen-binding portion thereof at a pH in a range of about 5.0 to less than 5.2, wherein said aqueous pharmaceutical formulation demonstrates improved stability at the pH in a range of about 5.0 to less than 5.2 compared to an equivalent aqueous pharmaceutical formulation that is not at a pH in a range of about 5.0 to less than 5.2.

90. A method of improving the stability of an aqueous pharmaceutical formulation comprising a human anti-human receptor activator of nuclear factor kappa-B ligand (anti-RANKL) monoclonal antibody or an antigen-binding portion thereof comprising:

preparing said aqueous pharmaceutical formulation comprising said human anti-human receptor activator of nuclear factor kappa-B ligand (anti-RANKL) monoclonal antibody or an antigen-binding portion thereof in admixture with an amino acid aggregation inhibitor, wherein said aqueous pharmaceutical formulation demonstrates improved stability with the amino acid aggregation inhibitor compared to an equivalent aqueous pharmaceutical formulation without the amino acid aggregation inhibitor.

EXAMPLES

The following examples are provided for illustration and are not intended to limit the scope of the invention. Throughout the examples presented herein, the following abbreviations are used: DF, diafiltration; PS20, polysorbate 20, HCl, hydrochloride, UF/DF, ultrafiltration/diafiltration; F #, formulation number; HMWS, high molecular weight species; SE-UHPLC, Size Exclusion Ultra High Performance Liquid Chromatography. Additionally, throughout these examples, the composition of the DF buffer or dialysis buffer used to make the final formulation comprising denosumab, as well as estimated concentrations of the components of the final formulation, are provided. The final concentrations of certain components of the final formulations stored and subsequently analyzed for stability can differ from the concentrations of the DF or dialysis buffer depending on the presence or absence of a counterion (e.g., HCl). Without a counterion, formulations have low ionic strength. In such instances, acetate co-concentrates with denosumab, such that final formulations comprise a higher concentration of acetate, relative to the concentration of the DF or dialysis buffer. For example, use of a DF buffer comprising 10 mM acetate leads to ~23 mM acetate in the final denosumab (120 mg/mL) formulation (pH 5.1), when neither the DF buffer nor the final formulation comprises a counterion (e.g., HCl) and thus is of low ionic strength. Similarly, a DF buffer comprising 20 mM acetate leads to ~32 mM acetate in the final denosumab (120 mg/mL) formulation, at pH 5.1, without a counterion (e.g., HCl). When a counterion (e.g., HCl of arginine HCl) is present, acetate does not co-concentrate with denosumab, and therefore the acetate concentration of the DF buffer and the acetate concentration of the final composition are generally equivalent. Additionally, excipients can be volumetrically excluded, or may be impacted by non-specific interactions. For instance, in a 120 mg/mL denosumab formulation, the phenylalanine and sorbitol concentrations are approximately 7-10% lower than what is indicated in the DF buffer and the arginine concentration is approximately 10-15% lower. In view of the foregoing, throughout the following examples concentrations of the components of the final formulations are provided, taking into consideration the above described excipient exclusion and acetate co-concentration effects.

Example 1

An initial evaluation of twelve formulations was made for their effect to minimize the amount (%) of HMWS in a high-concentration liquid denosumab formulation (120 mg/mL), and their formation over time. The formulation alternatives included changes in buffer type, stabilizers, and solution pH. The formulations tested, A-L, are described in the Table 1 below. All buffer values quoted are for the buffer concentration that the antibody is diafiltered against. Each excipient and surfactant was added to the solution post-buffer exchange to the level indicated in the table. While the acetate concentrations in the present formulations were not measured, 120 mg/mL denosumab formulations with sorbitol diafiltered against 10 mM acetate had approximate final acetate values between 25 mM and 35 mM acetate.

Denosumab at 70 mg/mL in acetate, pH 5.2 was UF/DF against 10 mM acetate, pH 5.2 and concentrated to 160 mg/mL. Stock solutions were prepared in 10 mM acetate at pH 5.2 consisting of:
35% sorbitol
1% Polysorbate 20
1% Polysorbate 80
30% Pluronic® F-68
3% Triton™ X-100
250 mM L-Arginine HCl
250 mM N-acetyl arginine (NAR)
250 mM N-acetyl lysine (NAK)
250 mM Proline
250 mM polyethylene glycol (PEG) 3350
250 mM Captisol® cyclodextrin To achieve formulations A to J, the 160 mg/mL material prepared with 10 mM acetate, pH 5.2 was diluted to 120 mg/mL using 10 mM acetate at a pH of 5.2 followed by an addition of the corresponding sorbitol, excipient, and/or surfactant stock solutions to a target final concentration listed in Table 1. To achieve formulations K and L, the self-buffered and glutamate formulations, respectively, two separate aliquots from the 160 mg/mL material underwent additional buffer exchange by centrifugation. The material for formulations K and L was then diluted to 120 mg/mL using the respective buffer followed by an addition of the corresponding sorbitol, and polysorbate 20 stock solutions to a target final concentration listed in the formulation table in Table 1.

TABLE 1

| | Abbreviation | Formulation Composition |
|---|---|---|
| A | Acetate/Sorbitol/PS20/pH 5.2 | 10 mM Acetate, 5% (w/v) Sorbitol, 0.01 (w/v) Polysorbate 20, pH 5.2 |
| B | Acetate/Sorbitol/PS80/pH 5.2 | 10 mM Acetate, 5% (w/v) Sorbitol, 0.01 (w/v) Polysorbate 80, pH 5.2 |
| C | Acetate/Sorbitol/Pluronic F68/pH 5.2 | 10 mM Acetate, 5% (w/v) Sorbitol, 0.01 (w/v) Pluronic F68, pH 5.2 |
| D | Acetate/Sorbitol/Triton X-100/pH 5.2 | 10 mM Acetate, 5% (w/v) Sorbitol, 0.01 (w/v) Triton X-100, pH 5.2 |
| E | Acetate/Arginine/Sorbitol/PS20/pH 5.2 | 10 mM Acetate, 10 mM L-Arginine HCl, 2.4% (w/v) Sorbitol, 0.01 (w/v) Polysorbate 20, pH 5.2 |
| F | Acetate/NAR/Sorbitol/PS20/pH 5.2 | 10 mM Acetate, 10 mM NAR, 3.7% (w/v) Sorbitol, 0.01 (w/v) Polysorbate 20, pH 5.2 |
| G | Acetate/NAK/Sorbitol/PS20/pH 5.2 | 10 mM Acetate, 10 mM NAK, 3.7% (w/v) Sorbitol, 0.01 (w/v) Polysorbate 20, pH 5.2 |

TABLE 1-continued

| | Abbreviation | Formulation Composition |
|---|---|---|
| H | Acetate/Proline/PS20/pH 5.2 | 10 mM Acetate, 10 mM L-proline, 0.01 (w/v) Polysorbate 20, pH 5.2 |
| I | Acetate/PEG/Sorbitol/PS20/pH 5.2 | 10 mM Acetate, 5 mM PEG3350, 5% (w/v) Sorbitol, 0.01 (w/v) Polysorbate 20, pH 5.2 |
| J | Acetate/Captisol/Sorbitol/PS20/pH 5.2 | 10 mM Acetate, 2.7 mM Captisol, 5% (w/v) Sorbitol, 0.01 (w/v) Polysorbate 20, pH 5.2 |
| K | Self-Buffered/Sorbitol/PS20/pH 5.2 | 5% (w/v) Sorbitol, 0.01% (w/v) Polysorbate 20, pH 5.2 |
| L | Glutamate/Arginine/Sorbitol/PS20/pH 5.0 | 10 mM Glutamate, 10 mM L-Arginine HCl, 2.4% (w/v) Sorbitol, 0.01 (w/v) Polysorbate 20, pH 5.0 |

FIG. 1 shows the percent HMWS monitored by SE-UHPLC as a function of formulation and time at 37° C. Formulation L, consisting of approximately 10 mM glutamate buffer, 10 mM L-arginine HCl, 2.4% (w/v) sorbitol as tonicity modifier, 0.01% (w/v) polysorbate 20 as surfactant, and at a pH value of 5.0 showed both decreased starting amounts of HMWS, suggesting some reduction of already-formed aggregates, and decreased kinetics for HMWS formation at 37° C.

Example 2

Evaluation of 10 mM acetate, 75 mM L-arginine, 2.4% (w/v) sorbitol, 0.01% (w/v) polysorbate 20 excipients formulations and a 10 mM acetate, 5% (w/v) sorbitol, 0.01% (w/v) polysorbate 20 excipients formulation, each with high concentration (120 mg/mL) denosumab, at a temperature of 37° C. for up to 1 month revealed the effects of pH and amino acid aggregation inhibitor on the rate and extent of HMWS formation. The formulations tested are described in Table 2 below. All buffer and excipient values quoted are for the buffer and excipient concentrations that the antibody is diafiltered against.

To prepare test samples M-Q, a 3 mL aliquot of denosumab at 70 mg/mL in acetate, pH 5.2 was dialyzed against 500 mL of DF buffer described below, with a total of 3 buffer changes to achieve a 1 million fold dilution of the previous formulation to ensure complete buffer exchange. The material was then over-concentrated using centrifuge-concentrator, followed by a dilution to 120 mg/mL and the addition of polysorbate 20 to a final concentration of 0.01%.

TABLE 2

| | Abbreviation | DF Formulation Composition |
|---|---|---|
| M | Acetate/Arginine/Sorbitol/PS20/pH 4.5 | 10 mM Acetate, 75 mM L-Arginine HCl, 2.4% (w/v) Sorbitol, pH 4.5 |
| N | Acetate/Arginine/Sorbitol/PS20/pH 4.8 | 10 mM Acetate, 75 mM L-Arginine HCl, 2.4% (w/v) Sorbitol, pH 4.8 |
| O | Acetate/Arginine/Sorbitol/PS20/pH 5.2 | 10 mM Acetate, 75 mM L-Arginine HCl, 2.4% (w/v) Sorbitol, pH 5.2 |
| P | Acetate/Sorbitol/PS20/pH 5.2 | 10 mM Acetate, 5% (w/v) Sorbitol, pH 4.5 |
| Q | Acetate/Sorbitol/PS20/pH 5.3 | 10 mM Acetate, 5% (w/v) Sorbitol, pH 4.8 |

Figure 2:
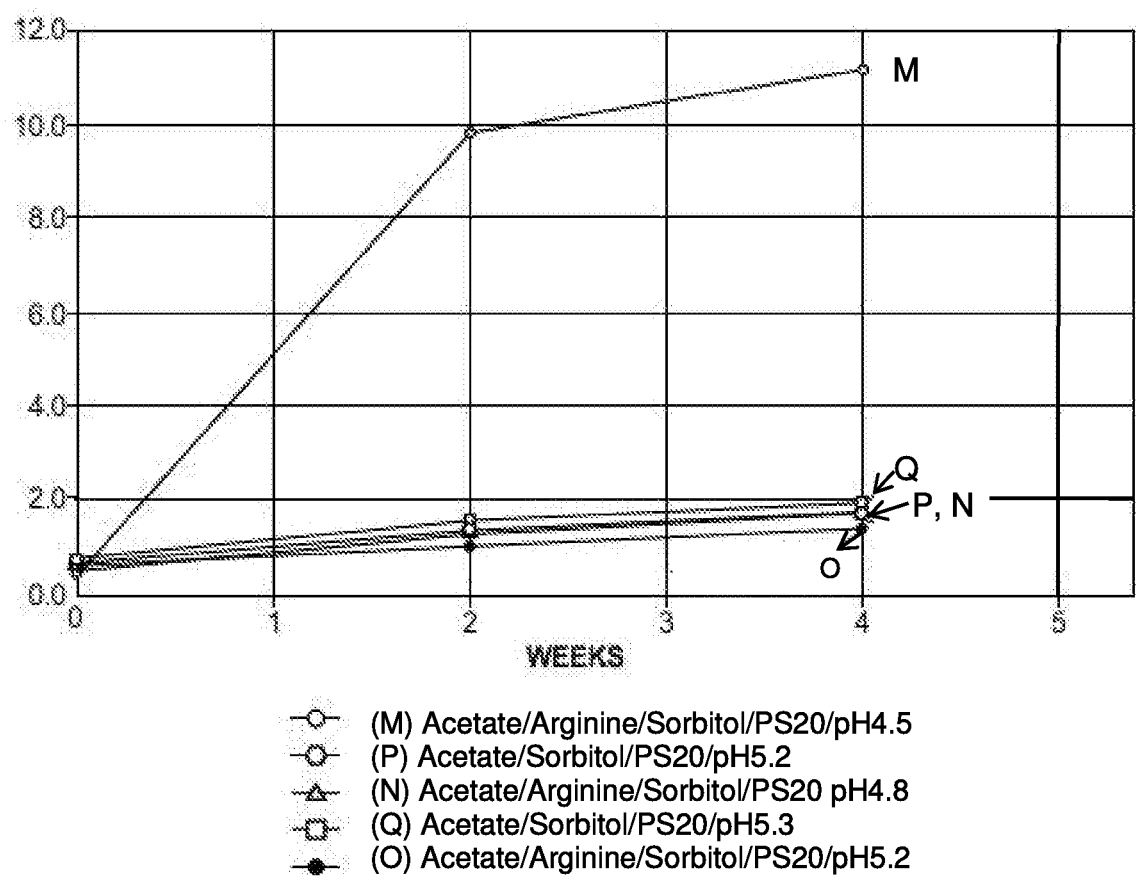
Figure 3:
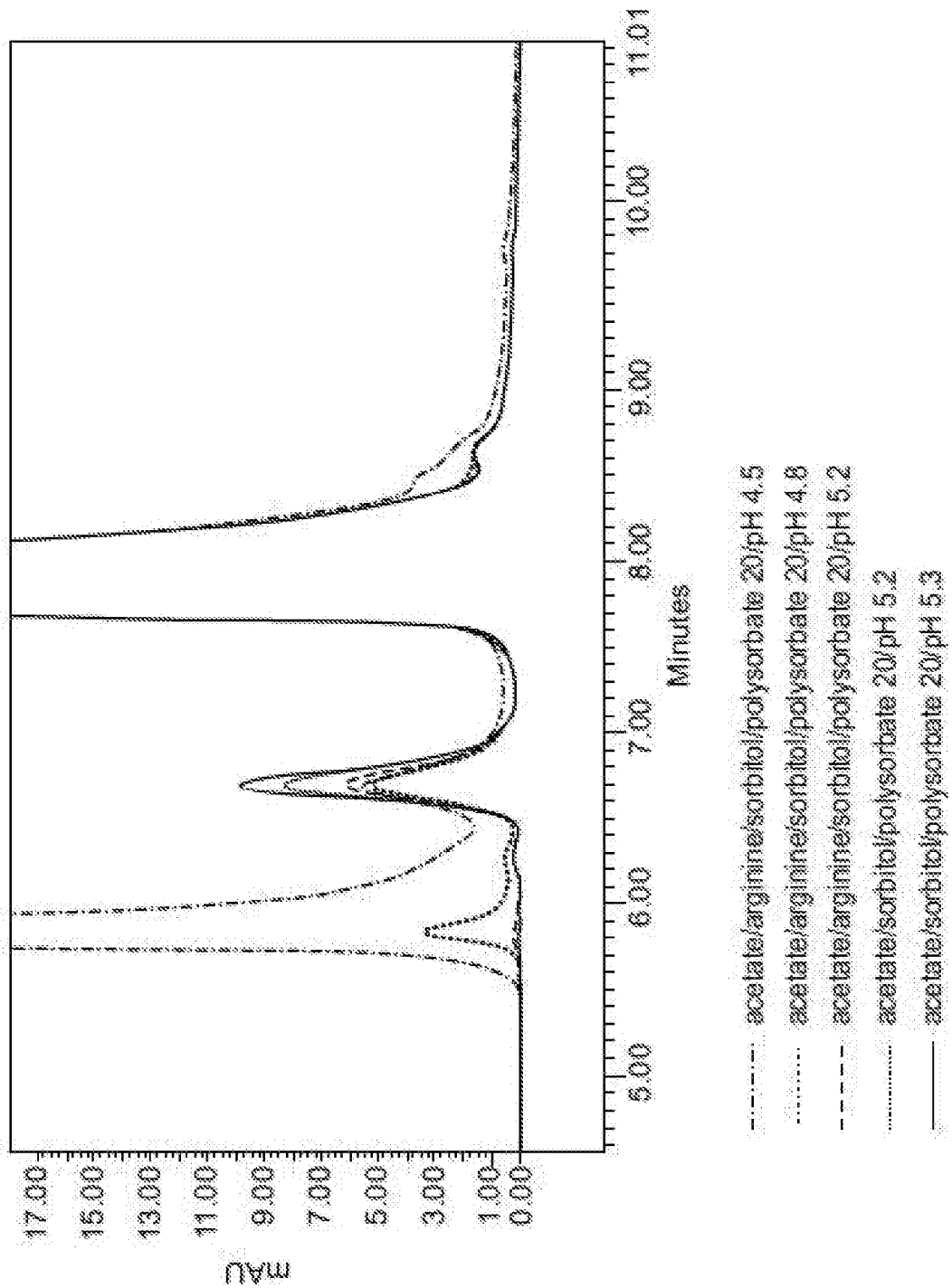
FIG. 3 shows size exclusion chromatograms for various high-concentration denosumab formulations following storage at 37° C. for 1 month. The legend of FIG. 3 accords to the formulation having the Abbreviation shown in Table 2.

FIG. 2 shows the percent HMWS monitored by SE-UHPLC as a function of formulation and time at 37° C. FIG. 3 shows size exclusion chromatograms as a function of formulation following storage at 37° C. for 1 month.

As the solution pH decreased, there was an increase in formation of large aggregates. At pH below 4.8, and especially 4.5, large aggregates were the dominant HWMS, with a dramatic increase for the test formulation at pH 4.5. As shown in FIG. 3, formulations P and Q had the lowest amount of higher order HWMS (retention time about 6 minutes), followed by comparative formulations O, N, and M having decreasing pH values.

However, as the pH was increased, there was generally a resulting increase in the dimer species. As shown in FIG. 3, formulation N had the lowest amount of dimer species (retention time about 6.8 minutes), followed by formulations M, O, P and Q.

The presence of arginine in formulation O at a concentration of 75 mM resulted in approximately 0.3% and 25% reductions in the amounts of the dimer species and its kinetic rate of formation, respectively, after 1 month at 37° C. when compared to formulation P having the same pH, but without arginine.

Example 3

This example demonstrates the effect of pH on high-concentration denosumab formulations.

Denosumab (at a concentration of 120 mg/mL) was formulated with acetate, sorbitol, and polysorbate 20 (PS20) with or without an amino acid aggregation inhibitor at three different pH values: 4.8, 5.1, and 5.4. In this study, the amino acid aggregation inhibitor was L-Arginine HCl. All formulations were made by exchanging the buffer of an initial solution containing a lower concentration of denosumab, followed by over-concentrating the denosumab material and then a diluting the denosumab material with the desired amounts of buffer, excipients, and surfactants. Briefly, an aliquot of denosumab at 70 mg/mL in acetate, pH 5.2 (initial material) was dialyzed against a DF buffer, as described in TABLE 3A, with a total of 3 buffer changes to achieve a 1 million-fold dilution of the initial material to ensure complete buffer exchange. The buffer-exchanged denosumab material was then concentrated using a centrifuge-concentrator to a denosumab concentration of greater than 120 mg/mL, and the concentrated material was subsequently diluted to achieve a concentration of 120 mg/mL denosumab. PS20 was added to a final concentration of 0.01%.

The protein at high concentration was thought to contribute to solution pH based on its charge state. The acetate concentration of Formulation 1 was increased to achieve the targeted final pH, and the acetate concentrations of Formulations 2 and 3 were matched to that of Formulation 1. The acetate concentrations of Formulations 4-6 required an even higher amount of acetate in order to match the final acetate concentrations of Formulations 1-3, due to the acetate not co-concentrating in the presence of the HCl salt. Formulation 7 served as a control to ensure that the increased acetate concentration in Formulations 4-6 did not hinder protein stability in arginine hydrochloride formulations.

The different denosumab formulations made and tested in this study are described in TABLE 3A.

TABLE 3A

| F# | Estimated Final Formulation* | DF Buffer Composition |
|---|---|---|
| 1 | 40 mM Acetate/4.58% (w/v) Sorbitol/PS20/pH 4.8 | 30 mM Acetate, 5% (w/v) Sorbitol, pH 4.35 |
| 2 | 40 mM Acetate/4.58% (w/v) Sorbitol/PS20/pH 5.1 | 30 mM Acetate, 5% (w/v) Sorbitol, pH 4.9 |
| 3 | 40 mM Acetate/4.58% (w/v) Sorbitol/PS20/pH 5.4 | 30 mM Acetate, 5% (w/v) Sorbitol, pH 5.2 |
| 4 | 40 mM Acetate/65 mM Arginine/ 3.3% (w/v) Sorbitol/PS20/pH 4.8 | 40 mM Acetate, 3.6% (w/v) Sorbitol, 75 mM Arginine-HCl, pH 4.8 |
| 5 | 40 mM Acetate/65 mM Arginine/ 3.3% (w/v) Sorbitol/PS20/pH 5.4 | 40 mM Acetate, 3.6% (w/v) Sorbitol, 75 mM Arginine-HCl, pH 5.4 |
| 6 | 40 mM Acetate/65 mM Arginine/ 3.3% (w/v) Sorbitol/PS20/pH 5.1 | 40 mM Acetate, 3.6% (w/v) Sorbitol, 75 mM Arginine-HCl, pH 5.1 |
| 7 | 10 mM Acetate/65 mM Arginine/ 3.3% (w/v) Sorbitol/PS20/pH 5.1 | 10 mM Acetate, 3.6% (w/v) Sorbitol, 75 mM Arginine-HCl, pH 5.1 |

*Final formulations comprised 120 mg/mL denosumab and PS20 at a final concentration of 0.01% (w/v) and had the indicated pH. Sorbitol concentrations are estimated at 8.5% lower than the sorbitol concentration of the DF buffer. Arginine concentrations are estimated at 12.5% lower than the Arginine concentration of the DF buffer.

A sample of each formulation was filled into a container at a fill volume of 1 mL and stored at a temperature of 37° C. for up to 4 weeks. The aggregation inhibition, and stability against aggregation inhibition over time, as based on formation of HMWS and dimer species, was assessed using SE-UHPLC. The aggregation inhibition profiles of these formulations were compared at initial conditions and during and after the storage period.

Figure 4:
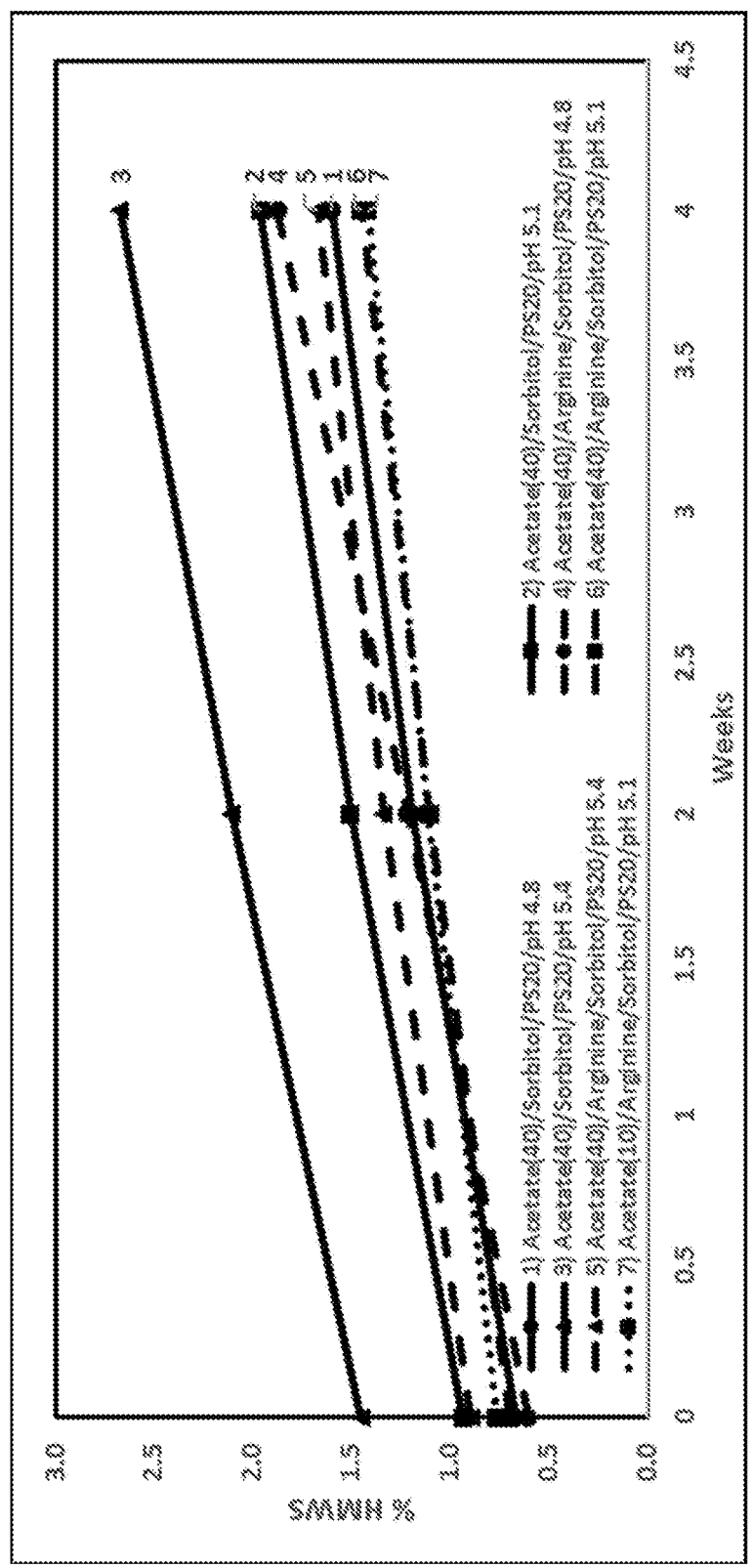
FIG. 4 is a graph of the % HMWS monitored by SE-UHPLC as a function of time for each formulation having the corresponding F # shown in Table 3A.

The percent HMWS was monitored by SE-UHPLC as a function of formulation and time at 37° C. FIG. 4 represents a graph of the percent HMWS as a function of time for Formulations 1-7 and TABLE 3B provides the data points of the graph.

TABLE 3B

| | | Storage Time at 37° C. | | |
|---|---|---|---|---|
| | Formulation Name | 0 weeks | 2 weeks | 4 weeks |
| 1 | Acetate(40)/Sorbitol/PS20/pH 4.8 | 0.7 | 1.2 | 1.6 |
| 2 | Acetate(40)/Sorbitol/PS20/pH 5.1 | 0.9 | 1.5 | 2.0 |
| 3 | Acetate(40)/Sorbitol/PS20/pH 5.4 | 1.5 | 2.1 | 2.7 |
| 4 | Acetate(40)/Arginine/Sorbitol/PS20/pH 4.8 | 0.6 | 1.2 | 1.9 |
| 5 | Acetate(40)/Arginine/Sorbitol/PS20/pH 5.4 | 0.9 | 1.3 | 1.7 |
| 6 | Acetate(40)/Arginine/Sorbitol/PS20/pH 5.1 | 0.7 | 1.1 | 1.4 |
| 7 | Acetate(10)/Arginine/Sorbitol/PS20/pH 5.1 | 0.8 | 1.1 | 1.4 |

F# shown in the left column accords with the F# of Table 3A.

FIG. 5 shows size exclusion chromatograms for each formulation following storage at 37° C. for 1 month. Formulations without arginine are shown in the left panel, while formulations with arginine are shown in the right panel.

Figure 5A:
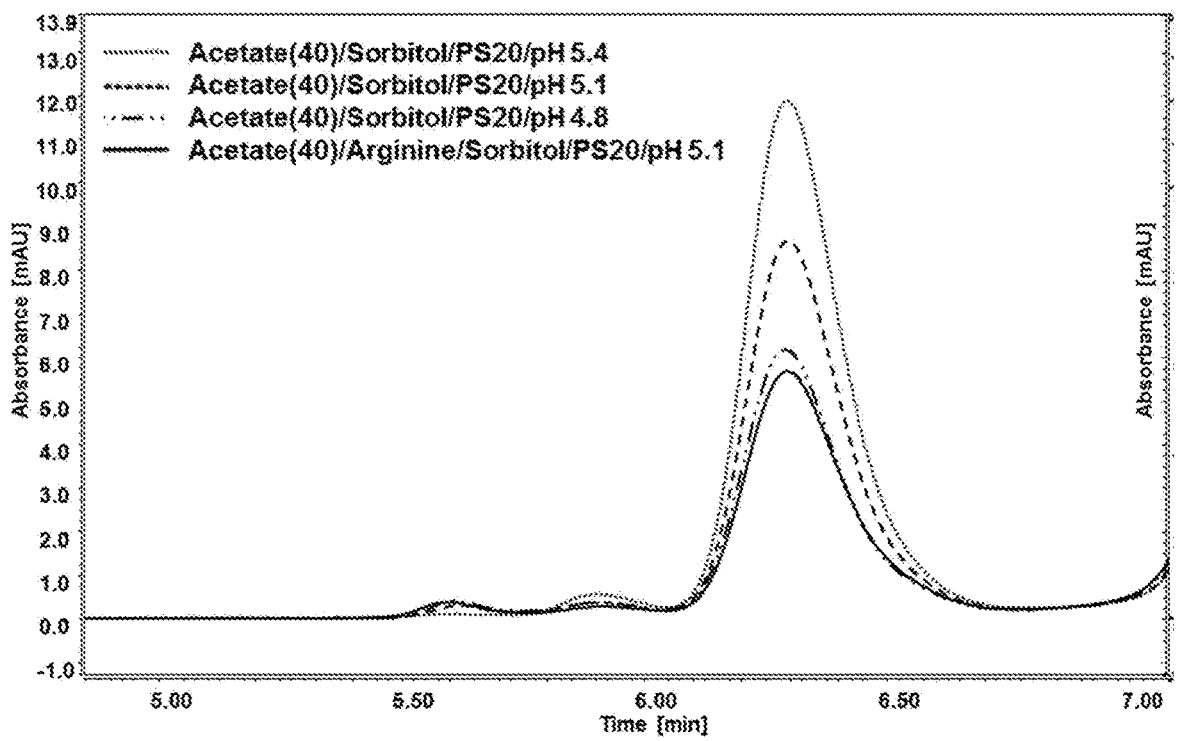
FIGS. 5A and 5B are size exclusion chromatograms for formulations listed in Table 3A. The legend of each of FIGS. 5A and 5B accords to the Formulation Name noted in Table 3B.
Figure 5B:
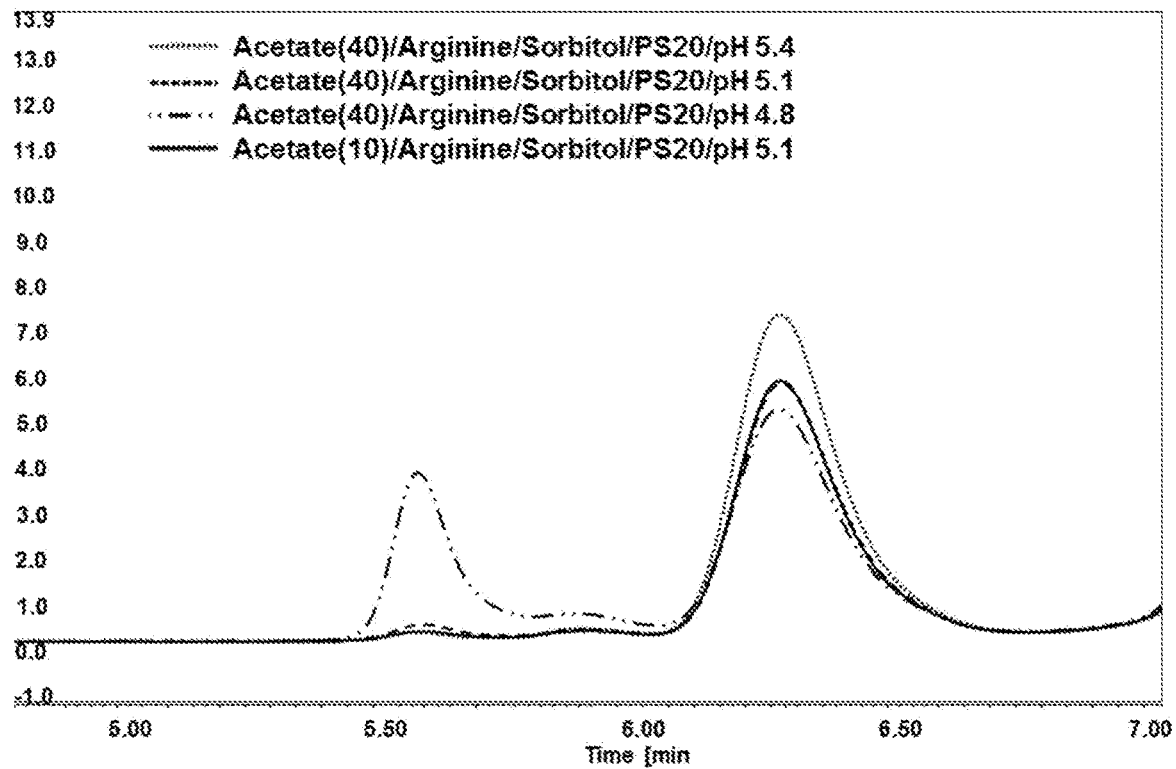

As shown in FIG. 4, formulations containing arginine performed better than the control formulations without arginine hydrochloride, and formulations at pH 5.1 performed better than comparable formulations at pH 4.8 and pH 5.4. For Formulations 1-3 without arginine hydrochloride, the dimer species increased as the solution pH increased to 5.4 (FIG. 5A). For Formulations 4-6 containing arginine hydrochloride, as the solution pH decreased to 4.8, there was an increase in formation of larger aggregates, as well as an increase in the dimer species as the solution pH increased to 5.4 (FIG. 5B). At solution pH of 5.1, Formulation 6 with the presence of arginine hydrochloride, had the lowest amount of total HMWS compared to Formulation 2 without the presence of arginine hydrochloride. Additionally, Formulation 7 behavior demonstrated that an increase in acetate buffer concentration from 10 mM to 40 mM had a relatively smaller effect on the HMWS formation.

Example 4

This example demonstrates a relationship between pH and HMWS formation for different denosumab formulations comprising varying denosumab concentrations.

Denosumab protein concentrations from 15 mg/mL to 150 mg/mL were evaluated to assess pH sensitivity of HMWS formation at various protein concentrations and at concentrations of 75 mM arginine hydrochloride. Two pH values, i.e. pH 4.8 and 5.1, were evaluated at each of the tested protein concentrations: 15, 60, 120 and 150 mg/mL.

A total of 8 formulations (Formulations 8-15; described in TABLE 4A) were evaluated in this study. To prepare these formulations, two aliquots of denosumab at 70 mg/mL in acetate at pH 5.2 was dialyzed against the respective DF buffer described in TABLE 4A. Both dialysis set-up #1 and #2 went through a total of 3 buffer changes to achieve a 1 million-fold dilution of the previous formulation to ensure complete buffer exchange. Post dialysis, aliquots of each dialysis set-up #1 and #2 described in TABLE 4A were removed to prepare dilution step for Formulations 8, 9, 12, and 13. The remaining material was then over-concentrated using centrifuge-concentrator, followed by a dilution to the corresponding denosumab concentrations listed in TABLE 4A and the addition of PS20 to a final concentration of 0.01%.

TABLE 4A

| F# | Estimated Final Formulation* | DF Buffer Composition | Dialysis Set-up |
|---|---|---|---|
| 8 | 15 mg-mL denosumab/Acetate/Arginine/Sorbitol/PS20/pH 4.8 | 10 mM Acetate, 2.4% (w/v) Sorbitol, 75 mM Arginine-HCl, pH 4.8 | 1 |
| 9 | 60 mg-mL denosumab/Acetate/Arginine/Sorbitol/PS20/pH 4.8 | 10 mM Acetate, 2.4% (w/v) Sorbitol, 75 mM Arginine-HCl, pH 4.8 | |
| 10 | 120 mg-mL denosumab/Acetate/Arginine/Sorbitol/PS20/pH 4.8 | 10 mM Acetate, 2.4% (w/v) Sorbitol, 75 mM Arginine-HCl, pH 4.8 | |
| 11 | 150 mg-mL denosumab/Acetate/Arginine/Sorbitol/PS20/pH 4.8 | 10 mM Acetate, 2.4% (w/v) Sorbitol, 75 mM Arginine-HCl, pH 4.8 | |
| 12 | 15 mg-mL denosumab/Acetate/Arginine/Sorbitol/PS20/pH 5.1 | 10 mM Acetate, 2.4% (w/v) Sorbitol, 75 mM Arginine-HCl, pH 5.1 | 2 |
| 13 | 60 mg-mL denosumab/Acetate/Arginine/Sorbitol/PS20/pH 5.1 | 10 mM Acetate, 2.4% (w/v) Sorbitol, 75 mM Arginine-HCl, pH 5.1 | |
| 14 | 120 mg-mL denosumab/Acetate/Arginine/Sorbitol/PS20/pH 5.1 | 10 mM Acetate, 2.4% (w/v) Sorbitol, 75 mM Arginine-HCl, pH 5.1 | |
| 15 | 150 mg-mL denosumab/Acetate/Arginine/Sorbitol/PS20/pH 5.1 | 10 mM Acetate, 2.4% (w/v) Sorbitol, 75 mM Arginine-HCl, pH 5.1 | |

*Final formulations comprised PS20 at a final concentration of 0.01% (w/v) and had the indicated pH. Estimated concentration of acetate was 10 mM, Sorbitol concentrations are estimated at ~8.5% lower than the sorbitol concentration of the DF buffer. Arginine concentrations are estimated at 65 mM. Sorbitol concentrations estimated at 2.2% (w/v).

The formulations were filled into containers at a fill volume of 1 mL and stored at a temperature of 37° C. for up to 1 month. The aggregation inhibition, and stability against aggregation inhibition over time, as based on formation of HMWS and dimer species, was assessed using SE-UHPLC. The aggregation inhibition profiles of these formulations were compared at initial conditions and during and after the storage period.

Figure 6:
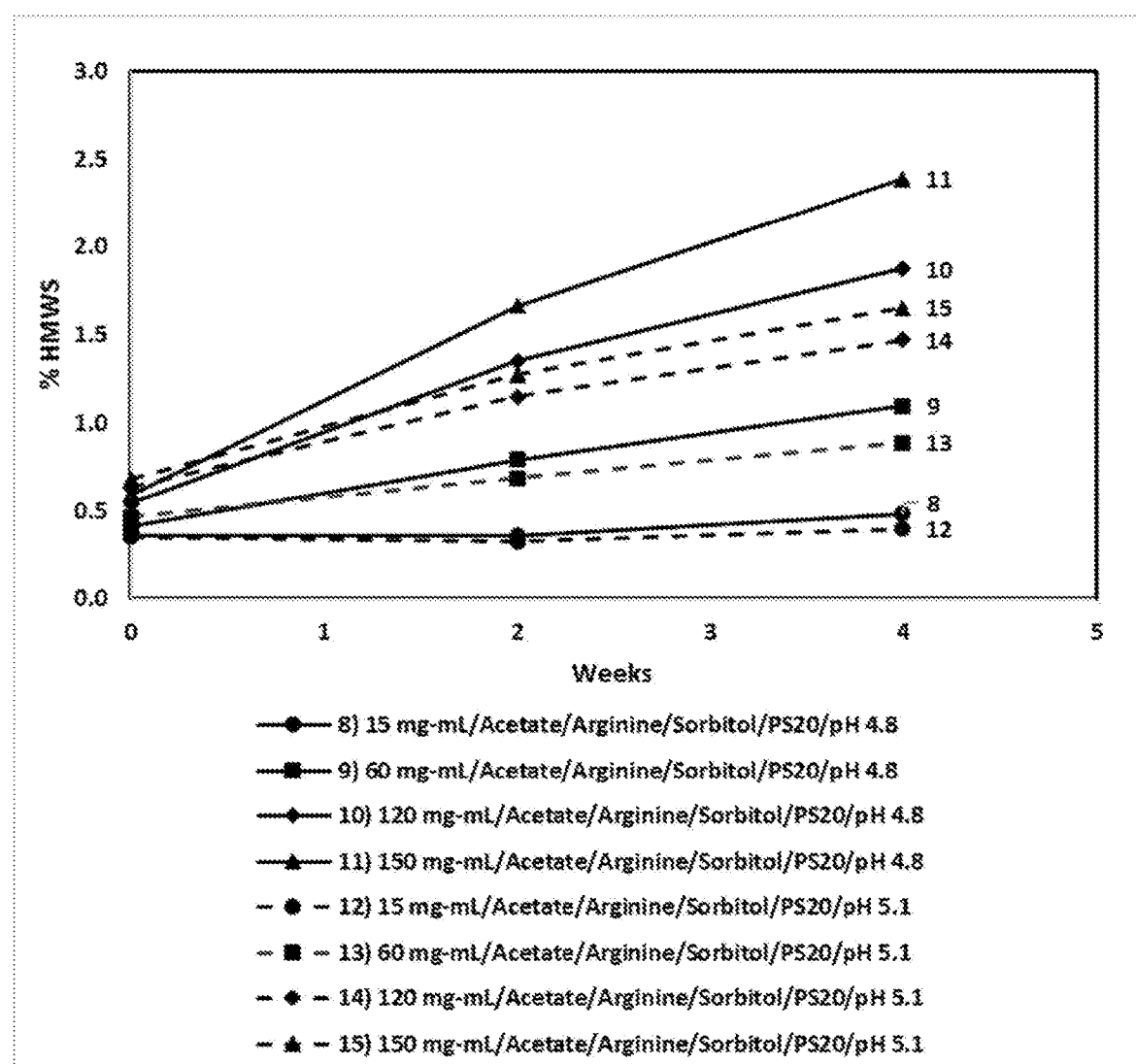
FIG. 6 is a graph of the % HMWS monitored by SE-UHPLC as a function of storage time at 37° C. for each formulation having the corresponding F # shown in Table 4A.

FIG. 6 represents a graph of the percent HMWS monitored by SE-UHPLC as a function of storage time at 37° C. for each formulation and TABLE 4B provides the data points for the graph.

TABLE 4B

| | | Percentage HMWS | |
|---|---|---|---|
| Formulation | 0 | 2 weeks | 4 weeks |
| 8 15 mg-mL/Acetate/Arginine/Sorbitol/PS20/pH 4.8 | 0.4 | 0.4 | 0.5 |
| 9 60 mg-mL/Acetate/Arginine/Sorbitol/PS20/pH 4.8 | 0.4 | 0.8 | 1.1 |
| 10 120 mg-mL/Acetate/Arginine/Sorbitol/PS20/pH 4.8 | 0.5 | 1.4 | 1.9 |
| 11 150 mg-mL/Acetate/Arginine/Sorbitol/PS20/pH 4.8 | 0.6 | 1.7 | 2.4 |
| 12 15 mg-mL/Acetate/Arginine/Sorbitol/PS20/pH 5.1 | 0.4 | 0.3 | 0.4 |
| 13 60 mg-mL/Acetate/Arginine/Sorbitol/PS20/pH 5.1 | 0.5 | 0.7 | 0.9 |
| 14 120 mg-mL/Acetate/Arginine/Sorbitol/PS20/pH 5.1 | 0.6 | 1.2 | 1.5 |
| 15 150 mg-mL/Acetate/Arginine/Sorbitol/PS20/pH 5.1 | 0.7 | 1.3 | 1.7 |

Figure 7A:
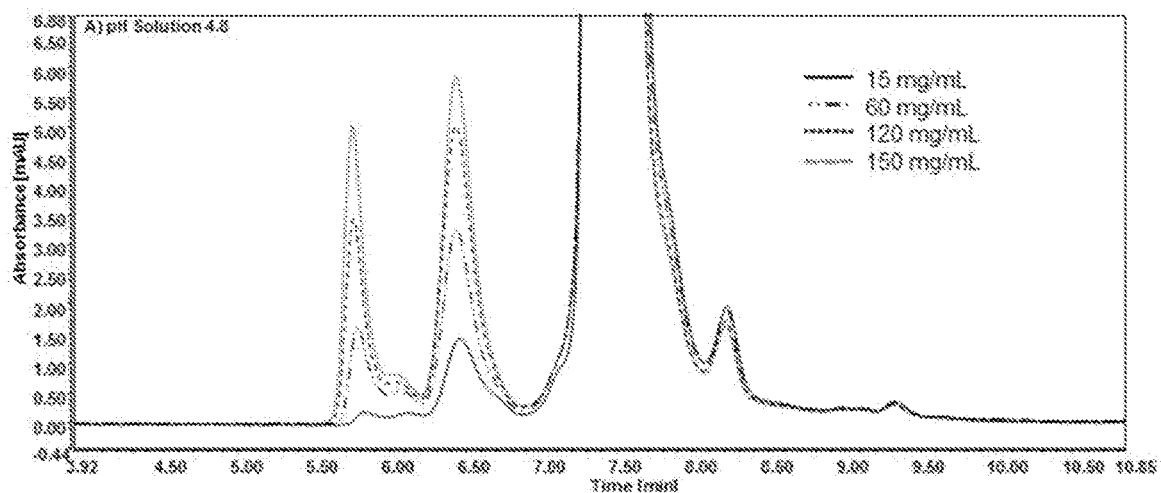
FIG. 7A shows size exclusion chromatograms for formulations at pH 4.8 having the denosumab concentration listed in Table 4A.
Figure 7B:
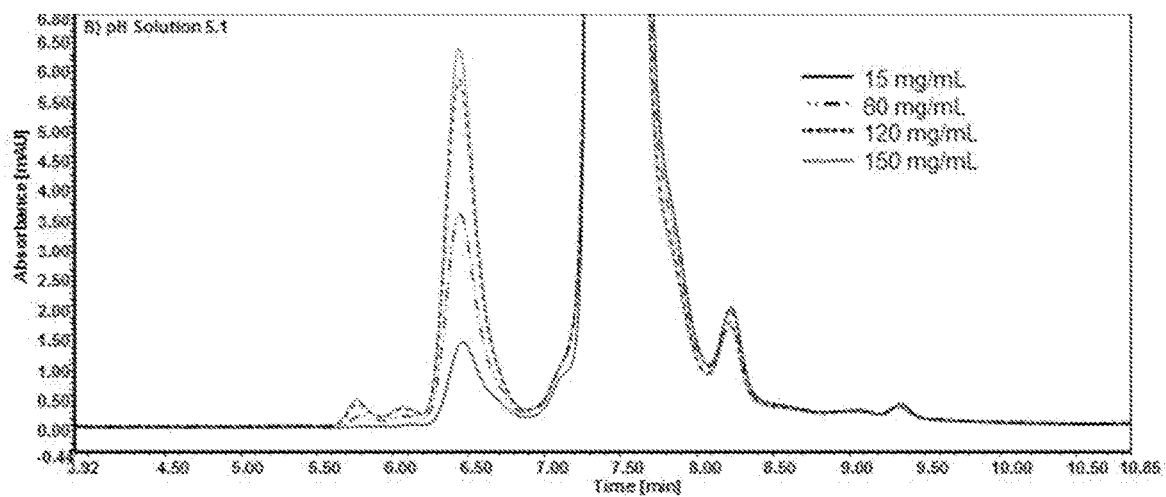
FIG. 7B shows size exclusion chromatograms for formulations at pH 5.1 having the denosumab concentration listed in Table 4A.

FIGS. 7A and 7B show size exclusion chromatograms as a function of formulation following storage at 37° C. for 1 month. As shown in FIG. 6, the % HMWS increased as protein concentration increased. Formulations 8-11 at pH 4.8 consistently had higher levels of HMWS compared to the corresponding formulations at pH 5.1 (Formulations 12-15). The increase in % HMWS at pH 4.8 is due to large aggregate peak shown in FIG. 7A (top) at about 5.75 minutes. While the % HMWS at solution pH 5.1 had increasing dimer species as the protein concentration increased, the total HMWS were lower than the corresponding protein concentrations at solution pH 4.8 (FIG. 7B (bottom)).

The difference in HMWS levels at pH 5.1 vs. pH 4.8 became greater as the denosumab concentration increased, with the difference being greater at higher concentrations of denosumab.

Example 5

Formulations with various concentrations of arginine, NAR, and two dipeptides consisting of arginine-arginine (Arg-Arg) and arginine-phenylalanine (Arg-Phe) were evaluated for stabilizing effects on solutions having a denosumab concentration of 120 mg/mL.

The formulations tested are described in TABLE 5 below. All acetate and excipient (except dipeptides) values quoted are for the buffer and excipient concentrations that the antibody is diafiltered against. Each dipeptide was added to the solution post-buffer exchange to the level indicated in the table. Formulations R to X were achieved by UF/DF against the DF buffer listed below. Formulations Y and Z were achieved by UF/DF, together in a single pool, against DF buffer containing 10 mM acetate, 3.6% sorbitol, pH 4.0. Post UF/DF, the pool for formulations Y and Z were split into 2, and Arg-Arg or Arg-Phe dipeptides were then spiked in from a 1 M stock solution containing 3.6% sorbitol at pH 5.1. Polysorbate 20 was added to each formulation at a final target concentration of 0.01%. Acetate co-concentrates without arginine, resulting in a final acetate concentration of about 25 mM in formulations S to X. Sorbitol is preferentially excluded in the concentration process, resulting in a reduction of about 7 to 8% (w/v) from initial concentration.

The formulations were filled into containers at a fill volume of 1.0 mL. The formulations are stored at temperatures of 2° C. to 8° C. for up to 12 months and 25° C., 30° C., and 37° C. for 3 months. The stability as based on formation of HMWS is assessed using SE-UHPLC. The stability of these dipeptide formulations after one month at 37° C. were compared with arginine hydrochloride formulations at 37° C. as shown in FIG. 8.

TABLE 5

| Estimated Final Formulation | DF Formulation Composition |
|---|---|
| R Acetate/5% Sorbitol/PS20/pH 5.1 | 10 mM Acetate, 5% (w/v) Sorbitol, pH 4.0 |
| S Acetate/3.6% Sorbitol/38 mM Arg-HCl/PS20/pH 5.2 | 10 mM Acetate, 3.6% (w/v) Sorbitol, 38 mM L-Arginine HCl, pH 5.1 |
| T Acetate/2.4% Sorbitol/75 mM Arg-HCl/PS20/pH 5.2 | 10 mM Acetate, 2.4% (w/v) Sorbitol, 75 mM L-Arginine HCl, pH 5.1 |
| U 18 mM Acetate/2.4% Sorbitol/75 mM Arg-HCl/PS20/pH 5.2 | 18 mM Acetate, 2.4% (w/v) Sorbitol, 75 mM L-Arginine HCl, pH 5.1 |
| V Acetate/1.2% Sorbitol/113 mM Arg-HCl/PS20/pH 5.2 | 10 mM Acetate, 1.2% Sorbitol, 113 mM L-Arginine HCl, pH 5.1 |
| W Acetate/0% Sorbitol/150 mM Arg-HCl/PS20/pH 5.1 | 10 mM Acetate, 0% (w/v) sorbitol, 150 mM L-Arginine HCl, pH 5.1 |
| X Acetate/150 mM NAR/75 mM Arg-HCl/PS20/pH 5.2 | 10 mM Acetate, 75 mM L-Arginine HCl, 150 mM NAR, pH 5.1 |
| Y Acetate/3.6% Sorbitol/38 mM Arg-Arg/PS20/pH 5.1 | 10 mM Acetate, 3.6% (w/v) Sorbitol, pH 4.0 |
| Z Acetate/3.6% Sorbitol/38 mM Arg-Phe/PS20/pH 5.2 | 10 mM Acetate, 3.6% (w/v) Sorbitol, pH 4.0 |

Figure 8:
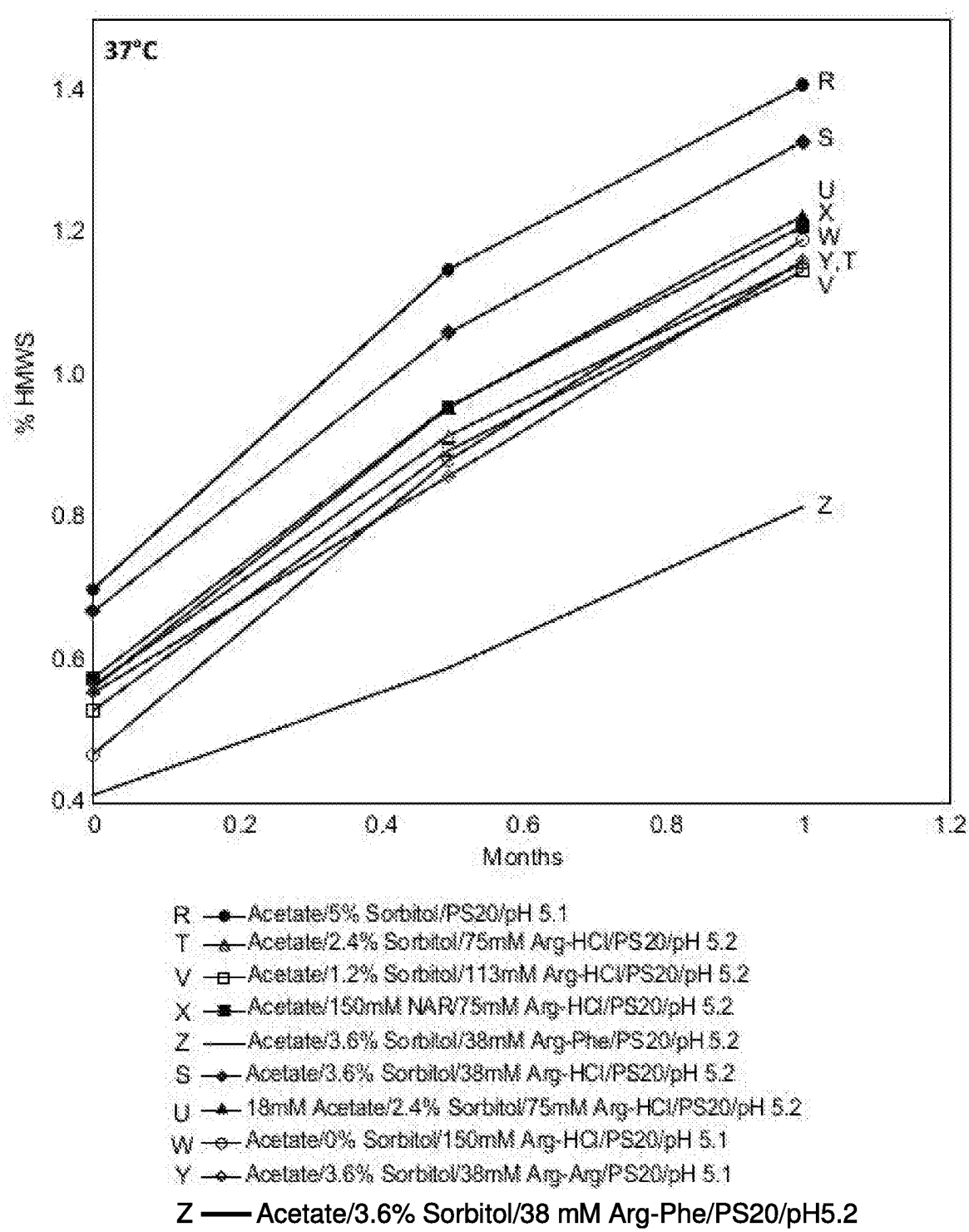

FIG. 8 shows percent HMWS monitored by SE-UHPLC as a function of formulation and time at 37° C. The results show that amino acid aggregation inhibitors inhibited formation of HMWS. The arginine-phenylalanine dipeptide, for example, showed a significant improvement, resulting in about 0.3% less HMWS compared to the other formulations. The rank order of lowest to highest HMWS was Z<<V<Y≈T≈W≈X≈U<S<R. As can be seen in the figure, both the arginine-arginine (Arg-Arg) (formulation Y) and arginine-phenylalanine (Arg-Phe) (formulation Z) dipeptide-containing formulations reduced HMWS formation compared to the control formulation lacking arginine and lacking arginine-containing dipeptides (formulation R). Formulation Z contained the least amount of HMWS, superior to formulation Y.

Example 6

This example demonstrates the aggregation inhibition and stability of denosumab as a function of different concentrations of arginine and phenylalanine, and a comparative mixture of arginine and phenylalanine.

As described above, arginine hydrochloride (HCl) and arginine HCl-phenylalanine dipeptides were identified to reduce the initial starting level and rate of HMWS formation of denosumab. In this study, formulations containing concentrations of arginine HCl, concentrations of phenylalanine, and a combination of arginine HCl and phenylalanine were evaluated for the stabilizing effects on solutions containing denosumab at 120 mg/mL.

The tested formulations (Formulations 16-20) are described in TABLE 6A below. To prepare these formulations, an aliquot of denosumab at 70 mg/mL in acetate, pH 5.2 was dialyzed against the DF buffer described in TABLE 6A, with a total of 3 buffer changes to achieve a 1 million fold dilution of the previous formulation to ensure complete buffer exchange. The material was then over-concentrated using centrifuge-concentrator, followed by a dilution to 120 mg/mL and the addition of polysorbate 20 to a final concentration of 0.01%. Formulation 16 was considered the control formulation.

TABLE 6A

| | Estimated Final Formulation* | DF Buffer Composition |
|---|---|---|
| 16 | 23 mM Acetate/4.6%(w/v) Sorbitol/PS20/pH 5.1 | 10 mM Acetate, 5% (w/v) Sorbitol, pH 4.0 |
| 17 | 10 mM Acetate/65 mM Arginine/2.2%(w/v) Sorbitol/PS20/pH 5.1 | 10 mM Acetate, 75 mM L-Arginine HCl, 2.4% (w/v) Sorbitol, pH 5.1 |
| 18 | 23 mM Acetate/35 mM Phenylalanine/4%(w/v) Sorbitol/PS20/pH 5.1 | 10 mM Acetate, 38 mM Phenylalanine, 4.4% (w/v) Sorbitol, pH 4.0 |
| 19 | 23 mM Acetate/68 mM Phenylalanine/3.3%(w/v) Sorbitol/PS20/pH 5.1 | 10 mM Acetate, 75 mM Phenylalanine, 3.6% (w/v) Sorbitol, pH 4.0 |
| 20 | 10 mM Acetate/33 mM Arginine/35 mM Phenylalanine/2.2% (w/v) Sorbitol/PS20/pH 5.1 | 10 mM Acetate, 38 mM Arginine HCl, 38 mM Phenylalanine, 2.4% (w/v) Sorbitol, pH 5.1 |

*Final formulations comprised 120 mg/mL denosumab and PS20 at a final concentration of 0.01% (w/v) and had the indicated pH. Sorbitol and phenylalanine concentrations are estimated at ~8.5% lower than the concentration of the DF buffer. Arginine concentrations are estimated at ~12.5% lower than the concentration of the DF buffer.

The formulations were filled into containers at a fill volume of 1.0 mL. The formulations were stored at a temperature of 37° C. for up to 1 month. The aggregation inhibition, and stability against aggregation inhibition over time, as based on formation of HMWS and dimer species, was assessed using SE-UHPLC. The aggregation inhibition profiles of these formulations were compared at initial conditions and during and after the storage period.

Figure 9:
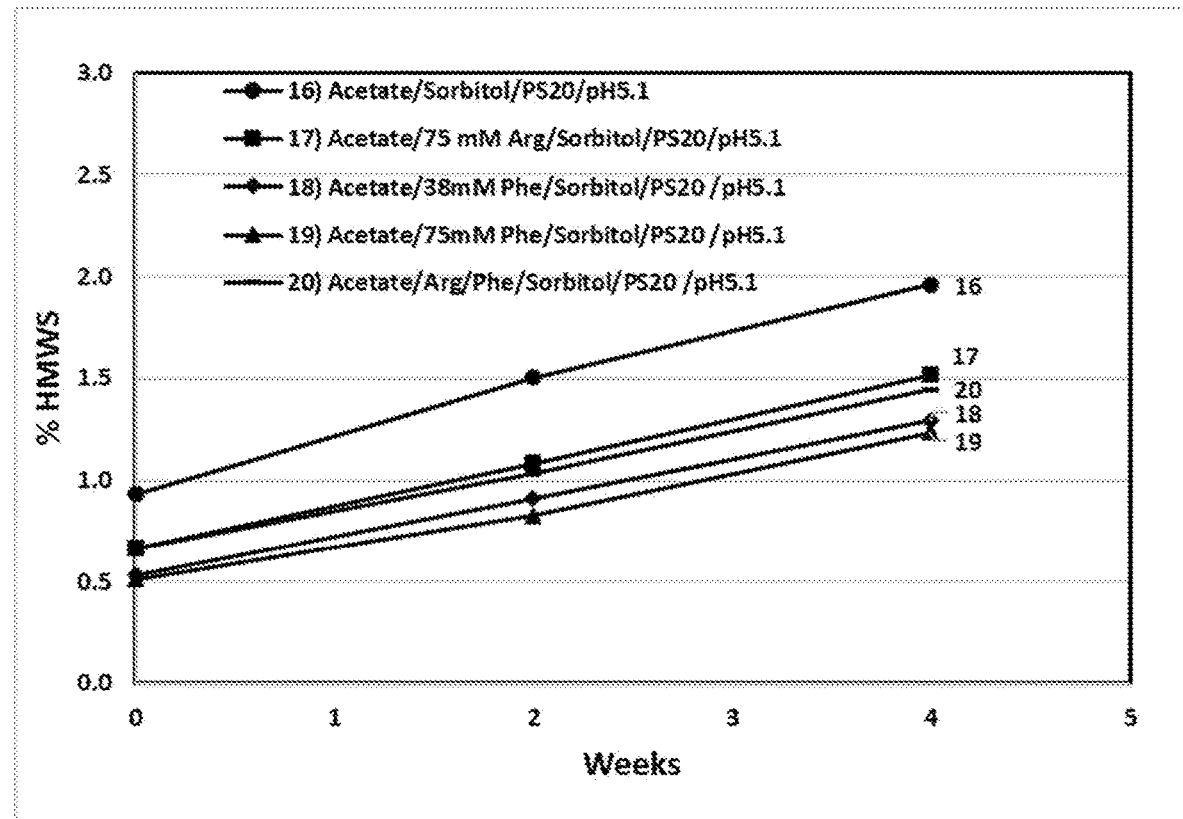
FIG. 9 is a graph of the % HMWS monitored by SE-UHPLC as a function of storage time at 37° C. for each formulation having the corresponding F # shown in Table 6B.
Figure 10:
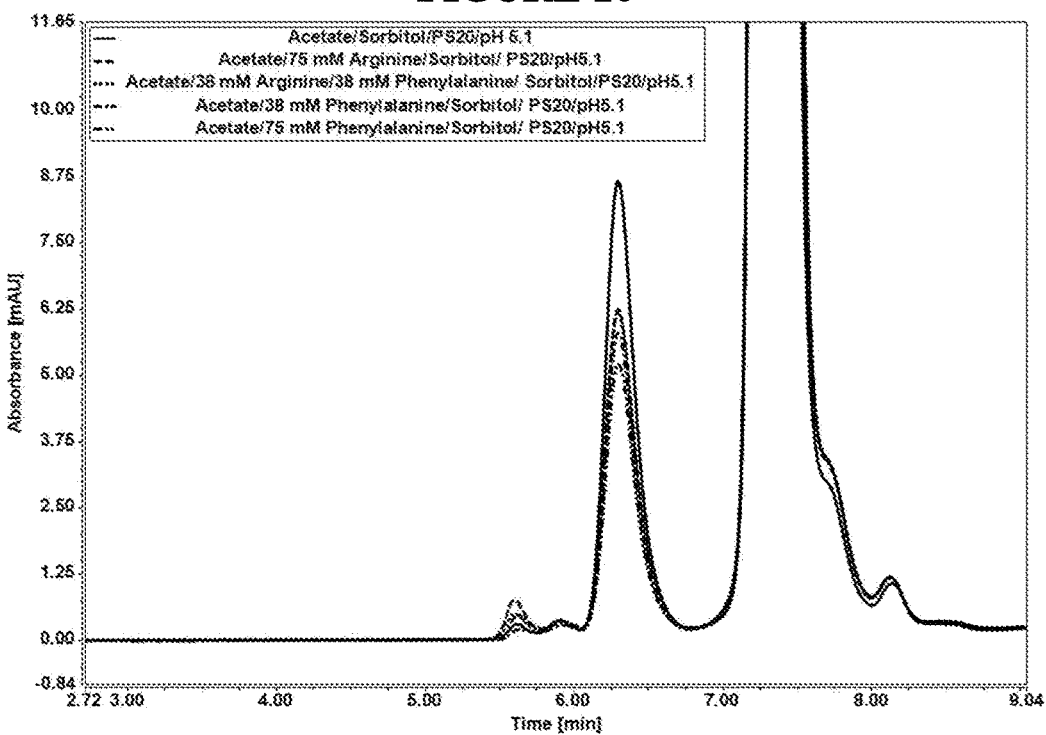
FIG. 10 shows size exclusion chromatograms as a function of formulation following storage at 37° C. for 1 month for the formulations having name indicated in Table 6B.

FIG. 9 shows the percent HMWS monitored by SE-UHPLC as a function of formulation and time at 37° C. FIG. 10 shows size exclusion chromatograms as a function of formulation following storage at 37° C. for 1 month. TABLE 6B below shows show the percent HMWS monitored by SE-UHPLC as a function of formulation and time at 37° C.

TABLE 6B

| | | Percentage HMWS | | |
|---|---|---|---|---|
| | Formulation | 0 | 2 weeks | 4 weeks |
| 16 | Acetate/Sorbitol/PS20/pH 5.1 | 0.9 | 1.5 | 2.0 |
| 17 | Acetate/75 mM Arginine/Sorbitol/PS20/pH 5.1 | 0.7 | 1.1 | 1.5 |
| 18 | Acetate/38 mM Phenylalanine/Sorbitol/PS20/pH 5.1 | 0.5 | 0.9 | 1.3 |
| 19 | Acetate/75 mM Phenylalanine/Sorbitol/PS20/pH 5.1 | 0.5 | 0.8 | 1.2 |
| 20 | Acetate/38 mM Arginine/38 mM Phenylalanine/Sorbitol/PS20/pH 5.1 | 0.7 | 1.0 | 1.4 |

All formulations comprising an amino acid aggregation inhibitor, arginine or phenylalanine (Formulations 17-20), were superior to the sorbitol control formulation lacking any amino acid aggregation inhibitor (Formulation 16). All phenylalanine-containing formulations (Formulations 18, 19, and 20) similarly contained low levels of HMWS, when compared to both the control and arginine HCl formulations (Formulations 16 and 17, respectively) (FIG. 9). The rate of HMWS formation was similar across the arginine HCl and phenylalanine containing formulations (Formulations 17-19), as shown in FIG. 9. The combination formulation comprising both 38 mM arginine and 38 mM phenylalanine (total 76 nM, Formulation 20) demonstrated a stability better than the 75 mM arginine formulation (Formulation 17) (FIG. 9), but not better than the 75 mM phenylalanine formulation (formulation 19) (FIG. 9).

Example 7

This example demonstrates the aggregation inhibition and stability of denosumab as a function of different concentrations of phenylalanine.

In previous studies, arginine hydrochloride and arginine hydrochloride-phenylalanine dipeptides were identified to minimize the initial starting level and rate of HMWS formation of denosumab. Formulations containing arginine hydrochloride, various concentrations of phenylalanine, and a combination of arginine hydrochloride and phenylalanine were evaluated for stabilizing effects on solutions containing denosumab at 120 mg/mL.

The formulations tested are described in Table 7A below. To prepare test samples A-E, an aliquot of denosumab at 70 mg/mL in acetate, pH 5.2 was dialyzed against the DF buffers described below, with a total of 3 buffer changes to achieve a 1 million fold dilution of the previous formulation to ensure complete buffer exchange. The material was then over concentrated to approximately 130 mg/mL to 150 mg/mL using centrifuge-concentrator, followed by a dilution to 120 mg/mL and the addition of polysorbate 20 to a final concentration of 0.01%. Formulation A was considered the control formulation.

Figure 11A:
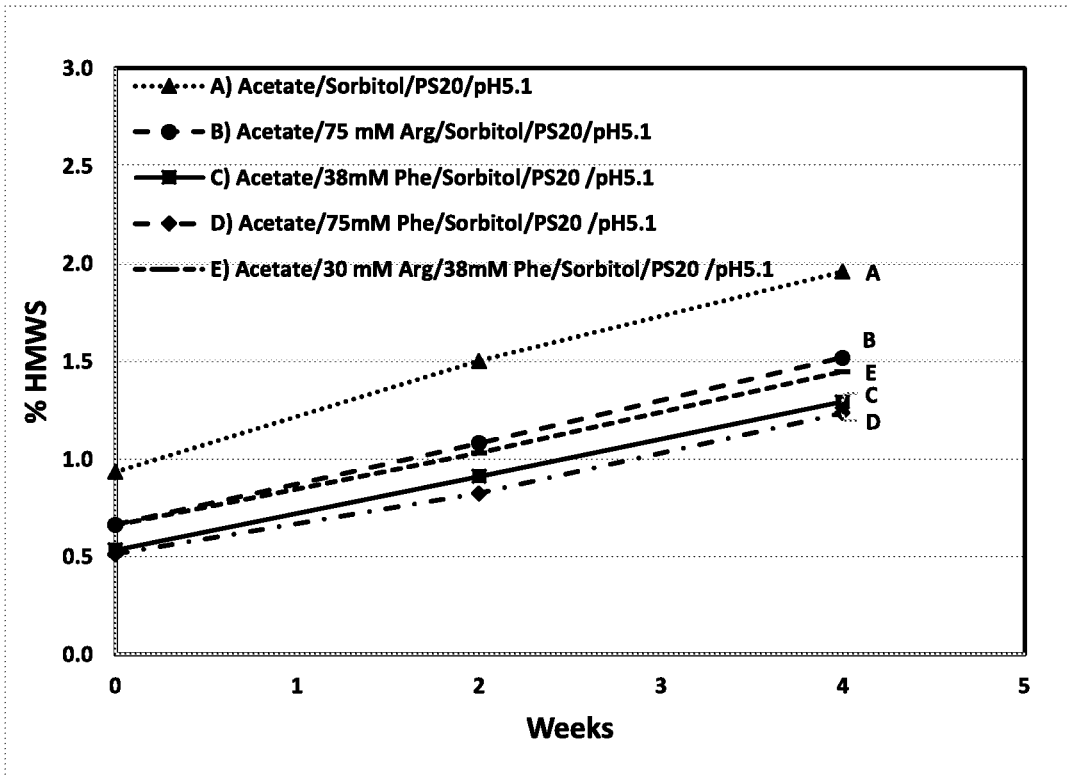
FIG. 11A is a graph of the percent HMWS monitored by SE-UHPLC as a function of time at 37° C. for the formulation having the letter indicated in Table 7B.

The formulations were filled into containers at a fill volume of 1.0 mL. The formulations were stored at a temperature of 37° C. for up to 1 month. The stability as based on formation of HMWS was assessed using SE-UHPLC. The stability profiles of these formulations were compared after one month at 37° C. with the sorbitol and arginine hydrochloride/sorbitol formulations at 37° C. as shown in FIG. 11A.

To prepare test samples F-K, an aliquot of denosumab at 70 mg/mL in acetate, pH 5.2 was ultrafiltered/diafiltered (UF/DF) against the DF buffers described below for a total 12 diavolumes to ensure complete buffer exchange. The material was then over concentrated to approximately 200 mg/mL using ultrafiltration, followed by a dilution to 120 mg/mL and the addition of polysorbate 20 to a final concentration of 0.01%. The acetate concentration was 20 mM in these formulations. Formulation F was considered the control formulation. All acetate and excipient values quoted are for the buffer and excipient concentrations that the antibody are dialyzed against.

Figure 11B:
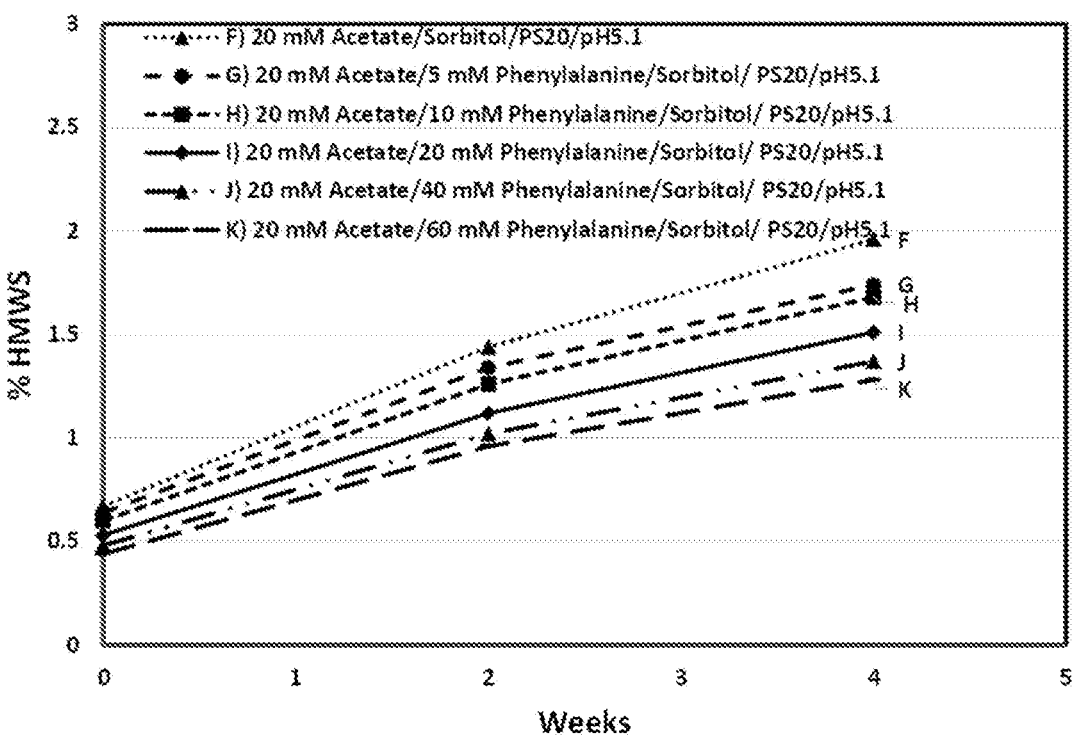
FIG. 11B is a graph of the percent HMWS monitored by SE-UHPLC as a function of time at 40° C. for the formulation having the letter indicated in Table 7C.

The formulations were filled into containers at a fill volume of 1.0 mL. The formulations were stored at a temperature of 40° C. for up to 1 month. The stability as based on formation of HMWS was assessed using SE-UHPLC. The stability profiles of these formulations were compared after one month at 40° C. with the sorbitol and arginine hydrochloride/sorbitol formulations at 40° C. as shown in FIG. 11B.

TABLE 7A

| F# | Estimated Final Formulation | DF Buffer Composition* |
|---|---|---|
| A | 23 mM Acetate/4.6% (w/v) Sorbitol/PS20/pH 5.1 | 10 mM Acetate, 5% (w/v) Sorbitol, pH 4.0 |
| B | 10 mM Acetate/65 mM Arginine/ 2.2% (w/v) Sorbitol/PS20/pH 5.1 | 10 mM Acetate, 75 mM L-Arginine HCl, 2.4% (w/v) Sorbitol, pH 5.1 |
| C | 23 mM Acetate/35 mM Phenylalanine/4.0% (w/v) Sorbitol/PS20/pH 5.1 | 10 mM Acetate, 38 mM Phenylalanine, 4.4% (w/v) Sorbitol, pH 4.0 |

TABLE 7A-continued

| F# | Estimated Final Formulation | DF Buffer Composition* |
|---|---|---|
| D | 23 mM Acetate/69 mM Phenylalanine/3.3% (w/v) Sorbitol/PS20/pH 5.1 | 10 mM Acetate, 75 mM Phenylalanine, 3.6% (w/v) Sorbitol, pH 5.1 |
| E | 10 mM Acetate/33 mM Arginine/ 35 mM Phenylalanine/2.2% (w/v) Sorbitol/PS20/pH 5.1 | 10 mM Acetate, 38 mM Arginine HCl, 38 mM Phenylalanine, 2.4% (w/v) Sorbitol, pH 5.1 |
| F | 23 mM Acetate/4.3% (w/v) Sorbitol/PS20/pH 5.1 | 20 mM Acetate, 4.7% (w/v) Sorbitol, pH 4.0 |
| G | 23 mM Acetate/4.6 mM Phenylalanine/4.3% (w/v) Sorbitol/PS20/pH 5.1 | 20 mM Acetate, 5 mM Phenylalanine, 4.7% (w/v) Sorbitol, pH 4.0 |
| H | 23 mM Acetate/9 mM Phenylalanine/4.3% (w/v) Sorbitol/PS20/pH 5.1 | 20 mM Acetate, 10 mM Phenylalanine, 4.7% (w/v) Sorbitol, pH 4.0 |
| I | 23 mM Acetate/18 mM Phenylalanine/4.3% (w/v) Sorbitol/PS20/pH 5.1 | 20 mM Acetate, 20 mM Phenylalanine, 4.7% (w/v) Sorbitol, pH 4.0 |
| J | 32 mM Acetate/37 mM Phenylalanine/4.3% (w/v) Sorbitol/PS20/pH 5.1 | 20 mM Acetate, 40 mM Phenylalanine, 4.7% (w/v) Sorbitol, pH 4.0 |
| K | 32 mM Acetate/55 mM Phenylalanine/4.3% (w/v) Sorbitol/PS20/pH 5.1 | 20 mM Acetate, 60 mM Phenylalanine, 4.7% (w/v) Sorbitol, pH 4.0 |

*Final formulations comprised 120 mg/mL denosumab and PS20 at a final concentration of 0.01% (w/v) and had the indicated pH. Sorbitol and phenylalanine concentrations are estimated at ~8.5% lower than the concentration of the DF buffer. Arginine concentrations are estimated at ~12.5% lower than the concentration of the DF buffer.

Figure 12A:
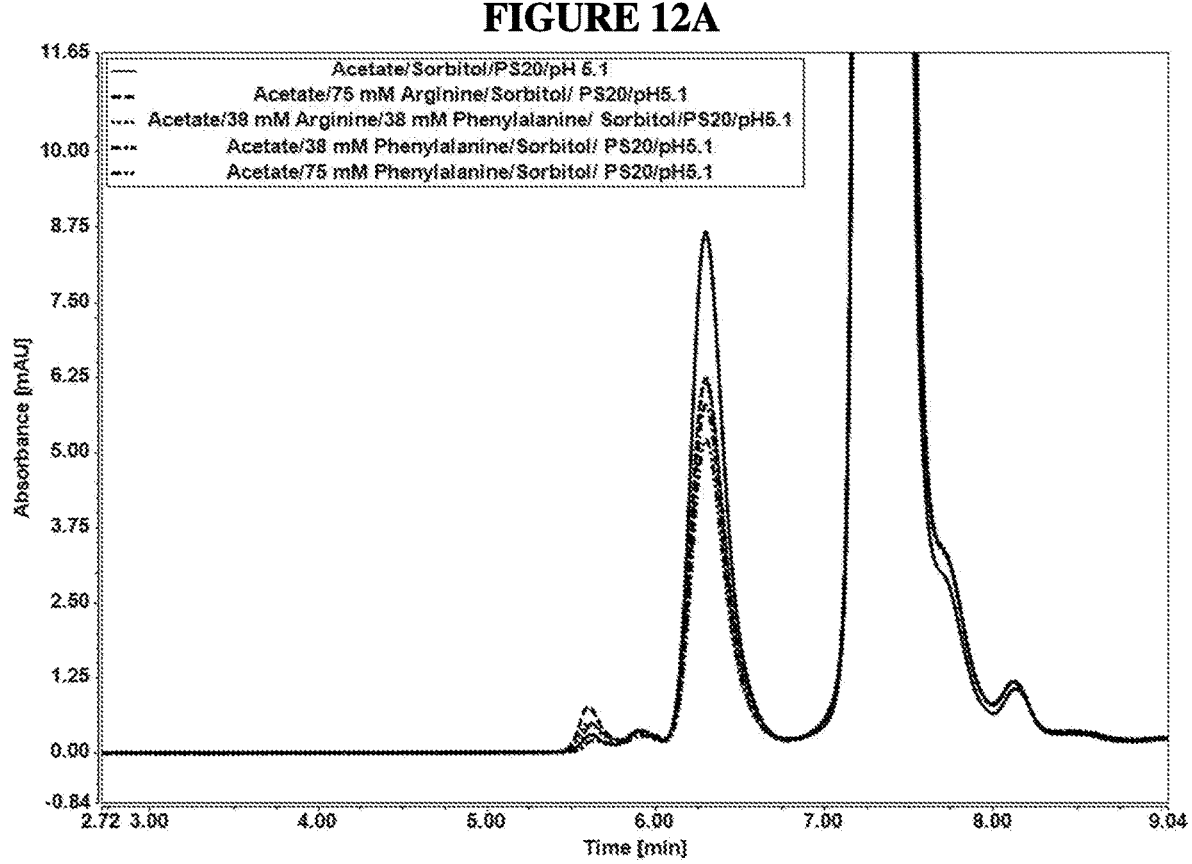
FIG. 12A show size exclusion chromatograms for formulations of Table 7B.
Figure 12B:
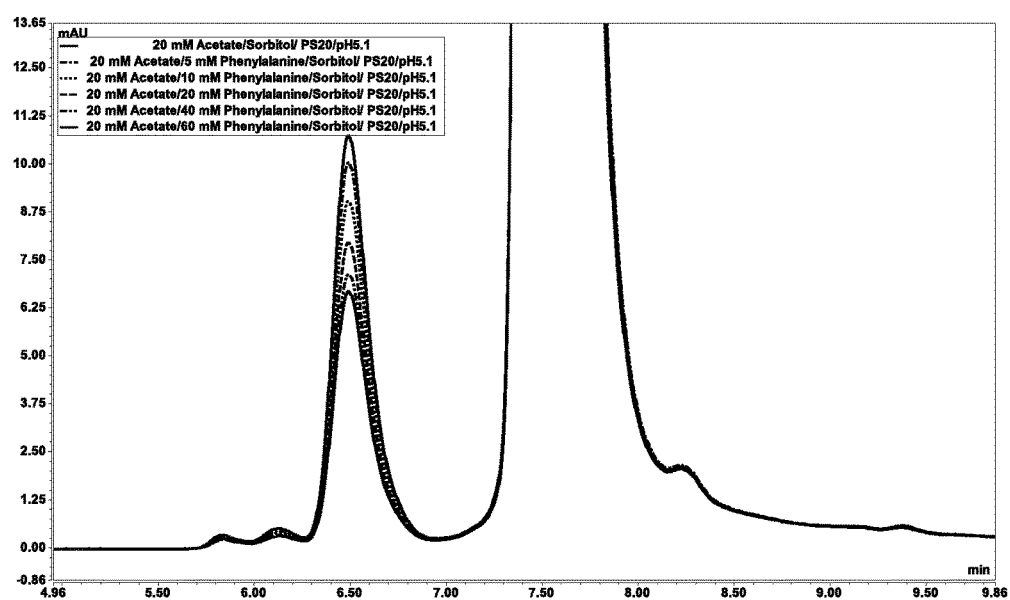
FIG. 12B show size exclusion chromatograms for formulations of Table 7C.

FIG. 11A and Table 7B show the percent HMWS monitored by SE-UHPLC as a function of formulation and time at 37° C. FIG. 11B and Table 7C show the percent HMWS monitored by SE-UHPLC as a function of formulation and time at 40° C. FIGS. 12A and 12B show size exclusion chromatograms as a function of formulation following storage at 37° C. and 40° C. for 1 month, respectively.

TABLE 7B

| | | Percentage HMWS | | |
|---|---|---|---|---|
| | Formulation | 0 | 2 weeks | 4 weeks |
| A | Acetate/Sorbitol/PS20/pH 5.1 | 0.9 | 1.5 | 2.0 |
| B | Acetate/75 mM Arginine/Sorbitol/ PS20/pH 5.1 | 0.7 | 1.1 | 1.5 |
| C | Acetate/38 mM Phenylalanine/Sorbitol/ PS20/pH 5.1 | 0.5 | 0.9 | 1.3 |
| D | Acetate/75 mM Phenylalanine/Sorbitol/ PS20/pH 5.1 | 0.5 | 0.8 | 1.2 |
| E | Acetate/38 mM Arginine/38 mM Phenylalanine/Sorbitol/PS20/pH 5.1 | 0.7 | 1.0 | 1.4 |

TABLE 7C

| | | Percentage HMWS | | |
|---|---|---|---|---|
| | Formulation | 0 | 2 weeks | 4 weeks |
| F | 20 mM Acetate/Sorbitol/PS20/pH 5.1 | 0.67 | 1.44 | 1.96 |
| G | 20 mM Acetate/5 mM Phenylalanine/ Sorbitol/PS20/pH 5.1 | 0.64 | 1.34 | 1.74 |
| H | 20 mM Acetate/10 mM Phenylalanine/ Sorbitol/PS20/pH 5.1 | 0.60 | 1.26 | 1.68 |
| I | 20 mM Acetate/20 mM Phenylalanine/ Sorbitol/PS20/pH 5.1 | 0.53 | 1.12 | 1.51 |
| J | 20 mM Acetate/40 mM Phenylalanine/ Sorbitol/PS20/pH 5.1 | 0.48 | 1.02 | 1.37 |
| K | 20 mM Acetate/60 mM Phenylalanine/ Sorbitol/PS20/pH 5.1 | 0.44 | 0.96 | 1.28 |

All phenylalanine formulations (Formulations C, D, E, G-K), contained lower levels of HMWS when compared to both the sorbitol and arginine hydrochloride/sorbitol formulations (Formulations A and B, respectively). The arginine hydrochloride and phenylalanine combination formulation had similar stability when compared to the arginine/sorbitol formulation (Formulation B). All formulations were superior to the sorbitol control formulation (Formulation A and F).

Example 8

This example demonstrates an evaluation of different amino acid aggregation inhibitors.

An evaluation of different amino acid aggregation inhibitors was conducted by preparing eight formulations with a hydrophobic, aromatic, or polar/charged amino acid to determine their effect on minimizing the amount (%) of HMWS in a high-concentration liquid denosumab formulation (120 mg/mL), and HMWS formation over time. The formulation included one of eight L-amino acids and a reduced amount of sorbitol, relative to a control formulation not containing any amino acid aggregation inhibitor and a higher amount of sorbitol for isotonicity (Formulation 26).

The tested amino acid aggregation inhibitors were grouped into one of three groups (Groups I-III) and contained the amount of the amino acid aggregation inhibitor, as follows:

I. Aromatic amino acids:
 (a) 38 mM Phenylalanine (Formulation 27);
 (b) 38 mM Tryptophan (Formulation 28);
II. Polar/Charged amino acids:
 (a) 75 mM Arginine HCl (Formulation 29);
 (b) 75 mM Lysine (Formulation 30);
 (c) 75 mM Histidine (Formulation 31);
III. Hydrophobic amino acids:
 (a) 38 mM Leucine (Formulation 32);
 (b) 38 mM Isoleucine (Formulation 33);
 (c) 38 mM Valine (Formulation 34).

To prepare Formulations 26-34, an aliquot of denosumab at 70 mg/mL in acetate, pH 5.2, was dialyzed against DF buffer described in TABLE 8A, with a total of 3 buffer changes to achieve a 1 million fold dilution of the previous formulation to ensure complete buffer exchange. The dialysis of the Histidine formulation F used a buffer with a starting pH of 4.0 and it was predicted that the pH would shift to the target pH of 5.1 upon protein concentration due to the Donnan effect and the co-centration of acetate. However, the pH did not shift to the target pH of 5.1 after the protein was concentrated to 120 mg/mL, but remained at pH 4.0. To bring the pH of the histidine formulation to pH 5.1, titration with dilute (0.1N) NaOH was required. The remaining formulations were over-concentrated using centrifuge-concentrator units, followed by a dilution to 124-128 mg/mL and the addition of polysorbate 20 to a final concentration of 0.01% (w/v).

TABLE 8A

| F# | Estimated Final Formulation | Dialysis Buffer Composition* |
|---|---|---|
| 26 (A) | 23 mM Acetate/4.6% (w/v) Sorbitol/PS20/pH 5.1 (control) | 10 mM Acetate, 5% (w/v) Sorbitol, 0.01% (w/v) Polysorbate 20, pH 4.0 |
| 27 (B) | 23 mM Acetate/35 mM Phenylalanine/4% (w/v) Sorbitol/PS20/pH 5.1 | 10 mM Acetate, 38 mM Phenylalanine, 4.4% (w/v) Sorbitol, pH 4.0 |
| 28 (C) | 23 mM Acetate/ Tryptophan/4% (w/v) Sorbitol/PS20/pH 5.1 | 10 mM Acetate, 38 mM Tryptophan, 4.4% (w/v) Sorbitol, pH 4.0 |
| 29 (D) | 10 mM Acetate/66 mM Arginine/2.2% (w/v) Sorbitol/PS20/pH 5.1 | 10 mM Acetate, 75 mM Arginine HCl, 2.4% (w/v) Sorbitol, pH 5.1 |
| 30 (E) | 10 mM Acetate/66 mM Lysine/ 2.2% (w/v) Sorbitol/PS20/pH 5.1 | 10 mM Acetate, 75 mM Lysine HCl, 2.4% (w/v) Sorbitol, pH 5.1 |
| 31 (F) | 10 mM Acetate/Histidine/ 2.2% (w/v) Sorbitol/PS20/pH 5.1 | 10 mM Acetate, 75 mM Histidine, 2.4% (w/v) Sorbitol, pH 4.0 |
| 32 (G) | 23 mM Acetate/Leucine/ 4% (w/v) Sorbitol/PS20/pH 5.1 | 10 mM Acetate, 38 mM Leucine, 4.4% (w/v) Sorbitol, pH 4.0 |
| 33 (H) | 23 mM Acetate/Isoleucine/4% (w/v) Sorbitol/PS20/pH 5.1 | 10 mM Acetate, 38 mM Isoleucine, 4.4% (w/v) Sorbitol, pH 4.0 |
| 34 (I) | 23 mM Acetate/Valine/ 4% (w/v) Sorbitol/PS20/pH 5.1 | 10 mM Acetate, 38 mM Valine, 4.4% (w/v) Sorbitol, pH 4.0 |

*Final formulations comprised 120 mg/mL denosumab and PS20 at a final concentration of 0.01% (w/v) and had the indicated pH. Sorbitol and phenylalanine concentrations are estimated at ~8.5% lower than the sorbitol concentration of the DF buffer. Arginine concentrations are estimated at ~12.5% lower than the Arginine concentration of the DF buffer. Letters in ( ) appearing after F# corresponds to FIGS. 13-18

The formulations were filled into containers at a fill volume of 1.0 mL. The formulations were stored at a temperature of 37° C. for up to 4 weeks. The aggregation inhibition, and stability against aggregation inhibition over time, as based on formation of HMWS and dimer species, was assessed using SE-UHPLC. The aggregation inhibition profiles of these formulations were compared at initial conditions and during and after the storage period.

Figure 13:
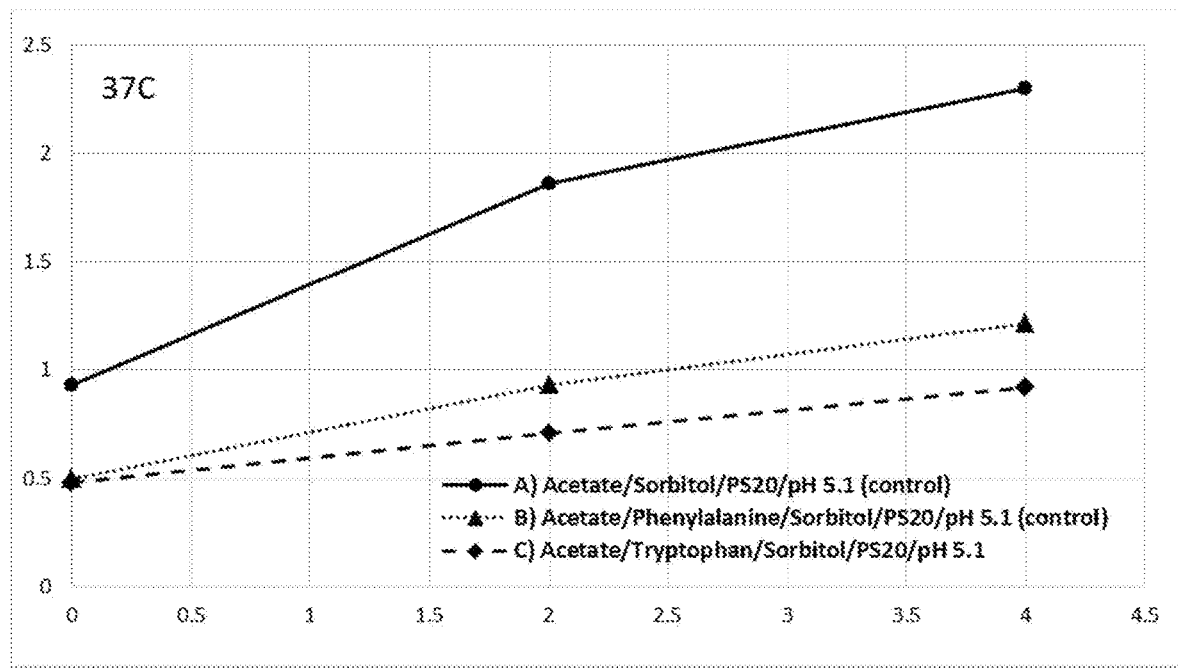
FIGS. 13, 14, and 15 are graphs of the percent HMWS monitored by SE-UHPLC as a function of storage time at 37° C. for each formulation having the corresponding Formulation letter shown in Table 8A.
Figure 14:
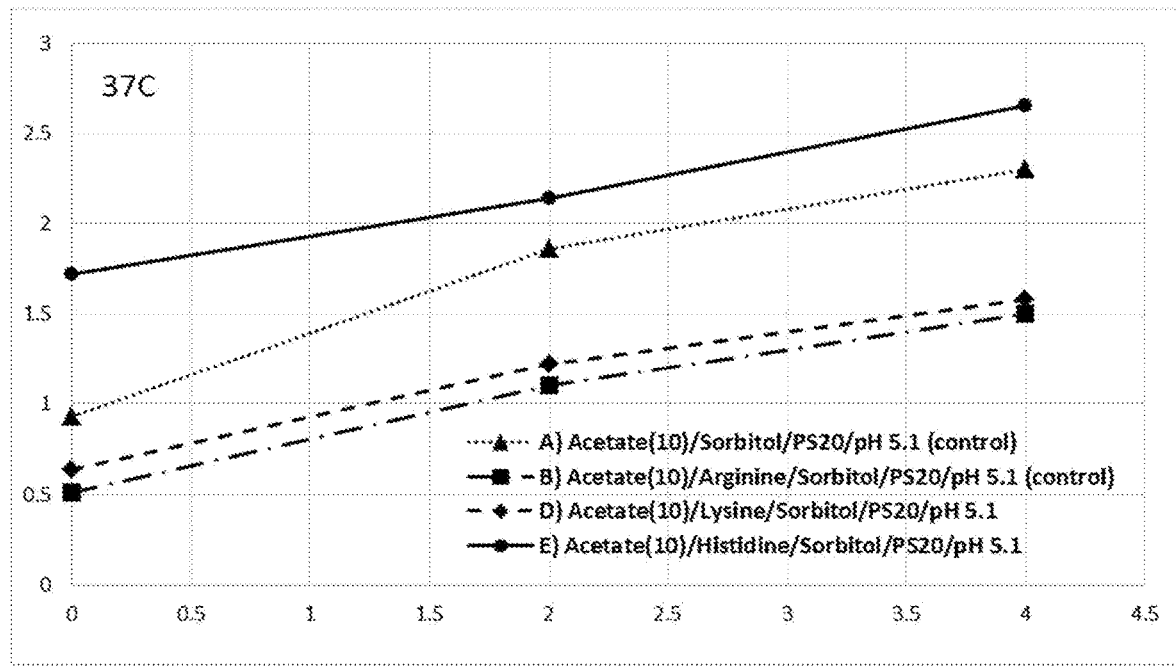
Figure 15:
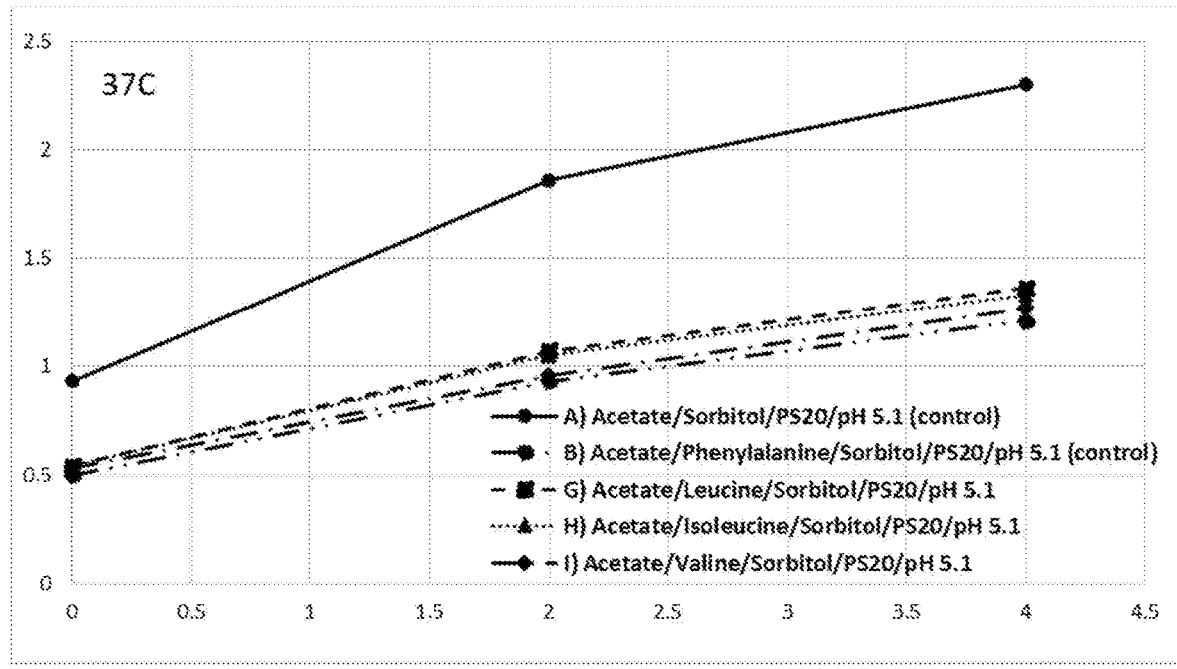
Figure 16:
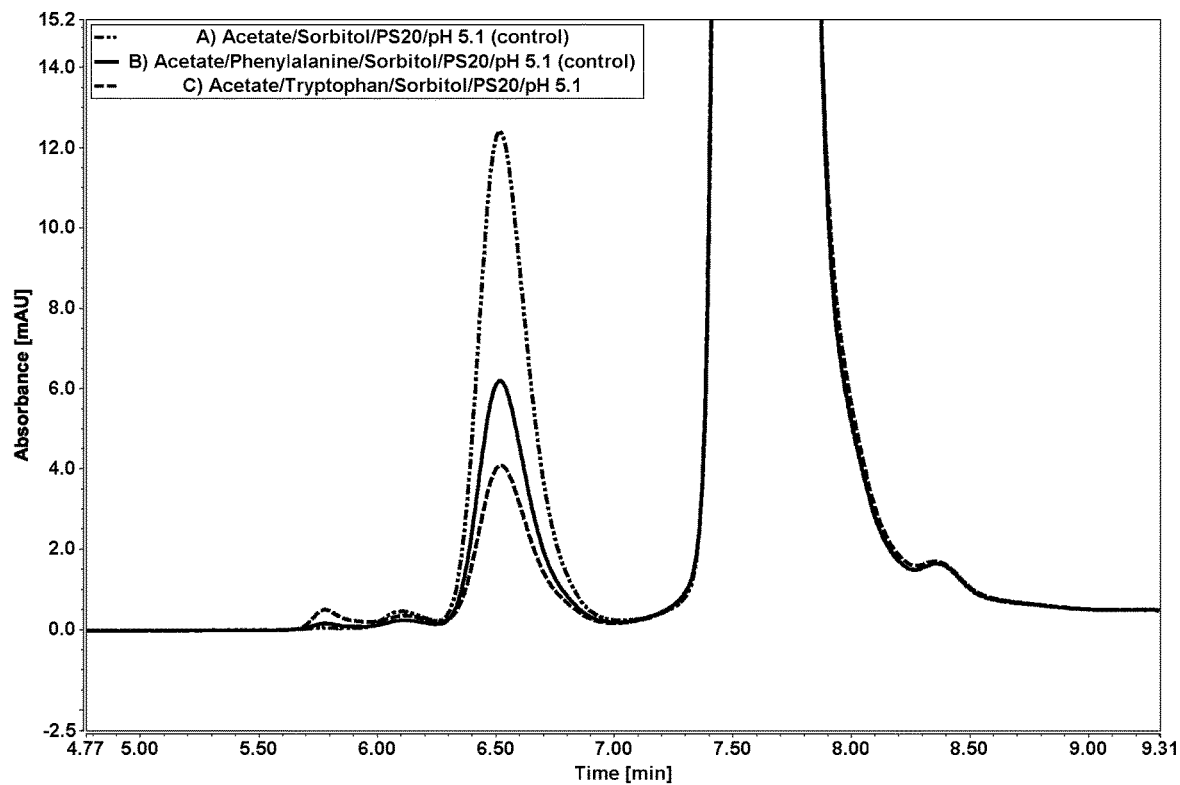
FIGS. 16, 17, and 18 are the chromatographic overlays of the formulations listed in Table 8A following storage at 37° C. for 1 month.
Figure 17:
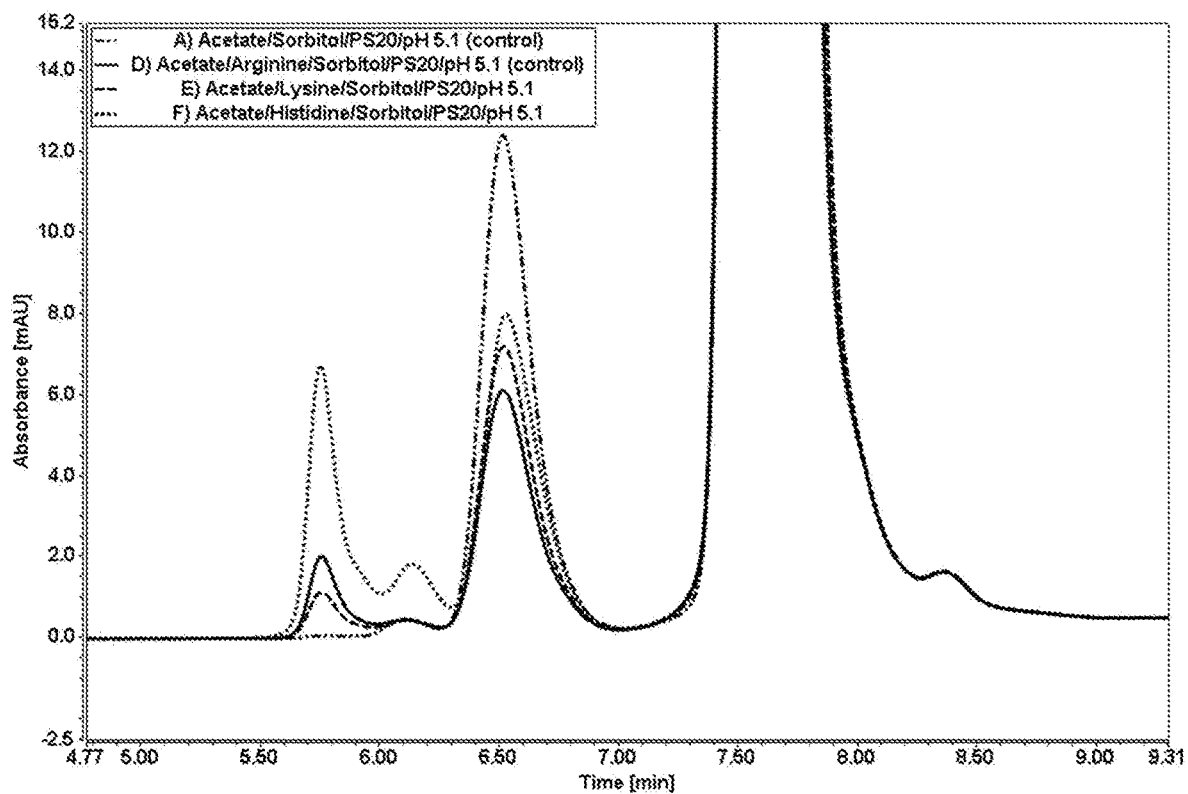
Figure 18:
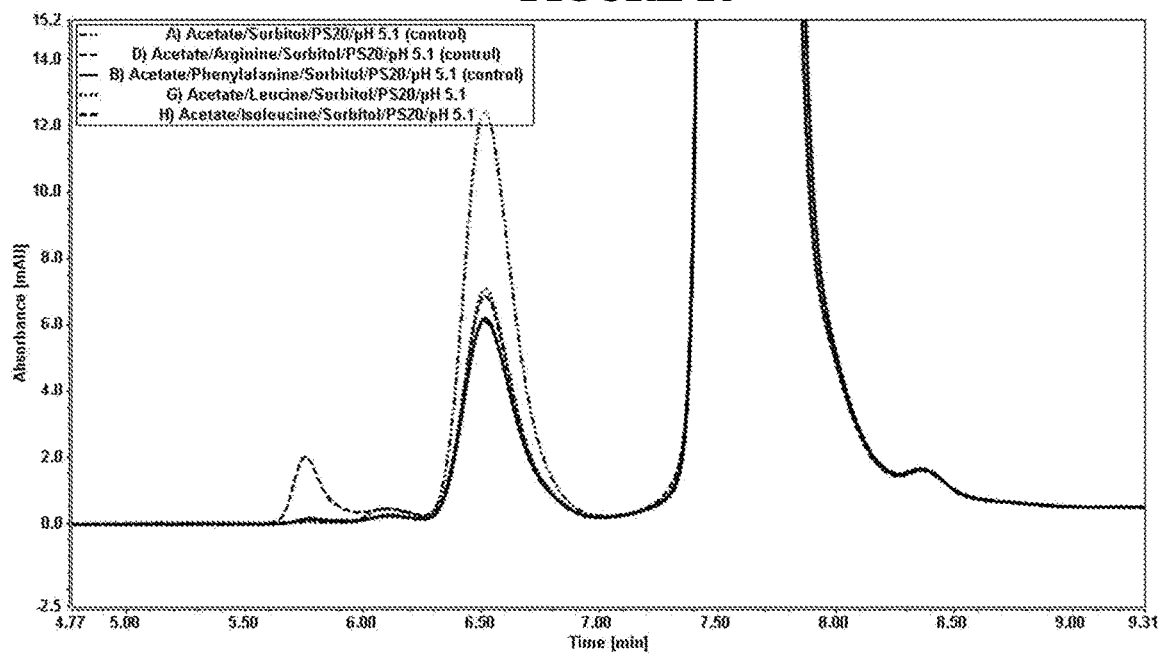
Figure 19:
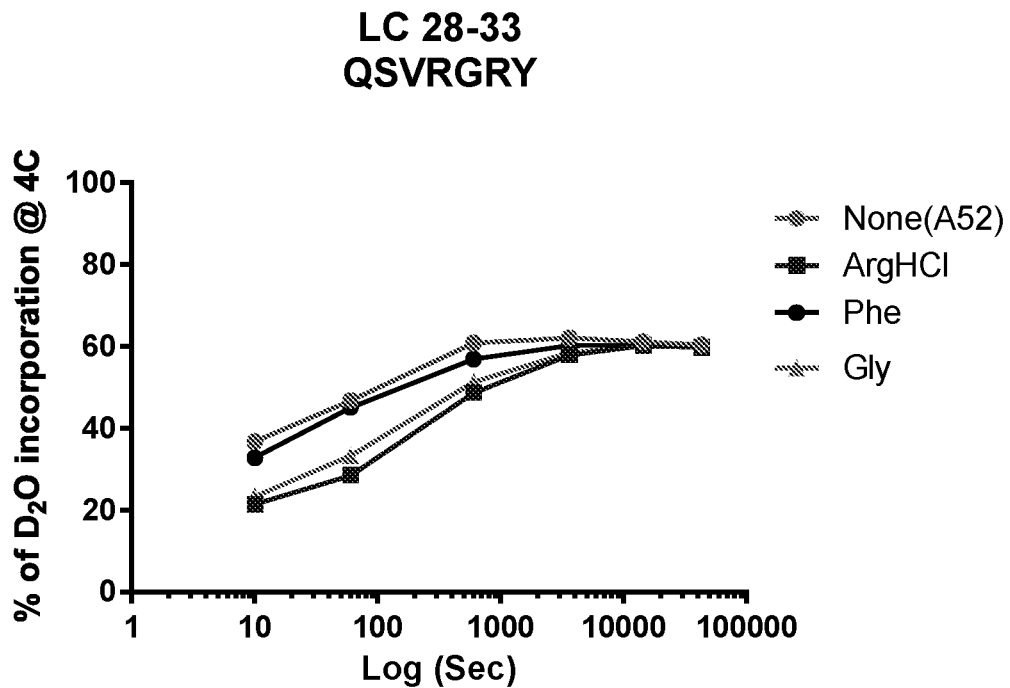
FIGS. 19-24 are graphs of % deuterium incorporation at 4° C. as a function of time (log(sec)) for the Light Chain amino acids 28-33 (FIG. 19), Light Chain amino acids 108-116 (FIG. 20), Light Chain amino acids 125-132 (FIG. 21), Heavy Chain amino acid 47-59 (FIG. 22), Heavy Chain amino acids 243-253 (FIG. 23), and Heavy Chain amino acids 392-399 (FIG. 24) for each of Formulations 35-38.
Figure 20:
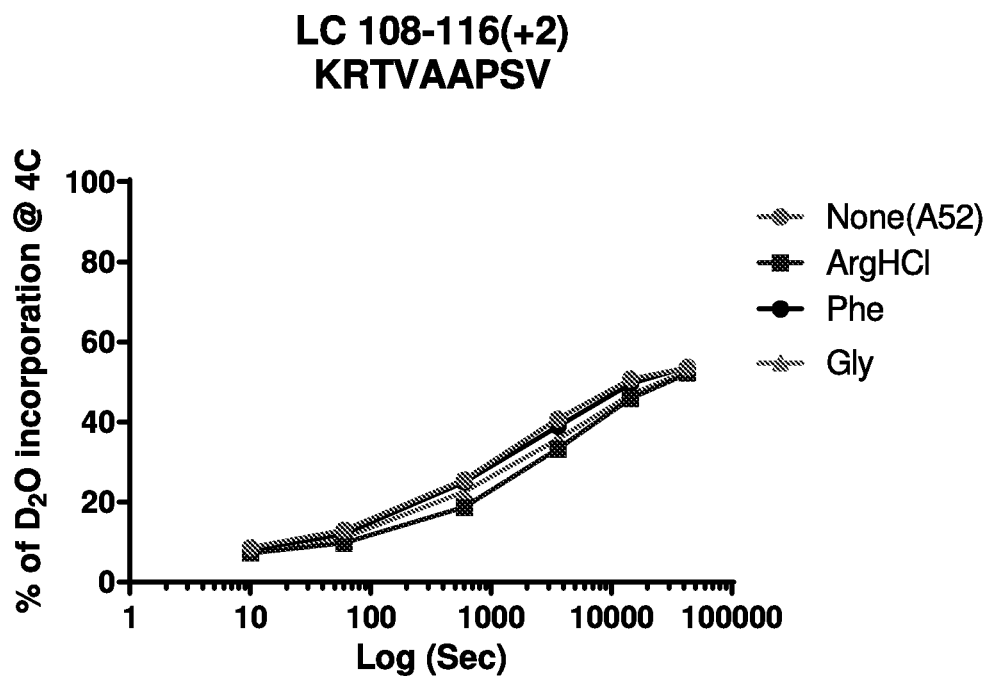
Figure 21:
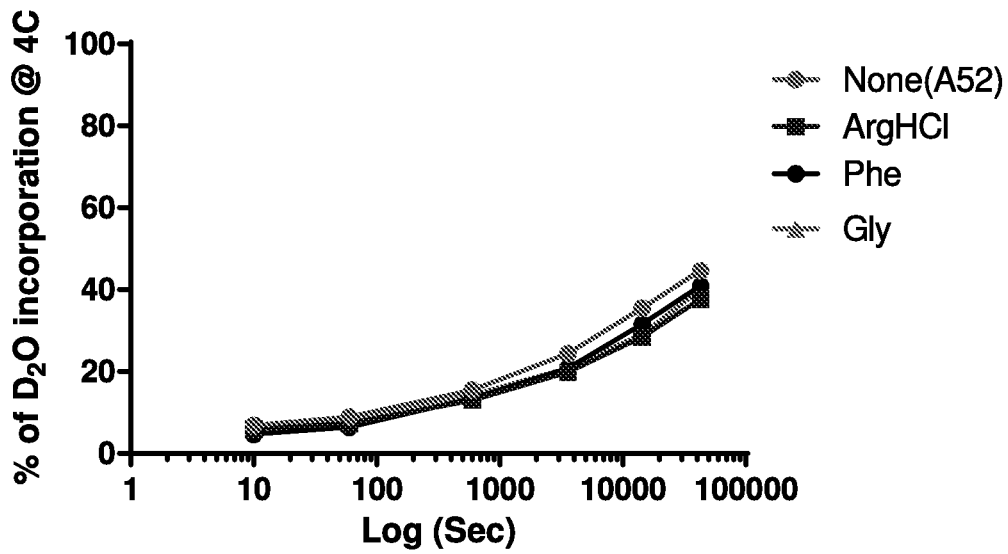
Figure 22:
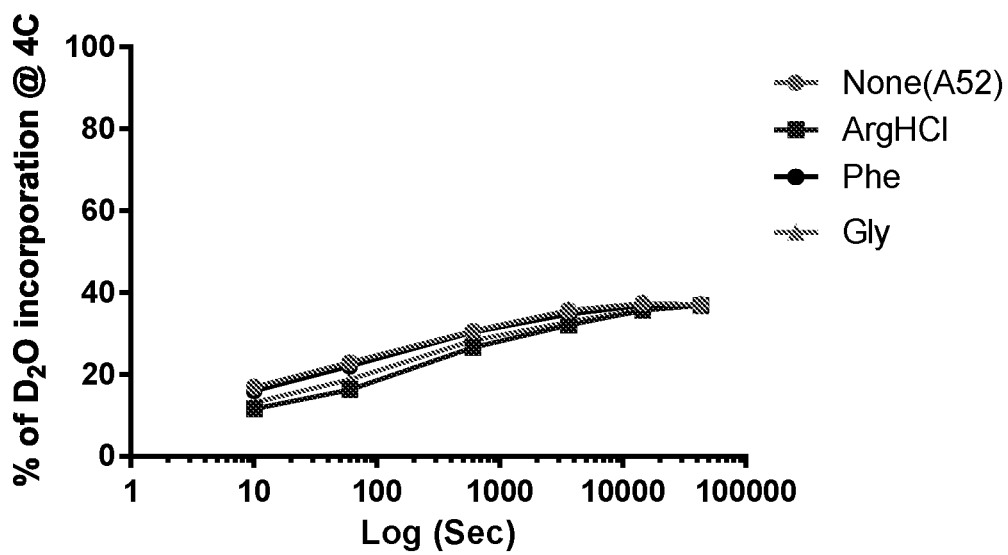
Figure 23:
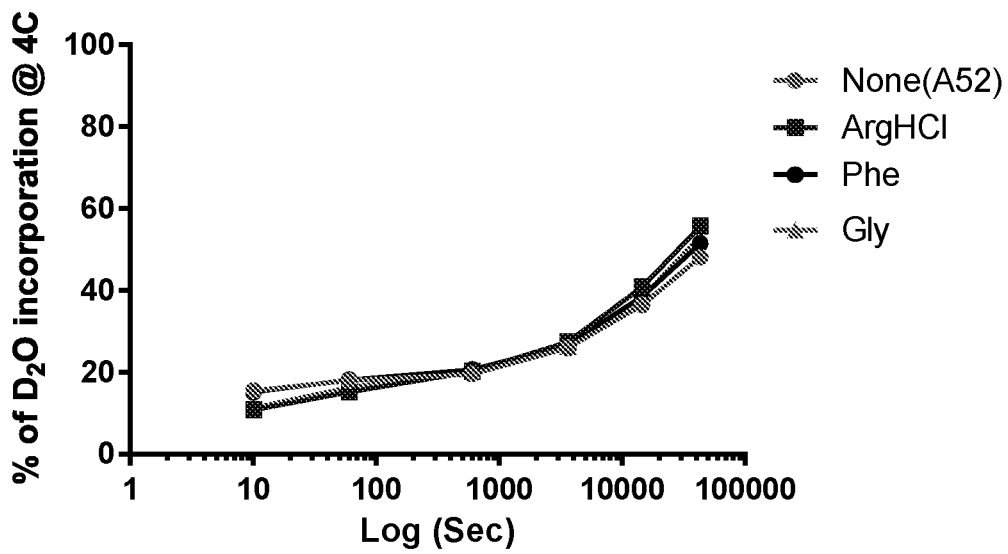
Figure 24:
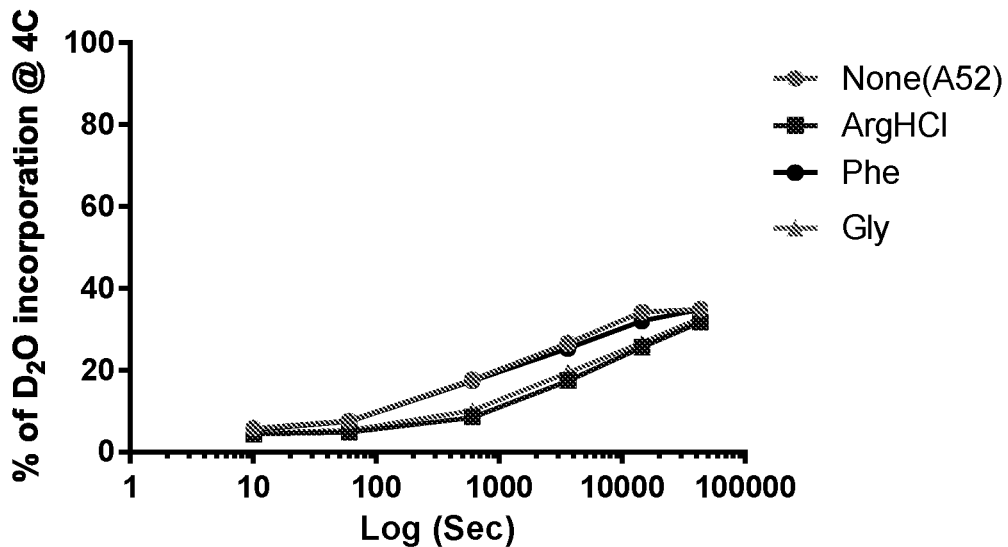
Figure 25:
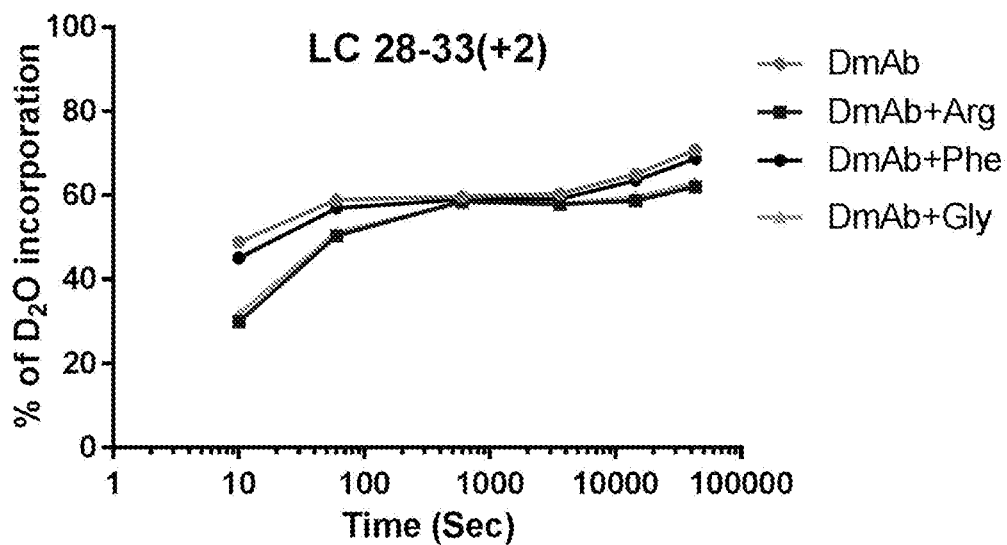
FIGS. 25-30 are graphs of % deuterium incorporation at 37° C. as a function of time (log(sec)) for the Light Chain amino acids 28-33 (FIG. 25), Light Chain amino acids 108-117 (FIG. 26), Light Chain amino acids 124-131 (FIG. 27), Heavy Chain amino acid 47-59 (FIG. 28), Heavy Chain amino acids 242-253 (FIG. 29), and Heavy Chain amino acids 392-399 (FIG. 30) for each of Formulations 35-38.
Figure 26:
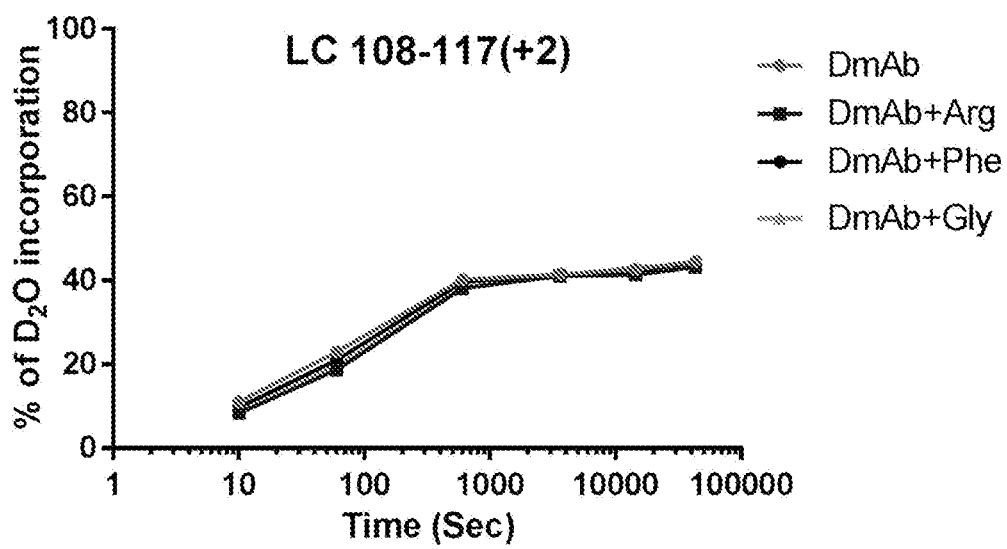
Figure 27:
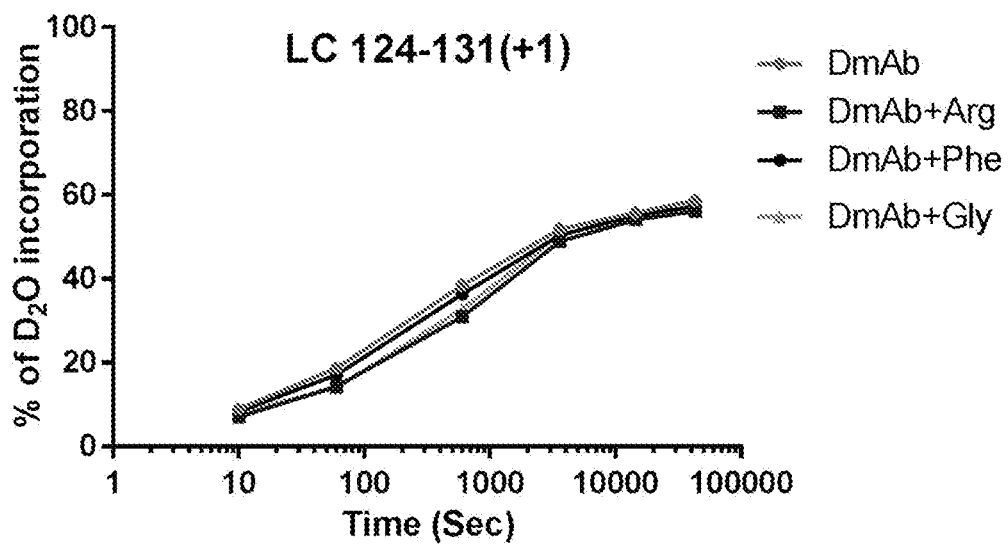
Figure 28:
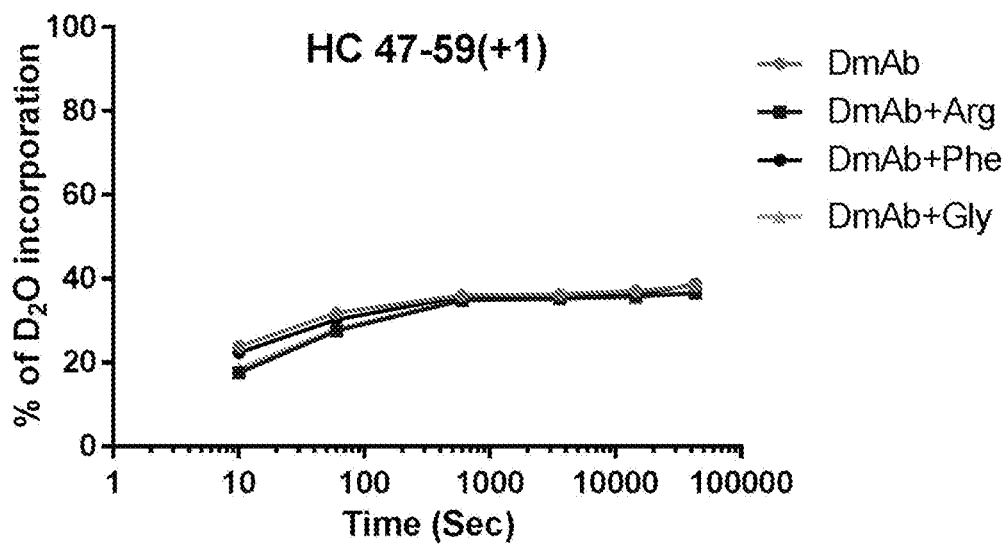
Figure 29:
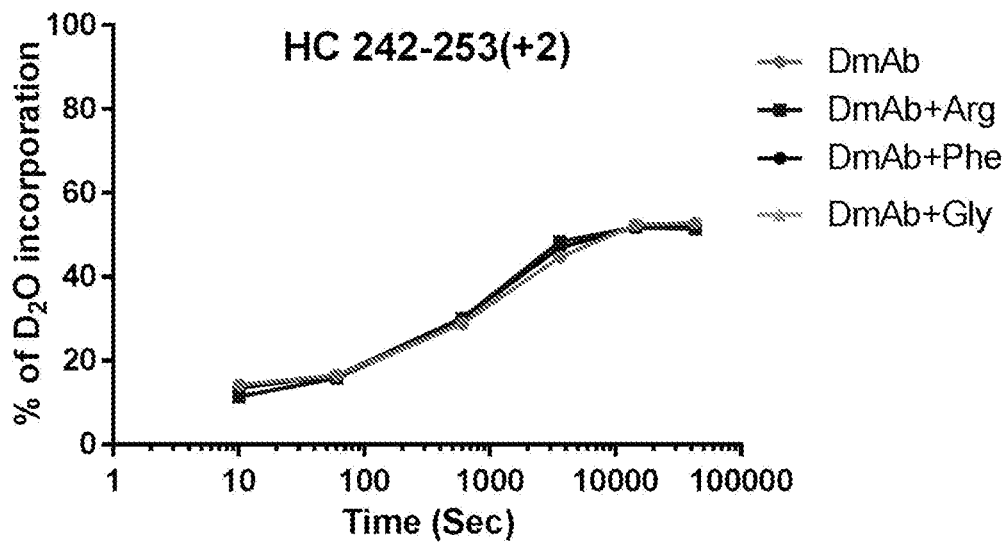
Figure 30:
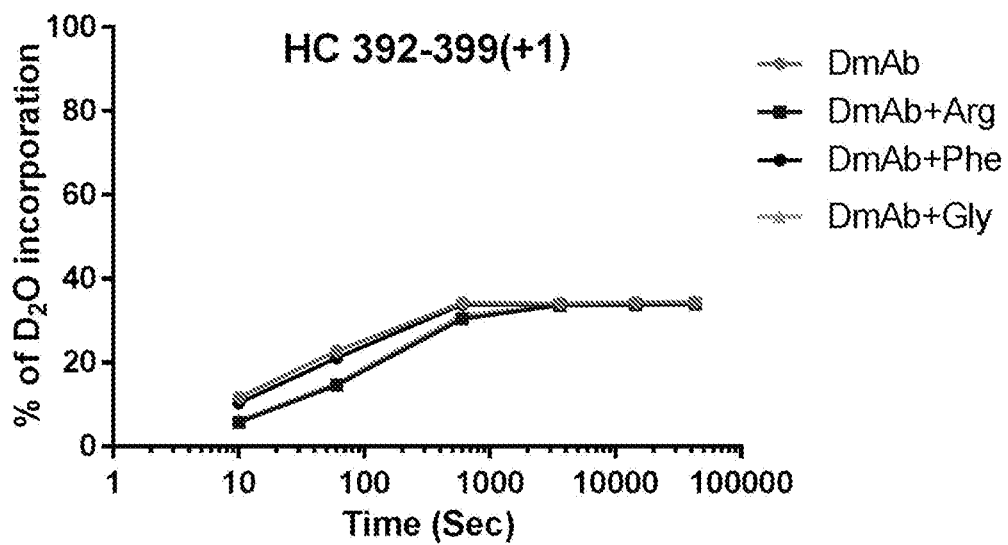

FIGS. 13-15 represent graphs of the percent HMWS monitored by SE-UHPLC as a function of storage time at 37° C. for each formulation and Table 8B provides the datapoints for the graphs. FIG. 16-18 show the chromatographic overlays of the formulations listed in Table 8A following storage at 37° C. for 1 month. FIGS. 13 and 16 relate to formulations comprising aromatic amino acids, FIGS. 14 and 17 relate to formulations comprising polar/charged amino acids, and FIGS. 15 and 18 relate to formulations comprising hydrophobic amino acids.

TABLE 8B

| | Percentage HMWS | | | |
|---|---|---|---|---|
| Formulation | 0 Weeks | 2 weeks | 4 weeks | Increase 0-4 weeks |
| AROMATIC AMINO ACIDS (FIG. 13) | | | | |
| 26 Acetate/Sorbitol/PS20/ pH 5.1 (control) | 0.9 | 1.9 | 2.3 | 1.4 |
| 27 Acetate/Phenylalanine/ Sorbitol/PS20/pH 5.1 (control) | 0.5 | 0.9 | 1.2 | 0.7 |
| 28 Acetate/Tryptophan/ Sorbitol/PS20/pH 5.1 | 0.5 | 0.7 | 0.9 | 0.4 |
| POLAR/CHARGED AMINO ACIDS (FIG. 14) | | | | |
| 26 Acetate/Sorbitol/PS20/ pH 5.1 (control) | 0.9 | 1.9 | 2.3 | 1.4 |
| 29 Acetate/Arginine/ Sorbitol/PS20/pH 5.1 (control) | 0.5 | 1.1 | 1.5 | 1.0 |

TABLE 8B-continued

| | Percentage HMWS | | | |
|---|---|---|---|---|
| Formulation | 0 Weeks | 2 weeks | 4 weeks | Increase 0-4 weeks |
| 30 Acetate/Lysine/ Sorbitol/PS20/pH 5.1 | 0.6 | 1.2 | 1.6 | 1.0 |
| 31 Acetate/Histidine/ Sorbitol/PS20/pH 5.1 | 1.7 | 2.1 | 2.7 | 1.0 |
| HYDROPHOBIC AMINO ACIDS (FIG. 15) | | | | |
| 26 Acetate/Sorbitol/PS20/ pH 5.1 (control) | 0.9 | 1.9 | 2.3 | 1.4 |
| 27 Acetate/Phenylalanine/ Sorbitol/PS20/pH 5.1 (control) | 0.5 | 0.9 | 1.2 | 0.7 |
| 32 Acetate/Leucine/ Sorbitol/PS20/pH 5.1 | 0.5 | 1.1 | 1.4 | 0.9 |
| 33 Acetate/Isoleucine/ Sorbitol/PS20/pH 5.1 | 0.5 | 1.1 | 1.3 | 0.8 |
| 34 Acetate/Valine/ Sorbitol/PS20/pH 5.1 | 0.5 | 1.0 | 1.3 | 0.8 |

F# is provided in the left column and corresponds to the F# of Table 8A.

As shown in FIGS. 13-15, all formulations containing an amino acid aggregation inhibitor (Formulations 27-34) demonstrated some improvement in stability, relative to the acetate/sorbitol formulation (Formulation 26). The formulations containing an aromatic amino acid (Formulations 27 and 28) showed the largest reduction in % HMWS. The formulation containing phenylalanine (Formulation 27) also demonstrated a large reduction in HMWS, and the formulation containing tryptophan showed the largest reduction, relative to the control (Formulation 26). Of the denosumab formulations containing a polar/charged amino acids (Formulations 29-31) generally showed greater amounts of larger order aggregates (FIG. 17) compared to other formulations having amino acid stabilizers (FIGS. 16 and 18), and this specific histidine formulation showed greater amounts of HWMS overall when compared to the acetate/sorbitol formulation (Formulation 26) (FIG. 14). The results from the histidine formulation could be biased from the dialysis process, longer duration spent at pH 4.0, and the titration of the formulation with dilute NaOH. The formulations containing a hydrophobic amino acid (Formulations 32-34) all demonstrated a consistent improvement in HMWS formation.

Example 9

This example demonstrates a possible mechanism of action of arginine and phenylalanine in stabilizing denosumab. Hydrogen deuterium exchange mass spectrometry (HDX-MS) is a sensitive and robust technology to characterize protein-protein/ligand/excipient interaction. The method detects changes in the backbone amide hydrogen bond due to interaction with the excipient.

Hydrogen deuterium exchange mass spectrometry (HDX-MS) was carried out with denosumab (at 3 mg/mL concentration) in 10 mM acetate buffer (pH 5.2) ("A52") in the presence of L-arginine (Formulation 35), L-phenylalanine (Formulation 36), or L-glycine (Formulation 37) and compared with a denosumab formulation lacking any amino acid aggregation inhibitors (Formulation 38). Experiments were carried out at 4° C. (with 75 mM concentration of L-arginine, L-phenylalanine, or L-glycine) and 37° C. (with 150 mM concentration of L-arginine, L-phenylalanine, or L-glycine). After analyzing more than 530 peptides, a small number of regions with significant conformational change were identified. A few representative peptides from these regions are captured in FIGS. 19-30.

FIGS. 19-24 are graphs of % deuterium incorporation at 4° C. as a function of time (log(sec)) for the Light Chain amino acids 28-33 (FIG. 19), Light Chain amino acids 108-116 (FIG. 20), Light Chain amino acids 125-132 (FIG. 21), Heavy Chain amino acid 47-59 (FIG. 22), Heavy Chain amino acids 243-253 (FIG. 23), and Heavy Chain amino acids 392-399 (FIG. 24) for each of Formulations 35-38.

FIGS. 25-30 are graphs of % deuterium incorporation at 37° C. as a function of time (log(sec)) for the Light Chain amino acids 28-33 (FIG. 25), Light Chain amino acids 108-117 (FIG. 26), Light Chain amino acids 124-131 (FIG. 27), Heavy Chain amino acid 47-59 (FIG. 28), Heavy Chain amino acids 242-253 (FIG. 29), and Heavy Chain amino acids 392-399 (FIG. 30) for each of Formulations 35-38.

These data support that Arg and Gly have a similar interaction effect on denosumab, though Arg had a slightly stronger HDX footprint (conformational changes) on denosumab: strong stabilization in Fab LC 28-33 region; subtle stabilization in Fab LC 108-132 and HC 47-59, Fc CH3 HC 392-399 regions; and subtle destabilization in Fc CH2 243-253 region. Without intending to be bound by any particular theory, it is conceived that the arginine hydrochloride effect is due to combined preferential exclusion from the denosumab surface and weak surface interactions, while glycine works by preferential exclusion.

However, phenylalanine showed no significant structural perturbation on denosumab. Without intending to be bound by any particular theory, it is conceived that the phenylalanine stabilizing effect could be through one or more of the following mechanisms: side chain interactions because there is no effect on the peptide backbone (no HDX footprint); and/or cation-pi interaction with arginine/lysine side chains without affecting the backbone hydrogen bond network.

Example 10

This example demonstrates a possible mechanism of action of phenylalanine stabilizing denosumab.

To study the specific effect of Phe on denosumab, a molecular dynamics simulation was performed. Specifically, the Fab domain of denosumab was solvated in a simulation box with excess Phe and two 10-ns simulations were conducted. Collectively, Phe residues bound to the Fab for over 90% of the time were selected for further analysis. Nine such cases were identified. In 5 of the 9 observations of long time residence, the Phe residue was bound to the interface of the VH/VL (variable heavy/variable light) and CH/CL (constant heavy/constant light) regions. In one example, the Phe side chain was believed to be interacting with the side chains of hydrophobic residues (e.g., V93, Y95, and W112 of the heavy chain and A44 and P45 of the light chain), at the interface of VH/VL. In another example, the side chain ring of Phe was believed to be interacting with the NH3+ and COO(−) groups of residues (e.g., T165 of the light chain and G171, V172, and T174 of the heavy chain) at the interface of CH1 and CL. Without intending to be bound by any particular theory, this observation led to the idea that the specific effect of Phe in mitigating the aggregation of denosumab is due to the interaction of the phenyl group with hydrophobic residues (e.g., R30, G31, R32, and Y33 of CDR1 of the light chain, A52 of CDR2 of the light chain, and M106 of CDR3 of the heavy chain) forming the interface of heavy constant 1 (Hc) and light constant (Lc) chains.

This interaction is hypothesized to replace a previously hydrophobic surface with a relatively more charged (consequently hydrophilic) surface from NH3(+) and COO(−) groups from the Phe excipient.

Example 11

A stability assessment of multiple constructs of anti-RANKL antibodies (of isotypes IgG1, IgG2, and IgG4) was conducted. As described above, both arginine HCl and phenylalanine minimize starting HMWS, and HWMS levels over time, when compared to the acetate/sorbitol control formulation of denosumab (which is an IgG2 immunoglobulin). This assessment was carried out to compare the potential of Arg-HCl and Phe to reduce HMWS in formulations containing different anti-RANKL antibody constructs. The IgG1 and IgG4 constructs tested in this study contained the same complementarity determining regions (CDR) when compared to denosumab, but contained different constant domain scaffolding. The different IgG2 construct tested in this study had different CDRs relative to denosumab, but contained the same constant domain scaffold.

Each tested antibody construct was purified and concentrated from 8 mg/mL to 70 mg/mL using centrifuge concentration. Each concentrated volume was split into three aliquots and then dialyzed against an acetate buffer formulated with sorbitol, sorbitol/phenylalanine and sorbitol/arginine hydrochloride to prepare the Formulations 39-47, as described in TABLE 9. The post-dialysis samples were over-concentrated to more than 120 mg/mL with centrifuge concentration. The antibody protein was diluted to 120 mg/mL with the respective buffer.

TABLE 9

| F# | Estimated Final Formulation | DF Buffer Composition |
|---|---|---|
| 39 | 23 mM Acetate/4.6% (w/v) Sorbitol/PS20/pH 5.1 -IgG1 | 10 mM Acetate, 5% (w/v) Sorbitol, pH 4.0 |
| 40 | 10 mM Acetate/66 mM Arginine/3.3% (w/v) Sorbitol/PS20/pH 5.1 -IgG1 | 10 mM Acetate, 3.6% (w/v) Sorbitol, 75 mM Arginine HCl, pH 5.1 |
| 41 | 23 mM Acetate/35 mM Phenylalanine/3% (w/v) Sorbitol/PS20/pH 5.1 -IgG1 | 10 mM Acetate, 3.3% (w/v) Sorbitol, 38 mM Phenylalanine, pH 4.0 |
| 42 | 23 mM Acetate/4.6% (w/v) Sorbitol/PS20/pH 5.1 -IgG2 | 10 mM Acetate, 5% (w/v) Sorbitol, pH 4.0 |
| 43 | 10 mM Acetate/66 mM Arginine/3.3% (w/v) Sorbitol/PS20/pH 5.1 -IgG2 | 10 mM Acetate, 3.6% (w/v) Sorbitol, 75 mM Arginine HCl, pH 5.1 |
| 44 | 23 mM Acetate/35 mM Phenylalanine/3% (w/v) Sorbitol/PS20/pH 5.1 -IgG2 | 10 mM Acetate, 3.3% (w/v) Sorbitol, 38 mM Phenylalanine, pH 4.0 |
| 45 | 23 mM Acetate/4.6% (w/v) Sorbitol/PS20/pH 5.1 -IgG4 | 10 mM Acetate, 5% (w/v) Sorbitol, pH 4.0 |
| 46 | 10 mM Acetate/66 mM Arginine/3.3% (w/v) Sorbitol/PS20/pH 5.1 -IgG4 | 10 mM Acetate, 3.6% (w/v) Sorbitol, 75 mM Arginine HCl, pH 5.1 |
| 47 | 23 mM Acetate/35 mM Phenylalanine/3% (w/v) Sorbitol/PS20/pH 5.1 -IgG4 | 10 mM Acetate, 3.3% (w/v) Sorbitol, 38 mM Phenylalanine, pH 4.0 |

*Final formulations comprised PS20 at a final concentration of 0.01% (w/v) and had the indicated pH. Sorbitol and phenylalanine concentrations are estimated at ~8.5% lower than the concentration of the DF buffer. Arginine concentrations are estimated at ~12.5% lower than the concentration of the DF buffer.

The formulations were filled into glass vial containers at a fill volume of 1.0 mL. The formulations were stored at a temperature of 37° C. for up to 1 month. The aggregation inhibition, and stability against aggregation inhibition over time, as based on formation of HMWS, was assessed using SE-UHPLC. The aggregation inhibition profiles of these formulations were compared at initial conditions and after the storage period. The stability of these formulations after storage was compared within the immunoglobulin class.

Figure 31:
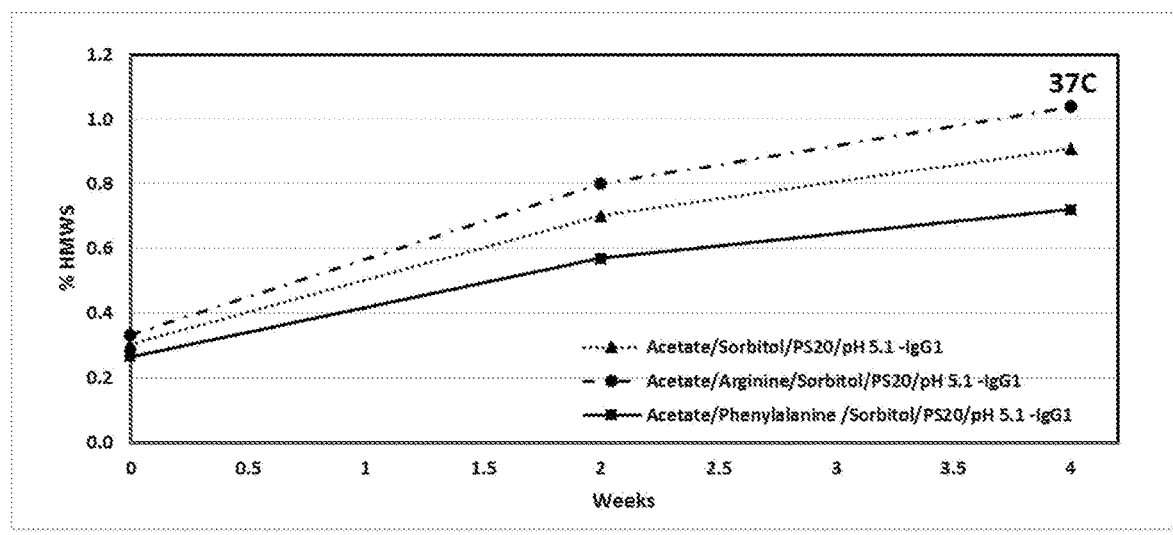
FIG. 31 is a graph of the percent HMWS monitored by SE-UHPLC as a function of formulation and time at 37° C. with the Formulation name indicated in Table 10.
Figure 32:
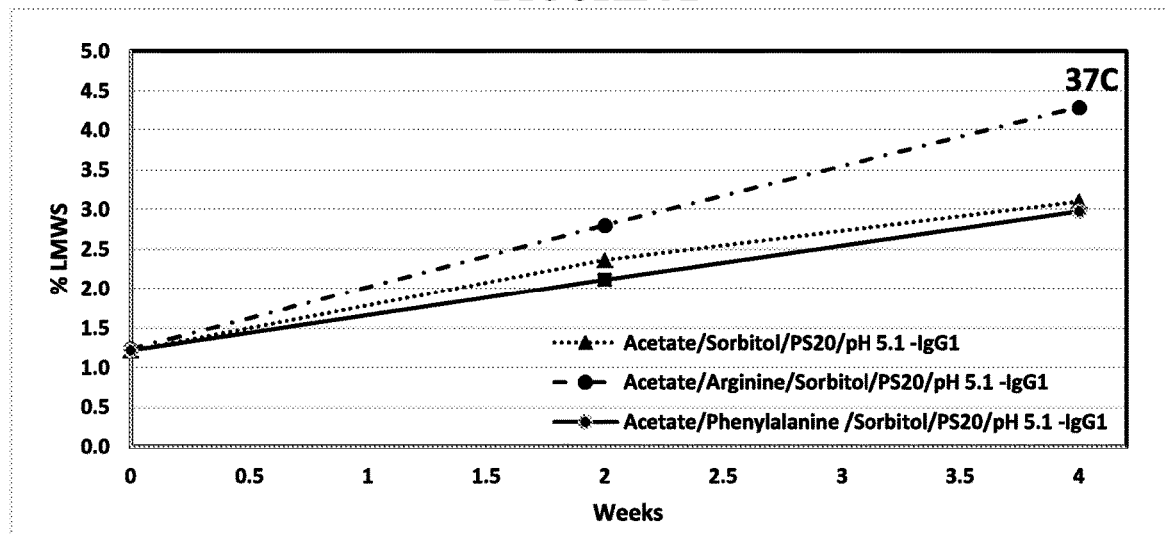
FIG. 32 is a graph of the percent LMWS as monitored by SE-UHPLC as a function of formulation and time at 37° C. with the Formulation name indicated in Table 11.
Figure 33:
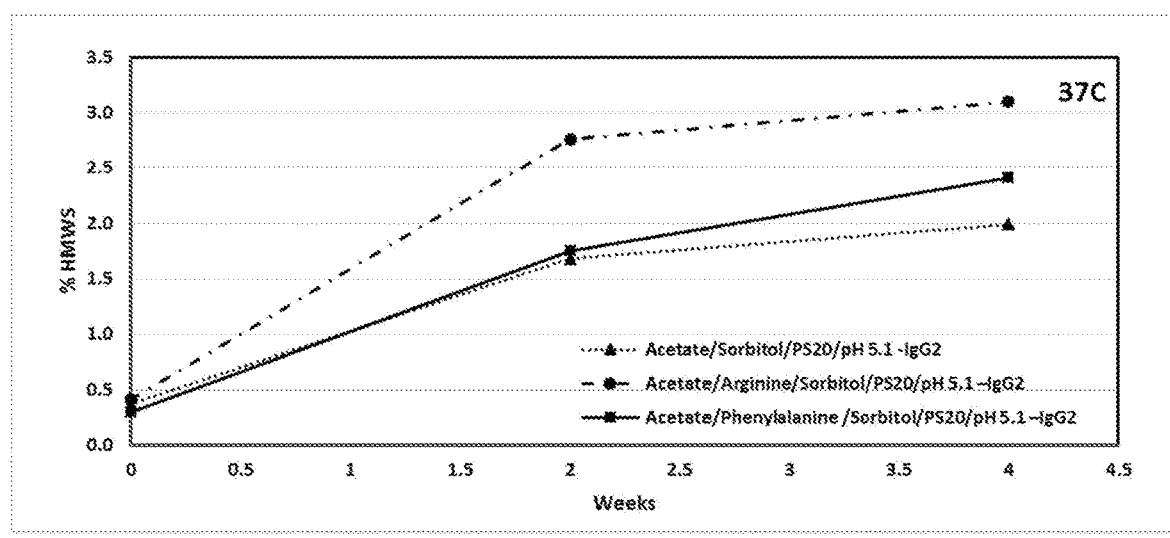
FIG. 33 is a graph of the percent HMWS monitored by SE-UHPLC as a function of formulation and time at 37° C. with the Formulation name indicated in Table 12.
Figure 34:
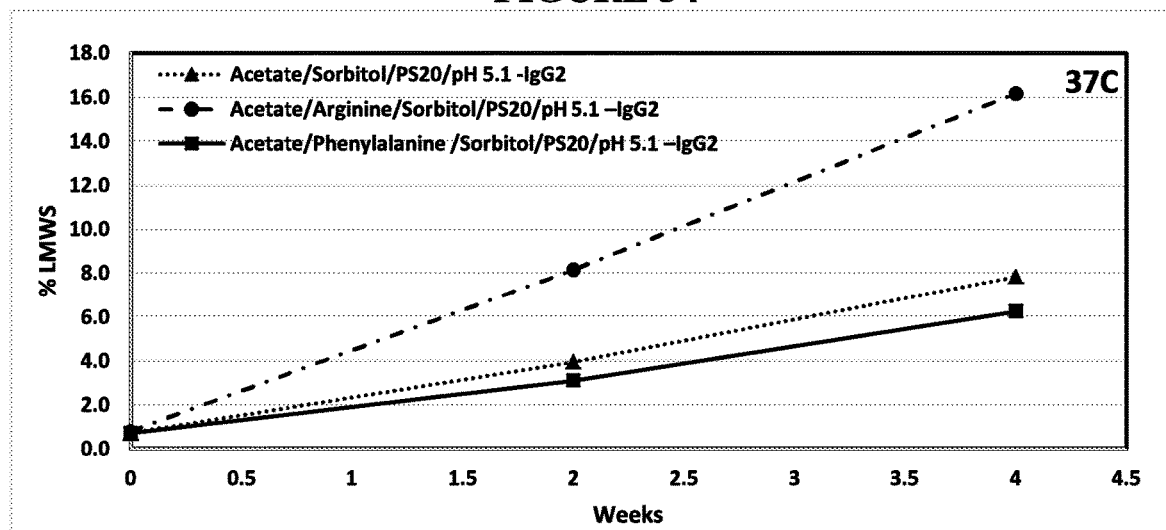
FIG. 34 is a graph of the percent LMWS as monitored by SE-UHPLC as a function of formulation and time at 37° C. with the Formulation name indicated in Table 13.
Figure 35:
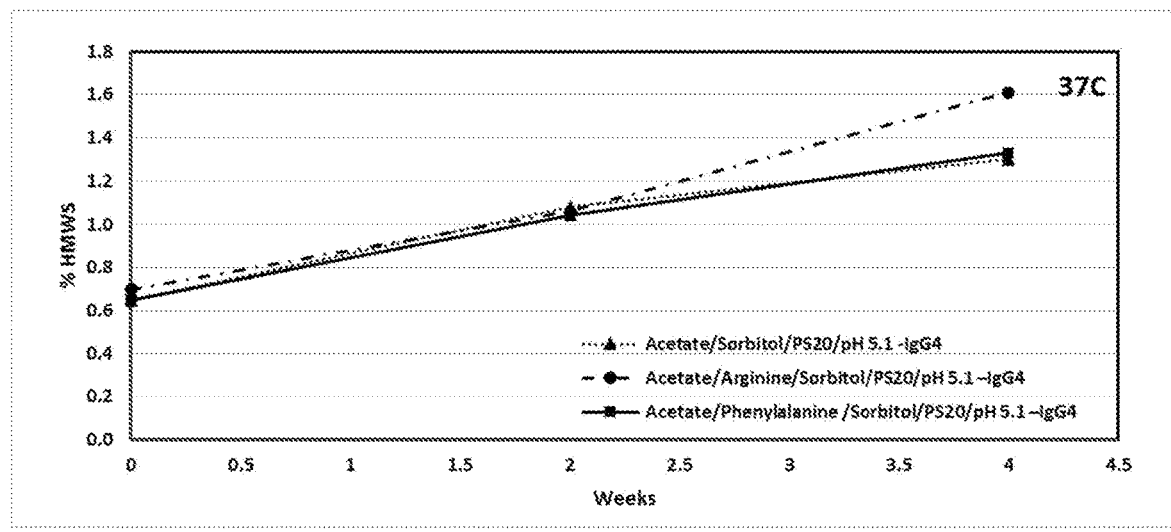
FIG. 35 is a graph of the percent HMWS monitored by SE-UHPLC as a function of formulation and time at 37° C. with the Formulation name indicated in Table 14.
Figure 36:
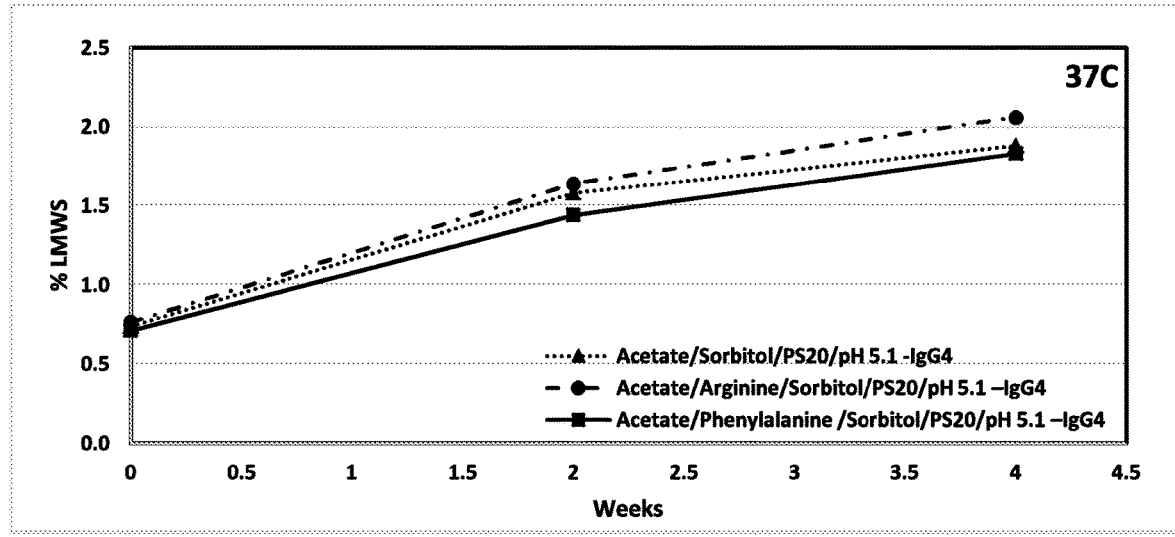
FIG. 36 is a graph of the percent LMWS as monitored by SE-UHPLC as a function of formulation and time at 37° C. with the Formulation name indicated in Table 15.
Figure 37:
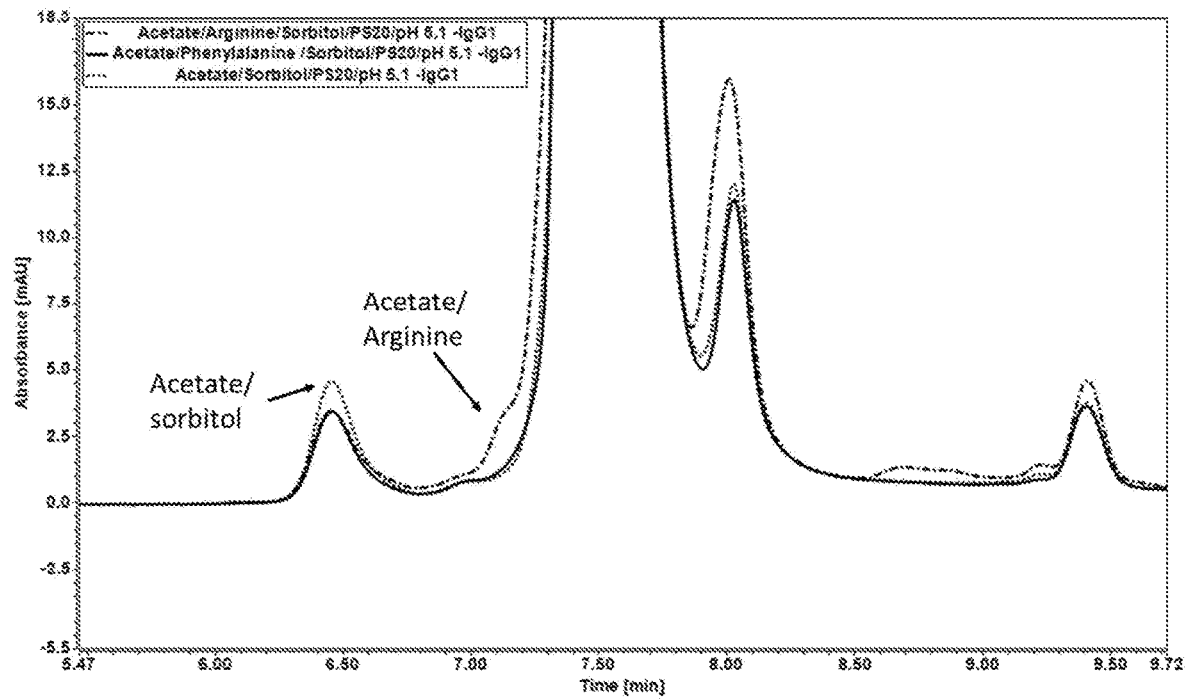
FIG. 37 are size exclusion chromatogram overlays for each formulation having the Formulation name indicated in Table 10.
Figure 38:
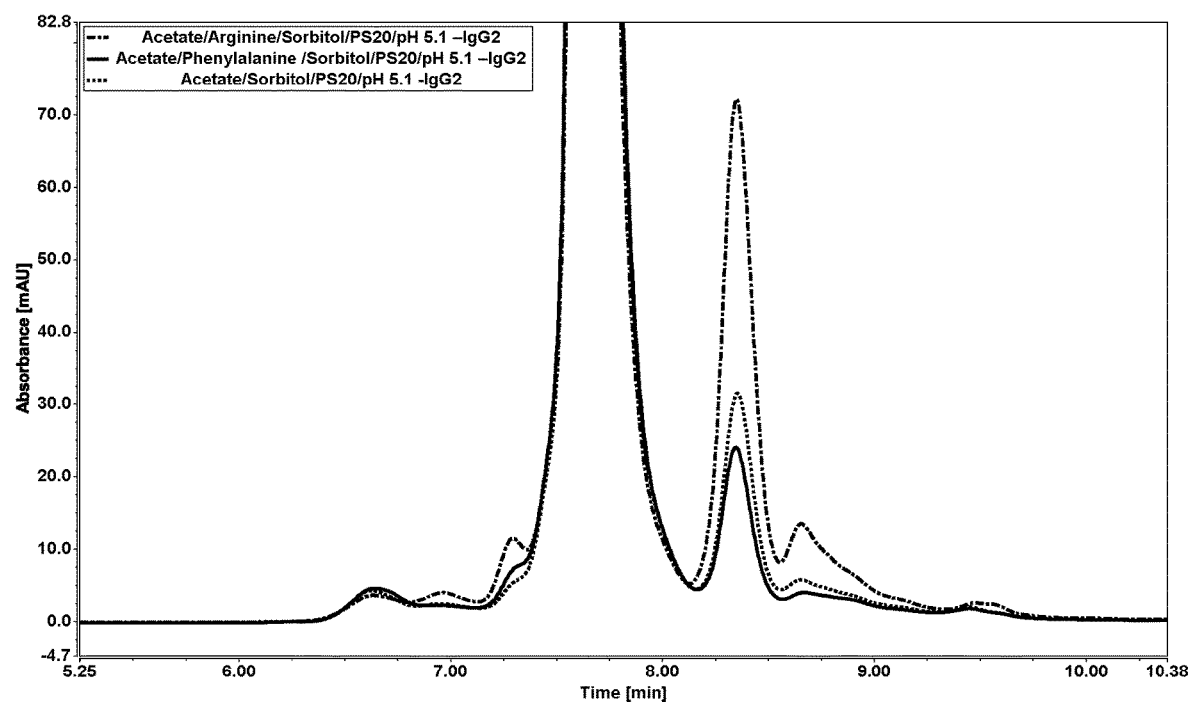
FIG. 38 are size exclusion chromatogram overlays for each formulation having the Formulation name indicated in Table 12.
Figure 39:
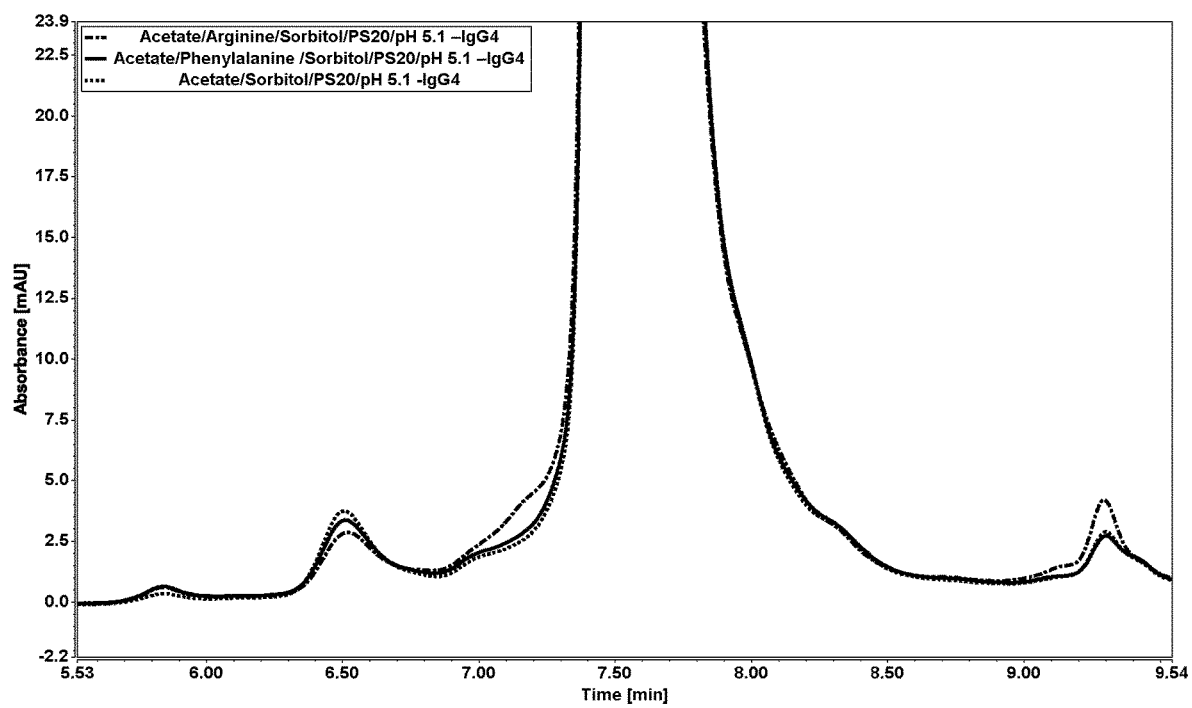
FIG. 39 are size exclusion chromatogram overlays for each formulation having the Formulation name indicated in Table 14.

FIGS. 31, 33, and 35 (and related TABLES 10, 12, and 14 below) show the percent HMWS monitored by SE-UHPLC as a function of formulation and time at 37° C. with immunoglobulins G (IgG1, IgG2, and IgG4, respectively). FIGS. 32, 34, and 36 (and related TABLES 11, 13, and 15 below) show the percent Low Molecular Weight Species (LMWS, e.g. protein fragmentation) as monitored by SE-UHPLC as a function of formulation and time at 37° C. with immunoglobulins G (IgG1, IgG2, and IgG4, respectively). FIGS. 37, 38, and 39 show size exclusion chromatogram overlays as a function of formulation following storage at 37 C for t=4w.

TABLE 10

% HMW, IgG1 (A, B, C) comparison at 37 C. for 4 weeks

| | | Percentage HMWS | | |
|---|---|---|---|---|
| | Formulation | 0 | 2 weeks | 4 weeks |
| 39 | Acetate/Sorbitol/PS20/pH 5.1 -IgG1 | 0.3 | 0.7 | 0.9 |
| 40 | Acetate/Arginine/Sorbitol/PS20/pH 5.1 -IgG1 | 0.3 | 0.8 | 1.0 |
| 41 | Acetate/Phenylalanine/Sorbitol/PS20/pH 5.1 -IgG1 | 0.3 | 0.6 | 0.7 |

TABLE 11

% LMWS, IgG1 (A, B, C) comparison at 37 C. for 4 weeks

| | | Percentage LMWS | | |
|---|---|---|---|---|
| | Formulation | 0 | 2 weeks | 4 weeks |
| 39 | Acetate/Sorbitol/PS20/pH 5.1 -IgG1 | 1.2 | 2.4 | 3.1 |
| 40 | Acetate/Arginine/Sorbitol/PS20/pH 5.1 -IgG1 | 1.2 | 2.8 | 4.3 |
| 41 | Acetate/Phenylalanine/Sorbitol/PS20/pH 5.1 -IgG1 | 1.2 | 2.1 | 3.0 |

TABLE 12

% HMW, IgG2 (D, E, F) comparison at 37 C. for 4 weeks

| | | Percentage HMWS | | |
|---|---|---|---|---|
| | Formulation | 0 | 2 weeks | 4 weeks |
| 42 | Acetate/Sorbitol/PS20/pH 5.1 -IgG2 | 0.4 | 1.7 | 2.0 |
| 43 | Acetate/Arginine/Sorbitol/PS20/pH 5.1 -IgG2 | 0.4 | 2.8 | 3.1 |
| 44 | Acetate/Phenylalanine/Sorbitol/PS20/pH 5.1 -IgG2 | 0.3 | 1.8 | 2.4 |

TABLE 13

% LMWS, IgG2 (D, E, F) comparison at 37 C. for 4 weeks

| | | Percentage LMWS | | |
|---|---|---|---|---|
| | Formulation | 0 | 2 weeks | 4 weeks |
| 42 | Acetate/Sorbitol/PS20/pH 5.1 -IgG2 | 0.7 | 4.0 | 7.8 |
| 43 | Acetate/Arginine/Sorbitol/PS20/pH 5.1 -IgG2 | 0.8 | 8.2 | 16.2 |

TABLE 13-continued

% LMWS, IgG2 (D, E, F) comparison at 37 C. for 4 weeks

| | | Percentage LMWS | |
|---|---|---|---|
| Formulation | 0 | 2 weeks | 4 weeks |
| 44 Acetate/Phenylalanine/Sorbitol/PS20/ pH 5.1 -IgG2 | 0.7 | 3.1 | 6.2 |

TABLE 14

% HMW, IgG4 (G, H, I) comparison at 37 C. for 4 weeks

| | | Percentage HMWS | |
|---|---|---|---|
| Formulation | 0 | 2 weeks | 4 weeks |
| 45 Acetate/Sorbitol/PS20/pH 5.1 -IgG4 | 0.6 | 1.1 | 1.3 |
| 46 Acetate/Arginine/Sorbitol/PS20/pH 5.1 -IgG4 | 0.7 | 1.1 | 1.6 |
| 47 Acetate/Phenylalanine/Sorbitol/PS20/ pH 5.1 -IgG4 | 0.6 | 1.0 | 1.3 |

TABLE 15

% LMWS, IgG4 (G, H, I) comparison at 37 C. for 4 weeks

| | | Percentage LMWS | |
|---|---|---|---|
| Formulation | 0 | 2 weeks | 4 weeks |
| 45 Acetate/Sorbitol/PS20/pH 5.1 -IgG4 | 0.7 | 1.6 | 1.9 |
| 46 Acetate/Arginine/Sorbitol/PS20/pH 5.1 -IgG4 | 0.8 | 1.6 | 2.1 |
| 47) Acetate/Phenylalanine/Sorbitol/PS20/ pH 5.1 -IgG4 | 0.7 | 1.4 | 1.8 |

As shown in FIGS. 31 and 32, the IgG1 molecule, which has a similar CDR region to previous denosumab samples, showed a reduction of approximately 0.2% in HMWS with the addition of phenylalanine when compared with the acetate/sorbitol control formulation. The IgG2 samples that have a different CDR and are depicted in FIGS. 33 and 34 showed an increase in HMWS in the acetate/phenylalanine/sorbitol formulation when compared to the control acetate/sorbitol formulation. The acetate/sorbitol and acetate/phenylalanine/sorbitol formulations had similar stability for the IgG4 sample type with the acetate/sorbitol/arginine having greater HMWS formation as shown in FIGS. 35 and 36. In all cases with the IgG1, IgG2, and IgG4 sample types, the acetate/sorbitol/arginine containing formulation showed increased HMWS degradation when compared to the acetate/sorbitol (control) and acetate/phenylalanine/sorbitol formulations.

Due to the large increase in protein fragmentation in the acetate/arginine/sorbitol formulation as depicted in FIGS. 37 and 38, the relationship between fragmentation and antibody isoform were shown in FIGS. 32, 34, and 36. It has been shown in literature that monoclonal antibody fragmentation-mediated aggregation can result for antibodies stored at 37° C. [Perico N. et al., J. Pharm. Sci. (2009) 98, pgs. 3031-3042]. This mechanism is possible in this evaluation as the fragmentation is greatest in the acetate/arginine/sorbitol formulations. The fragmentation is minimized in the acetate/phenylalanine/sorbitol formulation potentially leading to less HMWS species. The IgG4 sample type does not have accelerated fragmentation or aggregation.

From the data collected in this study as well and previous data molecular modeling data collected with denosumab, a strong correlation between the amino acid sequence of the CDRs and the relative effect of reducing HMWS with phenylalanine can be established. A reduction in HMW species was observed in denosumab (IgG2) and the IgG1 variant that had identical CDR amino acids, but no reduction in HMWS was observed in the IgG2 variant with different CDR domains. It would appear that amino acid sequences contained within the CDR domains are susceptible to interacting with phenylalanine and subsequent aggregation inhibition. The IgG4 molecule also had identical CDR regions when compared to denosumab, but minimal change in aggregation was detected over the course of the study. The IgG4 molecule differs from the IgG1 and IgG2 versions by primarily its hinge amino acid length and its functionally active structure. As IgG1 and IgG2 antibody isoforms have an extended structure that is typically described as a "Y" shape, an IgG4 Fab CH1 domain interacts with the CH2 domain forming a more compact structure [Aalberse R. C. et al., Immunology (2002), 105, pgs. 9-19]. This compact structure could inhibit fragmentation and aggregation reactions typically seen with IgG1 and IgG2 modalities.

Example 12

A study is conducted to monitor the stability of denosumab formulated as described below and in connection with Table 16 (Formulations 51-55). The diafiltration buffers differ in acetate concentration and starting pH to produce final formulations with Ph 5.1 at 120 mg/Ml denosumab concentration. Additionally, the sorbitol level is adjusted to maintain isotonicity of the final product (~300 mOsm/Kg). Denosumab at 70 mg/mL is diafiltered against each buffer for more than 7 diavolumes, then ultrafiltered to about 180 gm/mL and diluted with the diafiltration buffer and polysorbate to 120 mg/mL denosumab concentration and 0.01% polysorbate 20. Stability is assessed using SE-UHPLC after storage at 37° C. and shows that denosumab stability in these formulations is highly similar. Initial HMW species decrease slightly as initial acetate concentrations increase. In contrast, aggregation rates slightly improve in formulations with lower levels of acetate.

TABLE 16

| F# | DF Buffer | Estimated Final Formulation* | Osmolality (mOsm/kG) |
|---|---|---|---|
| 51 | 5 mM Acetate, 40 mM Phenylalanine, 4.4% Sorbitol, pH 4.0 | 16 mM Acetate, 37 mM Phenylalanine, 4.1% Sorbitol | 304 |
| 52 | 10 mM Acetate, 40 mM Phenylalanine, 4.2% Sorbitol, pH 4.4 | 23 mM Acetate, 37 mM Phenylalanine, 3.9% Sorbitol | 300 |
| 53 | 20 mM Acetate, 40 mM Phenylalanine, 4.0% Sorbitol, pH 4.7 | 32 mM Acetate, 37 mM Phenylalanine, 3.7% Sorbitol | 304 |
| 54 | 20 mM Acetate, 40 mM Phenylalanine, 4.2% Sorbitol, pH 4.7 | 32 mM Acetate, 37 mM Phenylalanine, 3.9% Sorbitol | 315 |
| 55 | 30 mM Acetate, 40 mM Phenylalanine, 3.7% Sorbitol, pH 4.8 | 41 mM Acetate, 37 mM Phenylalanine, 3.4% Sorbitol | 303 |

*Final formulations comprised 120 mg/mL denosumab and PS20 at a final concentration of 0.01% (w/v) and a pH 5.1.

Example 13

The following example reports the results of studies on the effect of arginine on the chemical denaturation stability of denosumab at three different pH values: 4.5, 4.8 and 5 (or 5.2).

All chemical denaturation experiments were carried out using Unchained Labs instrument—HUNK with fluorescence detector. The excitation wavelength was 280 nm and the emission scans were recorded between 300 and 500 nm. For each denaturation experiment, protein, buffer, and denaturant (guanidinium HCl) were dispensed into 36 wells with a linear increase in denaturant concentration, resulting in a 36 point curve for each condition. The curve fitting software provided by the instrument manufacturer (Unchained Labs) was used for fitting the data points. A two-state model was used since there was evidence of only a single transition (native ↔ denatured). The experiments were carried out using 0-6 M urea in 10 mM acetate 5.0% w/v sorbitol and titrated to the required pH of 4.5, 4.8 or 5 (5.2). The concentration of the denosumab protein was 7 mg/mL in all the experiments.

Figure 40A:
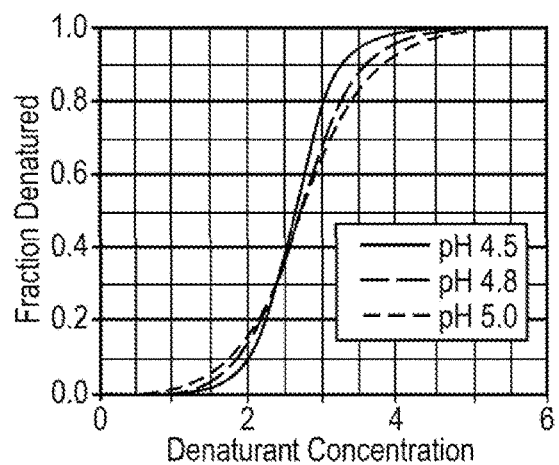
FIGS. 40A and 40B are graphs containing the isothermal chemical denaturation curves of denosumab in the absence of arginine, at pH 4.5, 4.8 and 5.0.
Figure 40B:
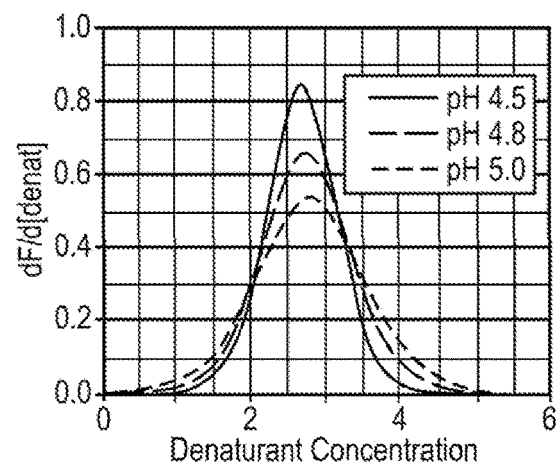

FIG. 40 shows the isothermal chemical denaturation curves of denosumab in the absence of arginine, at pH 4.5, 4.8 and 5.0. In the absence of arginine, the $C_{1/2}$ of chemical denaturant required for 50% unfolding is similar in the three pH conditions tested.

Figure 41A:
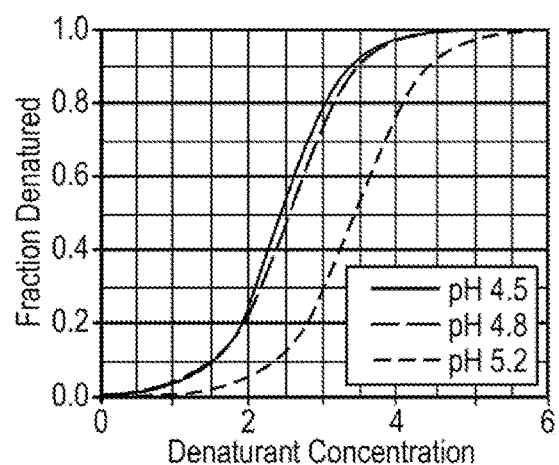
FIGS. 41A and 41B are graphs containing the isothermal chemical denaturation curves of denosumab in the presence of 75 mM arginine HCl at pH 4.5, 4.8. and 5.2.
Figure 41B:
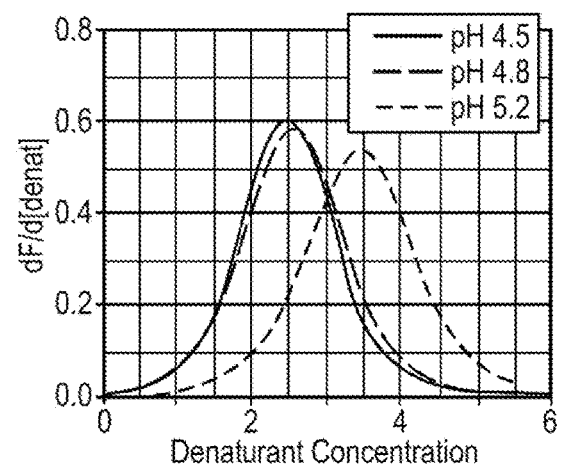

FIG. 41 shows the isothermal chemical denaturation curves of denosumab in the presence of 75 mM arginine HCl at pH 4.5, 4.8. and 5.2. There was a marked increase in the chemical denaturation stability at pH 5.2 when compared to pH 4.8 and 4.5. The $C_{1/2}$ increases by 1M of the denaturant guanidinium HCl at pH 5.2 vs lower pH. Thus, the protective nature of arginine is surprising and highly dependent on the pH.

Example 14

The following example provides the results of studies on the effect of arginine and phenylalanine on the stability over time of high concentration denosumab formulations in syringes.

In previous studies, arginine hydrochloride and phenylalanine were identified to reduce the initial starting level and rate of HMWS formation of denosumab. In this study, formulations containing arginine hydrochloride, phenylalanine, and a combination of arginine hydrochloride and phenylalanine were evaluated for stabilizing effects on solutions containing denosumab at 120 mg/mL and stored in syringes for up to three months and at two different temperatures.

The formulations tested are described in TABLE 17 below. To prepare formulations 56-59, denosumab at 70 mg/mL in acetate, pH 5.2 was diafiltered against the diafiltration (DF) buffers described below, for 8 diavolumes to ensure complete buffer exchange. The material was then ultrafiltered to more than 180 mg/mL, followed by a dilution to 120 mg/mL and the addition of polysorbate 20 to a final concentration of 0.01%. Formulation 56 was considered the control formulation. Acetate, arginine HCl and phenylalanine values listed are for the DF buffer and the estimated levels in the final composition at 120 mg/mL denosumab are provided, taking into consideration excipient exclusion and acetate co-concentration when no other counterion is present. Viscosity at 5° C. and 25° C. were measured using a Paar modular compact rheometer at shear rates up to 1000 s$^{-1}$ (inverse seconds). The formulations were filled into glass prefilled syringes (PFS) at a fill volume of 1.0 mL. Parallel sets of syringes were stored at a temperatures of 25° C. for 3 months and 37° C. for 2 months, respectively. The stability as based on formation of HMWS as assessed using SE-UHPLC.

TABLE 17

| | Abbreviated Name of Formulation | DF Buffer Composition* | Estimated final formulation* | Conductivity (µS/cm) | Viscosity at 5 C. | Viscosity at 25 C. |
|---|---|---|---|---|---|---|
| 56 | Acetate/Sorbitol/PS20/pH 5.0 | 20 mM Acetate, 5% (w/v) Sorbitol, pH 4.7 | 32 mM Acetate, 4.4 % Sorbitol | 600 | 5.2 | 3.1 |
| 57 | Acetate/Arginine HCl/Sorbitol/PS20/pH 5.1 | 10 mM Acetate, 75 mM L-Arginine HCl, 2.4% (w/v) Sorbitol, pH 5.1 | 10 mM Acetate, 66 mM Arginine HCl, 2.2% sorbitol | 5250 | 4.8 | 2.7 |
| 58 | Acetate/Arginine HCl/Phenylalanine/Sorbitol/PS20/pH 5.1 | 10 mM Acetate, 38 mM Arginine HCl, 38 mM Phenylalanine, 3.0% (w/v) Sorbitol, pH 5.1 | 10 mM Acetate, 33 mM Arginine HCl, 35 mM Phenylalanine 2.8% sorbitol | 3070 | 4.8 | 2.8 |
| 59 | Acetate/Phenylalanine/Sorbitol/PS20/pH 5.1 | 10 mM Acetate, 38 mM Phenylalanine, 4.4% (w/v) Sorbitol, pH 4.0 | 23 mM Acetate, 35 mM Phenylalanine, 4.2% sorbitol | 800 | 4.9 | 2.9 |

Figure 42:
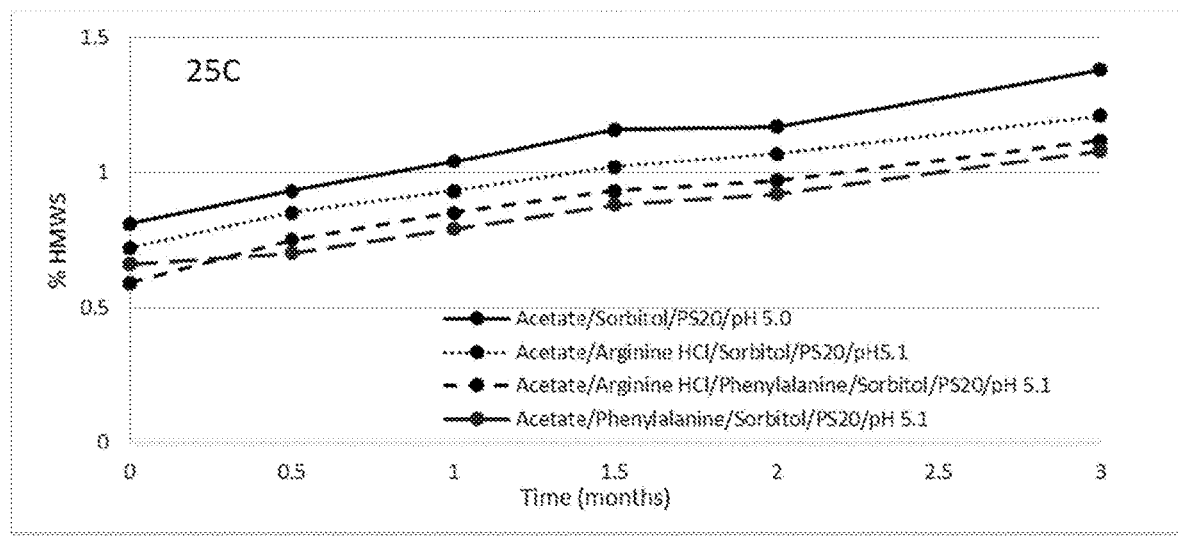
FIGS. 42 and 43 are graphs of the percent HMWS monitored by SE-UHPLC as a function of time at 25° C. for 3 months and 37° C. for 2 months, respectively, for the formulation having the Formulation name is Table 17.
Figure 43:
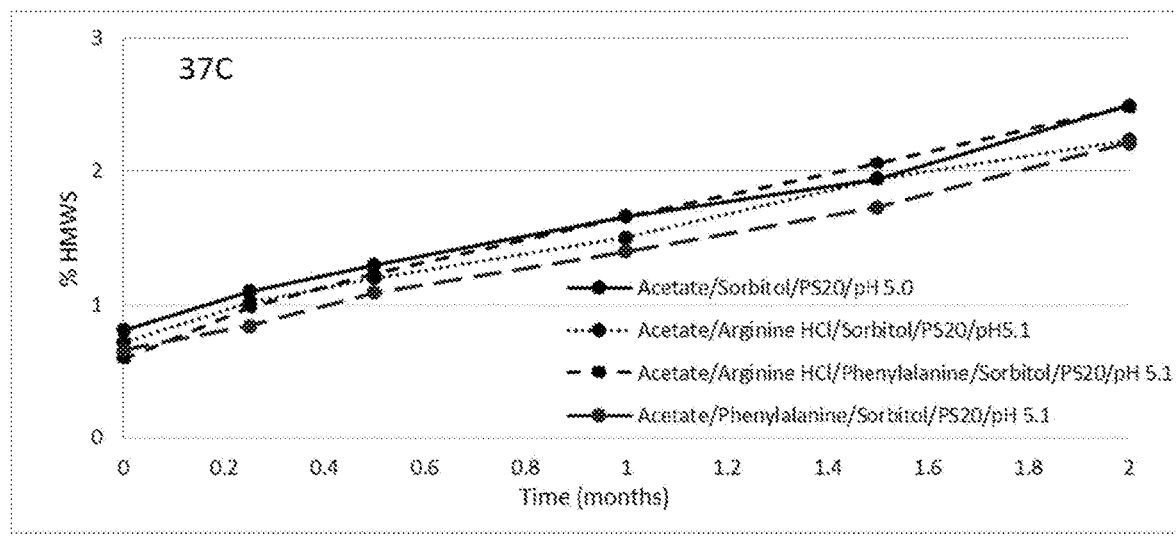

*Each final formulation comprises 120 mg/mL denosumab and 0.01% PS20 and the pH indicated in the Abbreviated Formulation Name FIGS. 42 and 43 show the percent HMWS monitored by SE-UHPLC as a function of formulation and time at 25° C. for 3 months and 37° C. for 2 months, respectively.

TABLES 18-21 show the same data in tabular form and also the increase in HMWS relative to the initial levels of HMWS.

TABLE 18

% HMWS level at 25° C. over 12 weeks

| | Formulation Name | Percentage HMWS | | | | | |
|---|---|---|---|---|---|---|---|
| | | 0 | 2 | 4 | 6 | 8 | 12 |
| 56 | Acetate/Sorbitol/pH 5.0 | 0.81 | 0.93 | 1.04 | 1.16 | 1.17 | 1.38 |
| 57 | Acetate/Arginine HCl/Sorbitol/pH 5.1 | 0.72 | 0.85 | 0.93 | 1.02 | 1.07 | 1.21 |
| 58 | Acetate/Arginine HCl/Phenylalanine/Sorbitol/pH 5.1 | 0.59 | 0.75 | 0.85 | 0.93 | 0.97 | 1.12 |
| 59 | Acetate/Phenylalanine/Sorbitol/pH 5.1 | 0.66 | 0.7 | 0.79 | 0.88 | 0.92 | 1.08 |

TABLE 19

HMWS increase at 25° C. over 12 weeks

| | Formulation | HMWS increase | | | | | |
|---|---|---|---|---|---|---|---|
| | | 0 | 2 | 4 | 6 | 8 | 12 |
| 56 | Acetate/Sorbitol/pH 5.0 | | 0.12 | 0.23 | 0.35 | 0.36 | 0.57 |
| 57 | Acetate/Arginine HCl/Sorbitol/pH 5.1 | | 0.13 | 0.21 | 0.3 | 0.35 | 0.49 |
| 58 | Acetate/Arginine HCl/Phenylalanine/Sorbitol/pH 5.1 | | 0.16 | 0.26 | 0.34 | 0.38 | 0.53 |
| 59 | Acetate/Phenylalanine/Sorbitol/pH 5.1 | | 0.04 | 0.13 | 0.22 | 0.26 | 0.42 |

TABLE 20

% HMWS level at 37° C. over 8 weeks

| | Formulation | Percentage HMWS | | | | |
|---|---|---|---|---|---|---|
| | | 0 | 2 | 4 | 6 | 8 |
| 56 | Acetate/Sorbitol/pH 5.0 | 0.81 | 1.3 | 1.66 | 1.94 | 2.49 |
| 57 | Acetate/Arginine HCl/Sorbitol/pH 5.1 | 0.72 | 1.2 | 1.5 | 1.94 | 2.23 |
| 58 | Acetate/Arginine HCl/Phenylalanine/Sorbitol/pH 5.1 | 0.59 | 1.23 | 1.66 | 2.06 | 2.48 |
| 59 | Acetate/Phenylalanine/Sorbitol/pH 5.1 | 0.66 | 1.09 | 1.4 | 1.73 | 2.21 |

TABLE 21

HMWS increase at 37° C. over 8 weeks

| | Formulation | HMWS increase | | | |
|---|---|---|---|---|---|
| | | 2 | 4 | 6 | 8 |
| 56 | Acetate/Sorbitol/pH 5.0 | 0.49 | 0.85 | 1.13 | 1.68 |
| 57 | Acetate/Arginine HCl/Sorbitol/pH 5.1 | 0.48 | 0.78 | 1.22 | 1.51 |
| 58 | Acetate/Arginine HCl/Phenylalanine/Sorbitol/pH 5.1 | 0.64 | 1.07 | 1.47 | 1.89 |
| 59 | Acetate/Phenylalanine/Sorbitol/pH 5.1 | 0.43 | 0.74 | 1.07 | 1.55 |

This example shows that addition of arginine, phenylalanine, and a combination thereof each reduces the level of initial HMWS (t=0) in high concentration denosumab formulations. At 25° C., the increase in HMWS is reduced in the phenylalanine Formulation 59, compared to the control Formulation 56. At 37° C., Formulations 57 and 59 have reduced HMWS formation compared to the control sorbitol Formulation 56. The formulation containing both arginine HCl and phenylalanine formed HMWS at a higher rate at 37° C. relative to the other formulations, indicating that the combination of these excipients is destabilizing to denosumab at such higher temperatures in this formulation.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. An aqueous pharmaceutical formulation comprising (i) a human anti-human receptor activator of nuclear factor kappa-B ligand (anti-RANKL) monoclonal antibody, or an antigen-binding portion thereof and (ii) an amino acid aggregation inhibitor, wherein the amino acid aggregation inhibitor is (a) an aromatic amino acid comprising a phenyl or an indole or (b) a hydrophobic amino acid which has a score greater than about 2.5 on the Kyte and Doolittle hydrophobicity scale.

2. The aqueous pharmaceutical formulation of claim 1, wherein the aromatic amino acid is L-phenylalanine or L-tryptophan.

3. The aqueous pharmaceutical formulation of claim 1, wherein the aromatic amino acid comprises a C1-C6 alkyl chain between the alpha carbon and the phenyl or indole.

4. The aqueous pharmaceutical formulation of claim 3, wherein the hydrophobic amino acid is L-valine, L-leucine, or L-isoleucine.

5. The aqueous pharmaceutical formulation of claim 1, comprising about 5 mM to about 300 mM of the amino acid aggregation inhibitor.

6. The aqueous pharmaceutical formulation of claim 5, comprising about 5 mM to about 180 mM amino acid aggregation inhibitor, optionally, L-phenylalanine.

7. The aqueous pharmaceutical formulation of claim 6, comprising about 5 mM to about 100 mM amino acid aggregation inhibitor, optionally, L-phenylalanine.

8. The aqueous pharmaceutical formulation of claim 1 (i) comprising only one amino acid aggregation inhibitor, (ii) wherein the molar ratio of the amino acid aggregation inhibitor to the anti-RANKL antibody is about 10 to 200, and/or (iii) further comprising a tonicity modifier, optionally, selected from the group consisting of: sorbitol, mannitol, sucrose, trehalose, glycerol, and combinations thereof.

9. The aqueous pharmaceutical formulation of claim 1, having a pH in a range of about 5.0 to about 5.4.

10. The aqueous pharmaceutical formulation of claim 1, (i) having a viscosity that is not more than about 6 cP at 5° C., optionally, wherein the viscosity is about 4.5 cP to about 5.5 cP, (ii) having a conductivity of about 500 µS/cm to about 2000 µS/cm, (iii) having an osmolality in a range of about 200 mOsm/kg to about 500 mOsm/kg, and/or (iv) comprising less than 2% high molecular weight species (HMWS) and/or more than 98% of the antibody main peak, as measured by SE-UHPLC, following storage at about 2° C. to about 8° C. for at least 12 months, 24 months, or 36 months.

11. The aqueous pharmaceutical formulation of claim 7, comprising about 25 mM to about 90 mM amino acid aggregation inhibitor, optionally, L-phenylalanine.

12. The aqueous pharmaceutical formulation of claim 11, comprising about 20 mM to about 50 mM amino acid aggregation inhibitor.

13. The aqueous pharmaceutical formulation of claim 9, wherein the pH is about 5.0 to about 5.2.

14. The aqueous pharmaceutical formulation of claim 10, wherein the osmolality is about 225 mOsm/kg to about 400 mOsm/kg.

15. The aqueous pharmaceutical formulation of claim 14, wherein the osmolality is about 250 mOsm/kg to about 350 mOsm/kg.

16. The aqueous pharmaceutical formulation of claim 1, comprising less than 2% high molecular weight species (HMWS) and/or more than 98% of the antibody main peak, as measured by SE-UHPLC, following storage at about 20° C. to about 30° C. for about 1 month.

17. The aqueous pharmaceutical formulation of claim 1, comprising less than 2% high molecular weight species (HMWS) and/or more than 98% of the antibody main peak, as measured by SE-UHPLC, following storage at about 2° C. to about 8° C. for at least 12 months, 24 months, or 36 months and a second storage at about 20° C. to about 30° C. for about 1 month.

18. The aqueous pharmaceutical formulation of claim 1, comprising less than 2% high molecular weight species (HMWS) and/or more than 98% of the antibody main peak, as measured by SE-UHPLC, following storage at about 37° C. for about one month or about 30° C. for 3 months.

19. The aqueous pharmaceutical formulation of claim 1, wherein the concentration of the antibody or antigen-binding portion thereof is greater than 70 mg/mL.

20. The aqueous pharmaceutical formulation of claim 19, wherein the concentration of the antibody or antigen-binding portion thereof is less than about 300 mg/mL.

21. The aqueous pharmaceutical formulation of claim 20, wherein the concentration of the antibody or antigen-binding portion thereof is less than about 200 mg/mL.

22. The aqueous pharmaceutical formulation of claim 21, wherein the concentration of the antibody or antigen-binding portion thereof is about 75 mg/mL to about 200 mg/mL.

23. The aqueous pharmaceutical formulation of claim 22, wherein the concentration of the antibody or antigen-binding portion thereof is about 100 mg/mL to about 140 mg/mL.

24. The aqueous pharmaceutical formulation of claim 1, further comprising a buffer and/or a surfactant.

25. The aqueous pharmaceutical formulation of claim 24, wherein the buffer is acetate or glutamate.

26. The aqueous pharmaceutical formulation of claim 25, comprising about 5 mM to about 60 mM buffer.

27. The aqueous pharmaceutical formulation of claim 26, comprising acetate buffer about 16 mM to about 41 mM acetate buffer.

28. The aqueous pharmaceutical formulation of claim 24, wherein the surfactant is polysorbate 20.

29. The aqueous pharmaceutical formulation of claim 24, comprising at least about 0.004 (w/v) % surfactant and less than 0.15 (w/v) % surfactant.

30. The aqueous pharmaceutical formulation of claim 8, comprising about 2.0 (w/w) % to about 5.0 (w/w) % sorbitol.

31. The aqueous pharmaceutical formulation of claim 1, wherein the anti-RANKL antibody is an IgG.

32. The aqueous pharmaceutical formulation of claim 31, wherein the anti-RANKL antibody is an IgG$_2$.

33. The aqueous pharmaceutical formulation of claim 1, wherein the anti-RANKL antibody, or antigen-binding portion thereof, comprises (A) a light chain variable domain comprising a light chain CDR1 comprising the amino acid sequence of SEQ ID NO: 5, a light chain variable domain comprising a light chain CDR2 comprising the amino acid sequence of SEQ ID NO: 6, and a light chain variable domain comprising a light chain CDR3 comprising the amino acid sequence of SEQ ID NO:7; and (B) a heavy chain variable domain comprising a heavy chain CDR1 comprising the amino acid sequence of SEQ ID NO: 8, a heavy chain variable domain comprising a heavy chain CDR2 comprising the amino acid sequence of SEQ ID NO: 9, and a heavy chain variable domain comprising a heavy chain CDR3 comprising the amino acid sequence of SEQ ID NO: 10.

34. The aqueous pharmaceutical formulation of claim 33, wherein the anti-RANKL antibody, or antigen-binding portion thereof, comprises a light chain variable region of SEQ ID NO: 1 and a heavy chain variable region of SEQ ID NO: 2.

35. The aqueous pharmaceutical formulation of claim 34, wherein the anti-RANKL antibody, or antigen-binding portion thereof, comprises a light chain of SEQ ID NO: 13 and a heavy chain of SEQ ID NO: 14.

36. The aqueous pharmaceutical formulation of claim 12, comprising about 20 mM to about 50 mM L-phenylalanine or L-tryptophan.

37. A container, optionally, a vial, pre-filled syringe (PFS), or glass container containing an aqueous pharmaceutical formulation of claim 1.

38. A method of treating a skeletal-related event (SRE), a giant cell tumor of bone, hypercalcemia, or osteoporosis or increasing bone mass, in a subject, comprising administering to the subject the aqueous pharmaceutical formulation of claim 1.

39. The method of claim 38, wherein the method comprises (a) treatment of an SRE in a subject with bone metastases from solid tumors, (b) treatment of an SRE in a subject who is an adult or a skeletally mature adolescent with giant cell tumor of bone that is unresectable or where surgical resection is likely to result in severe morbidity, (c) treatment of hypercalcemia of malignancy refractory to bisphonsphonate therapy in a subject, (d) treatment of an SRE in a subject with multiple myeloma or with bone metastases from a solid tumor, (e) treatment of osteoporosis of postmenopausal women at high risk for fracture, (f) treatment to increase bone mass in women at high risk for fracture receiving adjuvant aromatase inhibitor therapy for breast cancer, (g) treatment to increase bone mass in men at high risk for fracture receiving androgen deprivation therapy for nonmetastatic prostate cancer, (h) treatment to increase bone mass in men with osteoporosis at high risk for fracture, (i) therapy with calcium or vitamin D.

40. A method of making a stable, aqueous pharmaceutical formulation comprising a human anti-human receptor activator of nuclear factor kappa-B ligand (anti-RANKL) monoclonal antibody, or an antigen-binding portion thereof, comprising combining the anti-RANKL monoclonal antibody, or antigen-binding portion thereof, at a concentration greater than 70 mg/mL with an amino acid aggregation inhibitor, a buffer, a surfactant, and optionally, a tonicity modifier, wherein the amino aggregation inhibitor is (a) an aromatic amino acid comprising a phenyl or an indole or (b) a hydrophobic amino acid which has a score greater than about 2.5 on the Kyte and Doolittle hydrophobicity scale.

41. A stable, aqueous pharmaceutical formulation made according to claim 40.

42. A method of improving the stability of an aqueous pharmaceutical formulation comprising a human anti-human receptor activator of nuclear factor kappa-B ligand (anti-RANKL) monoclonal antibody or an antigen-binding portion thereof, at a concentration of greater than 70 mg/mL, comprising:

preparing said aqueous pharmaceutical formulation comprising said human anti-human receptor activator of nuclear factor kappa-B ligand (anti-RANKL) monoclonal antibody or an antigen-binding portion thereof at a pH in a range of about 5.0 to less than 5.2 or in admixture with an amino acid aggregation inhibitor, wherein the amino aggregation inhibitor is (a) an aromatic amino acid comprising a phenyl or an indole or (b) a hydrophobic amino acid which has a score greater than about 2.5 on the Kyte and Doolittle hydrophobicity scale, wherein said aqueous pharmaceutical formulation demonstrates improved stability at the pH in a range of about 5.0 to less than 5.2 compared to an equivalent aqueous pharmaceutical formulation that is not at a pH in a range of about 5.0 to less than 5.2 or with the amino acid aggregation inhibitor compared to an equivalent aqueous pharmaceutical formulation without the amino acid aggregation inhibitor.

* * * * *